US010278734B2

(12) United States Patent
Sanders et al.

(10) Patent No.: US 10,278,734 B2
(45) Date of Patent: May 7, 2019

(54) CLAMPING DEVICE FOR USE WITH AN ANATOMIC EXTERNAL FIXATION DEVICE

(71) Applicant: QuikFix, LLC, Wilmington, DE (US)

(72) Inventors: Roy W. Sanders, Tampa, FL (US); Sergio Gutierrez, Tampa, FL (US)

(73) Assignee: FOOT INNOVATIONS, LLC, Tampa, FL (US)

( * ) Notice: Subject to any disclaimer, the term of this patent is extended or adjusted under 35 U.S.C. 154(b) by 3 days.

(21) Appl. No.: 15/701,104

(22) Filed: Sep. 11, 2017

(65) Prior Publication Data
US 2018/0021065 A1 Jan. 25, 2018

Related U.S. Application Data

(63) Continuation of application No. 15/359,479, filed on Nov. 22, 2016, now Pat. No. 9,867,637, which is a continuation-in-part of application No. 14/871,618, filed on Sep. 30, 2015, now Pat. No. 9,597,117.

(60) Provisional application No. 62/058,262, filed on Oct. 1, 2014.

(51) Int. Cl.
A61B 17/64 (2006.01)
(52) U.S. Cl.
CPC ...... A61B 17/6416 (2013.01); A61B 17/6425 (2013.01); A61B 17/6458 (2013.01); A61B 17/6466 (2013.01); A61B 17/645 (2013.01)
(58) Field of Classification Search
CPC ........... Y10T 24/4441; Y10T 244/4513; A61B 17/6416
See application file for complete search history.

(56) References Cited

U.S. PATENT DOCUMENTS

| 2,346,346 A | 4/1944 | Anderson |
| 4,433,677 A | 2/1984 | Ulrich et al. |
| 4,895,141 A | 1/1990 | Koeneman et al. |
| 5,116,334 A | 5/1992 | Cozad et al. |
| 5,242,240 A * | 9/1993 | Gorham ................ A61B 17/02 403/389 |
| 5,380,325 A | 1/1995 | Lahille et al. |

(Continued)

FOREIGN PATENT DOCUMENTS

| CN | 203749538 | 8/2016 |
| DE | 29916855 U1 | 1/2000 |

OTHER PUBLICATIONS

European Search Report for application EP 17203163 dated Apr. 17, 2018 6 pages.

(Continued)

Primary Examiner — Lynnsy M Summitt
Assistant Examiner — Tara Rose E Carter
(74) Attorney, Agent, or Firm — Shabbi S. Khan; Foley & Lardner LLP

(57) ABSTRACT

A clamping device includes a clamp body and a locking assembly. The clamp body includes a first jaw defining a first opening and a second jaw defining a second opening. The locking assembly includes a first locking element, a second locking element, and a lever. The first locking element includes a first end and a shaft portion extending from the first end. The shaft portion is sized to pass through the first opening and the second opening. The locking assembly is configured to reduce a distance between the first jaw and the second jaw responsive to rotation of the second locking element. The lever is configured to attach to the second locking element and rotate about the second locking element from a first position to a second position to cause the distance between the first jaw and the second jaw to be reduced further.

18 Claims, 63 Drawing Sheets

(56) References Cited

U.S. PATENT DOCUMENTS

| | | | |
|---|---|---|---|
| 5,443,464 A | 8/1995 | Russell et al. |
| 5,443,465 A | 8/1995 | Pennig |
| 5,624,440 A | 4/1997 | Huebner |
| 5,653,707 A | 8/1997 | Taylor et al. |
| 5,707,372 A | 1/1998 | Errico et al. |
| 6,277,069 B1 | 8/2001 | Gray |
| 7,465,303 B2 | 12/2008 | Riccione et al. |
| 7,803,174 B2 | 9/2010 | Denis et al. |
| 2003/0187432 A1 | 10/2003 | Johnson et al. |
| 2005/0228376 A1 | 10/2005 | Boomer et al. |
| 2006/0229602 A1 | 10/2006 | Olsen |
| 2006/0229604 A1 | 10/2006 | Olsen et al. |
| 2007/0149973 A1 | 6/2007 | Clement et al. |
| 2007/0161983 A1 | 7/2007 | Cresina et al. |
| 2007/0161987 A1 | 7/2007 | Capote et al. |
| 2009/0118733 A1 | 5/2009 | Orsak et al. |
| 2010/0318084 A1 | 12/2010 | Hajianpour |
| 2016/0095624 A1 | 4/2016 | Sanders et al. |

OTHER PUBLICATIONS

International Preliminary Report on Patentability for PCT/US2015/053316 dated Apr. 13, 2017.
International Search Report for PCT/US2015/053316 dated Apr. 8, 2016.
Non-Final Office Action on U.S. Appl. No. 15/463,999 dated Aug. 8, 2018.
Notice of Allowance on U.S. Appl. No. 14/871,598 dated Jul. 21, 2016.
Notice of Allowance on U.S. Appl. No. 14/871,598 dated Jun. 8, 2016.
Notice of Allowance on U.S. Appl. No. 14/871,613 dated Dec. 7, 2016.
Notice of Allowance on U.S. Appl. No. 14/871,618 dated Dec. 30, 2016.
Notice of Allowance on U.S. Appl. No. 15/359,479 dated Sep. 26, 2017.
Office Action on U.S. Appl. No. 14/871,613 dated Aug. 26, 2016.
Office Action on U.S. Appl. No. 14/871,613 dated May 5, 2016.
Office Action on U.S. Appl. No. 14/871,618 dated Aug. 12, 2016.
Office Action on U.S. Appl. No. 15/359,479 dated Feb. 10, 2017.
Partial International Search Report on International Application No. PCT/US2015/053316 dated Jan. 26, 2016 (FTI-005PC).
U.S. Office Action for U.S. Appl. No. 14/871,598 dated Feb. 11, 2016 ((FTI-005US)).
U.S. Office Action on U.S. Appl. No. 15/359,479 dated Jun. 16, 2017.
Written Opinion of the Searching Authority for PCT/US2015/053316 dated Apr. 8, 2016.

* cited by examiner

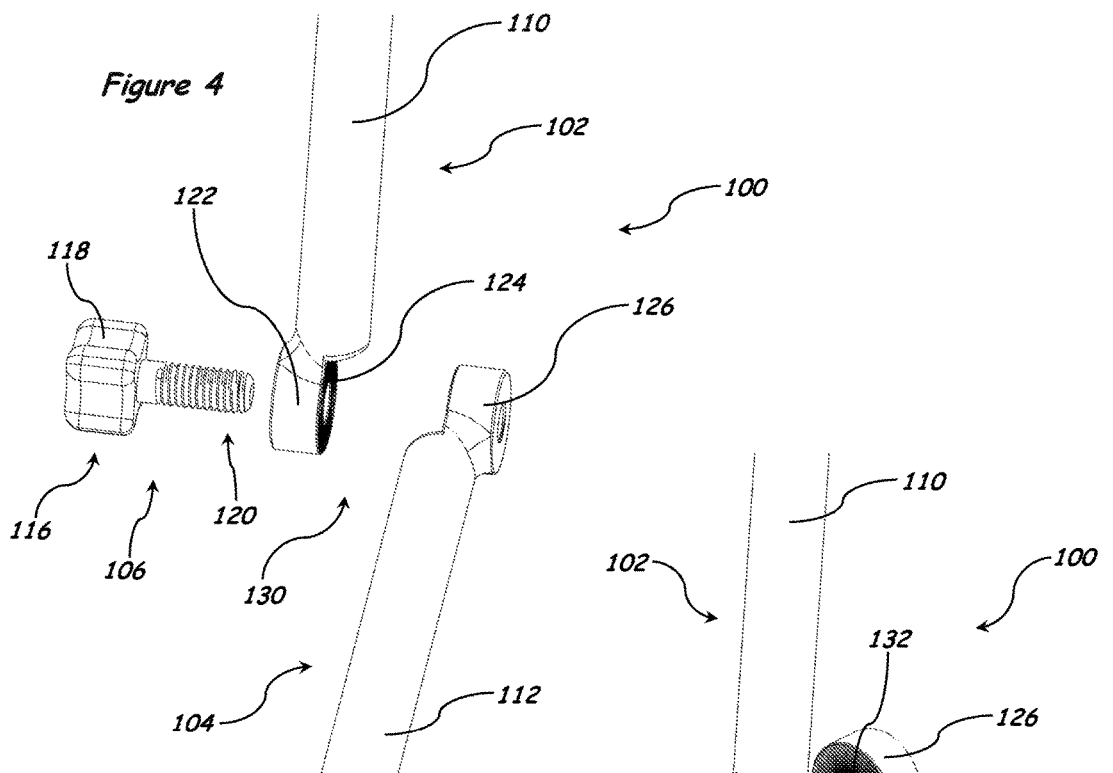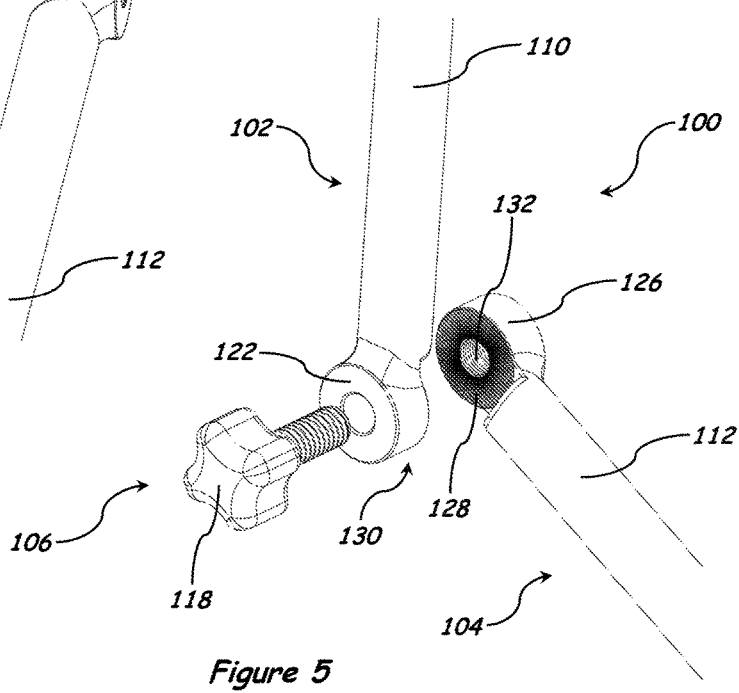

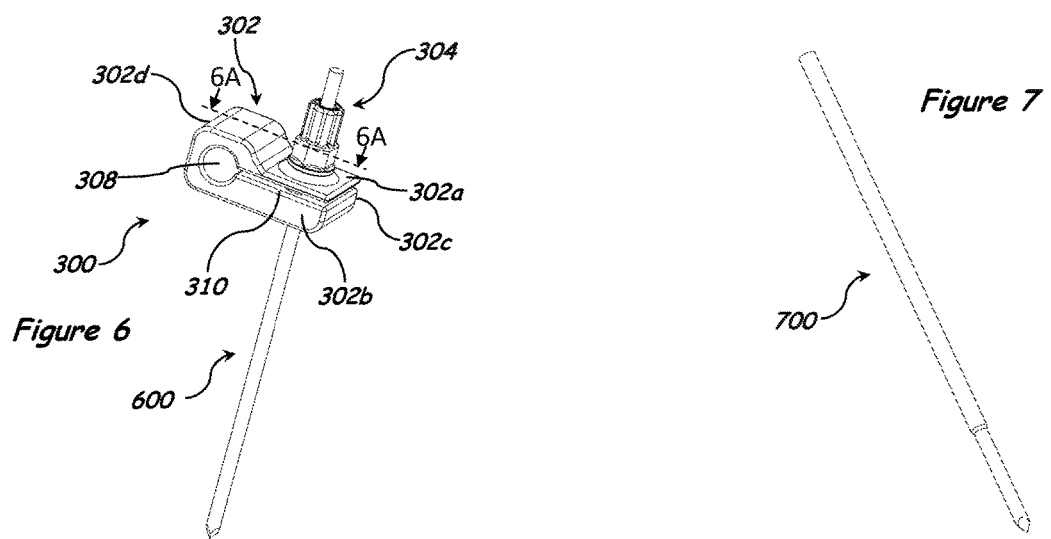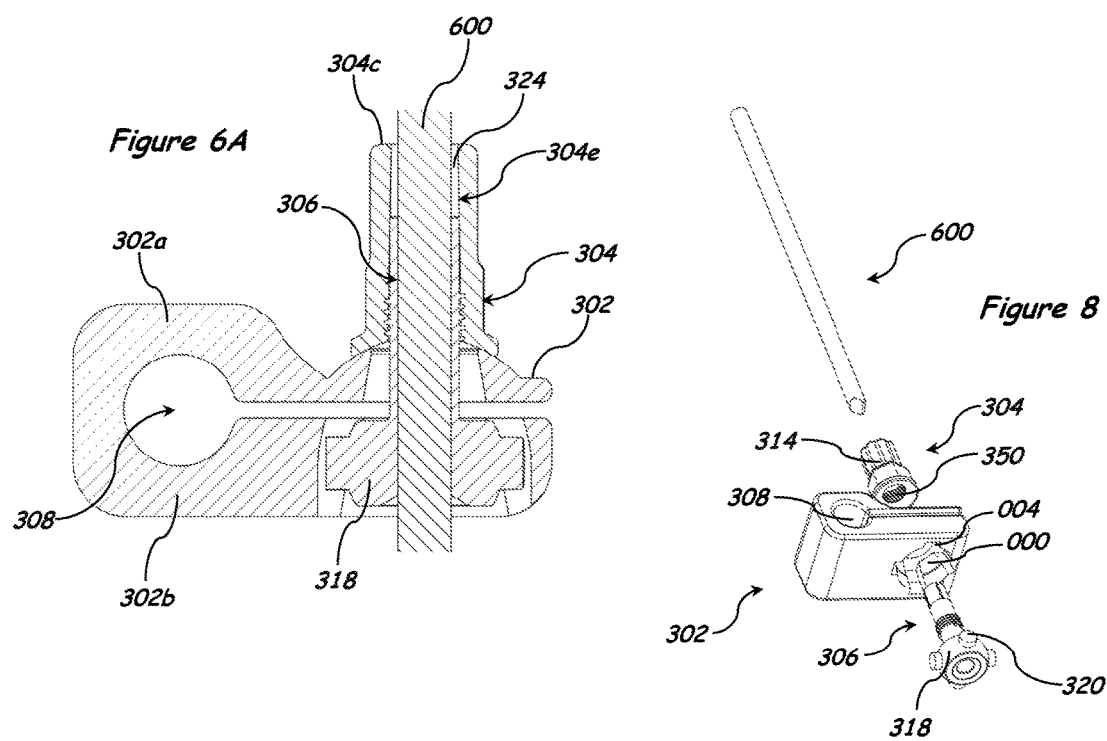

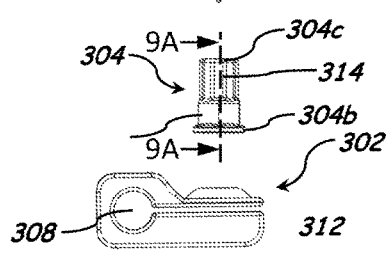
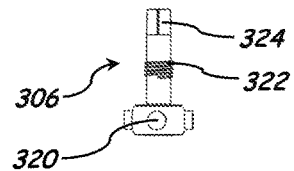
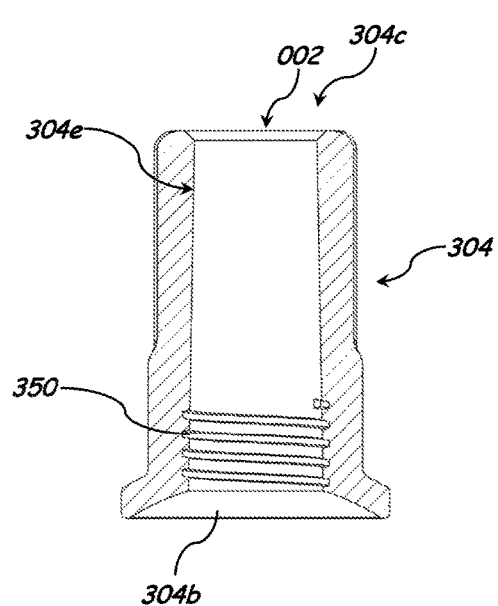
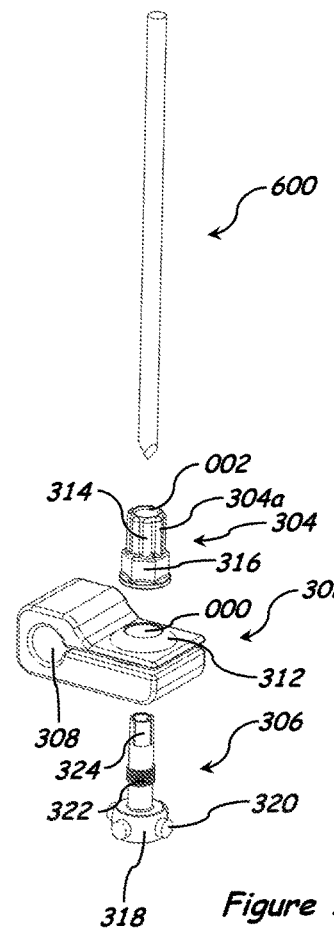
Figure 9
Figure 9A
Figure 10

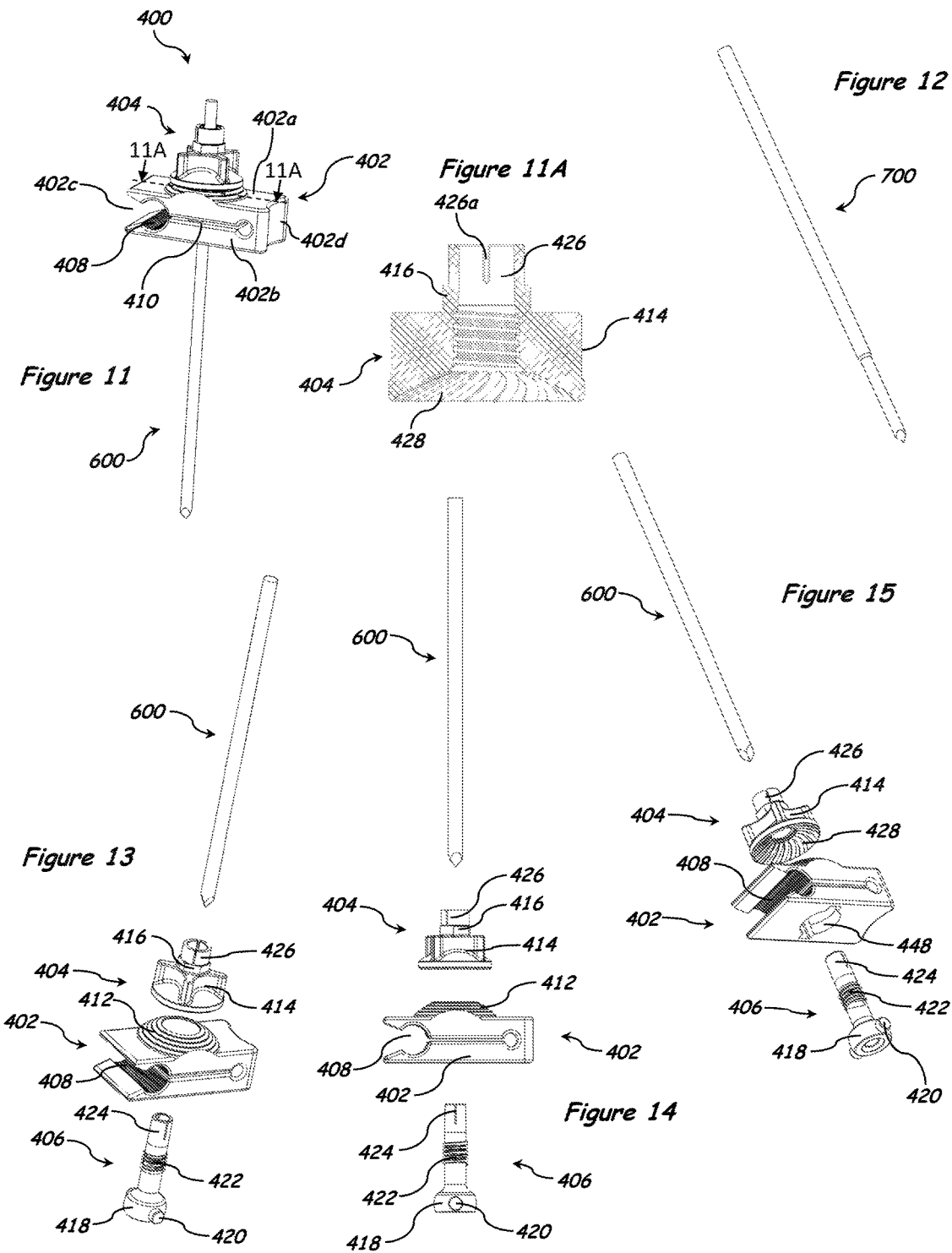

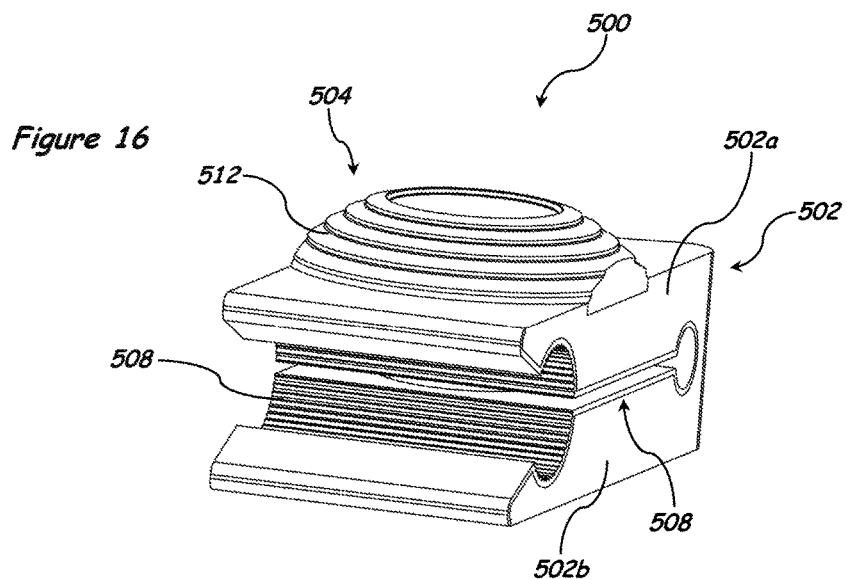
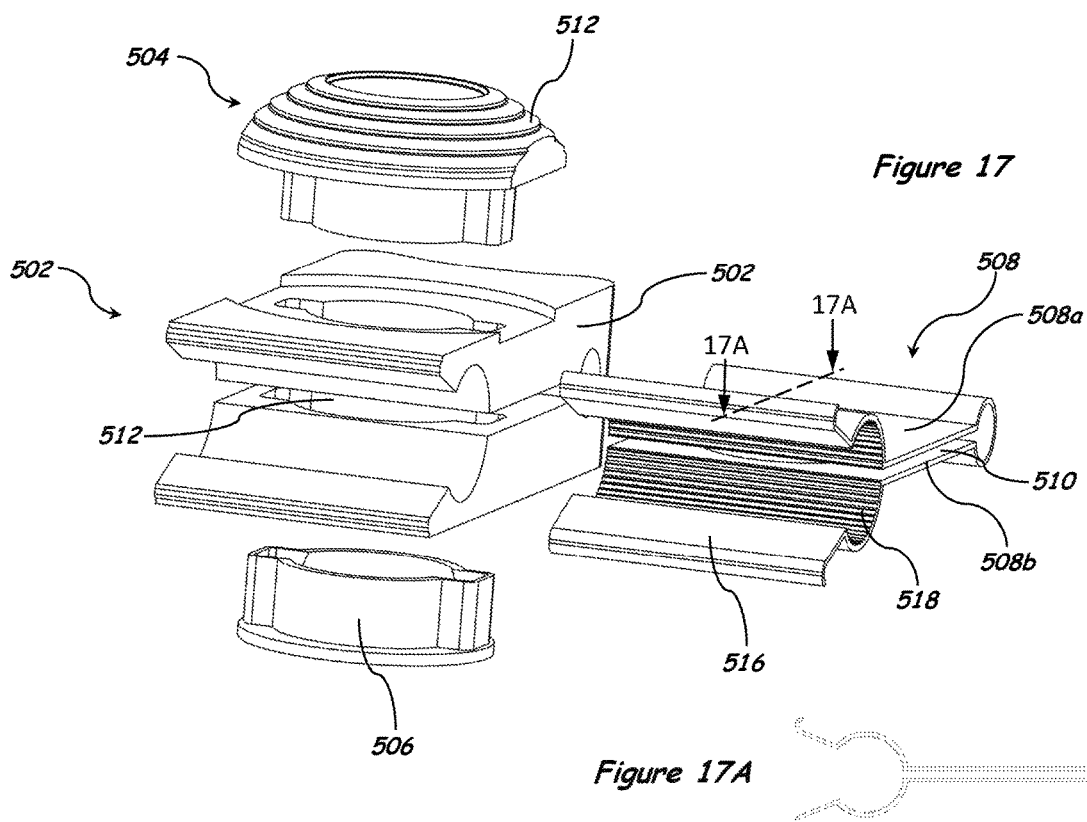

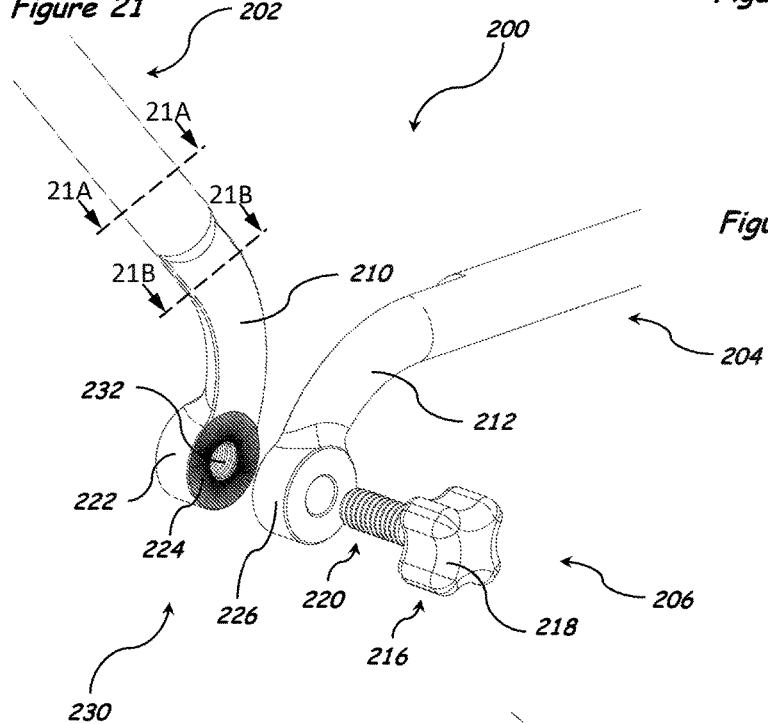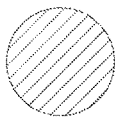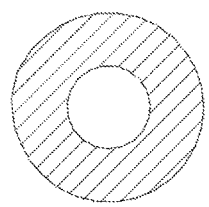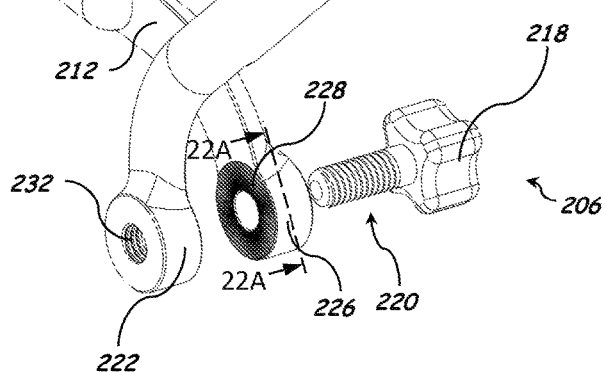

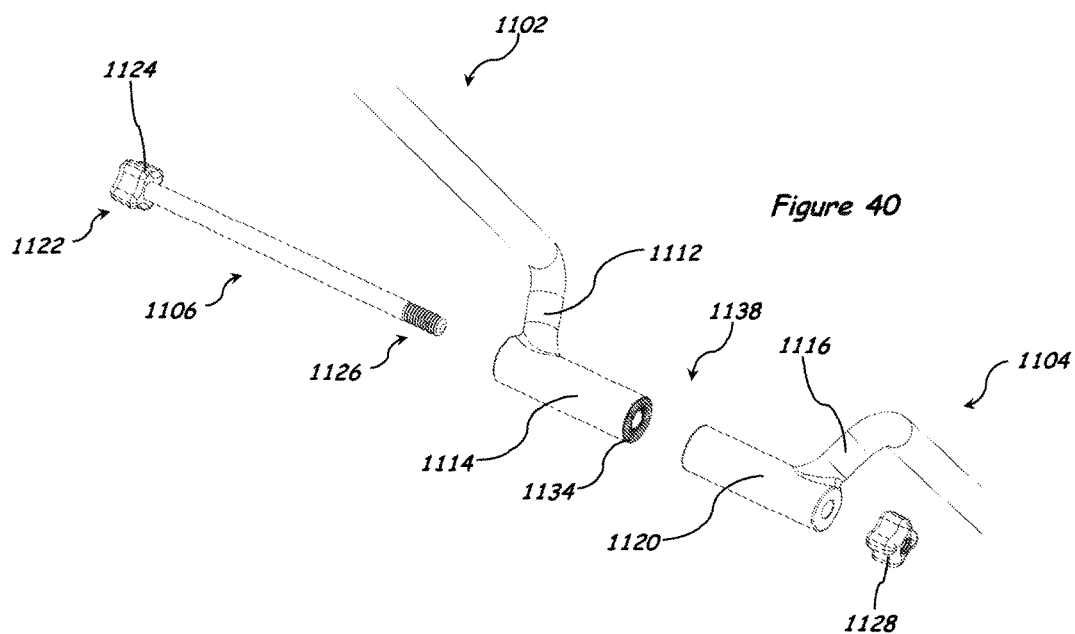
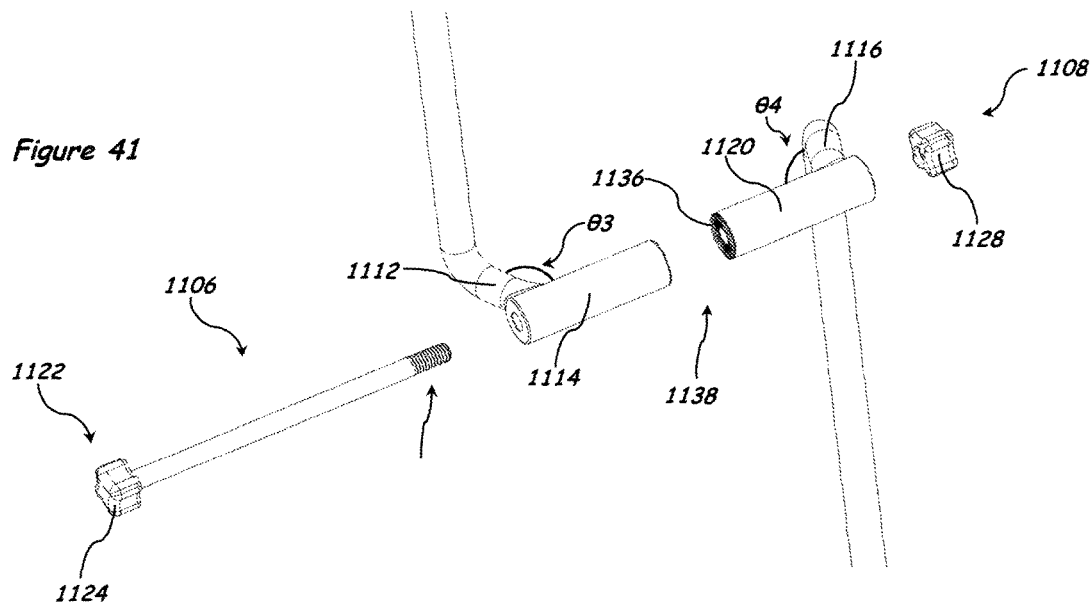

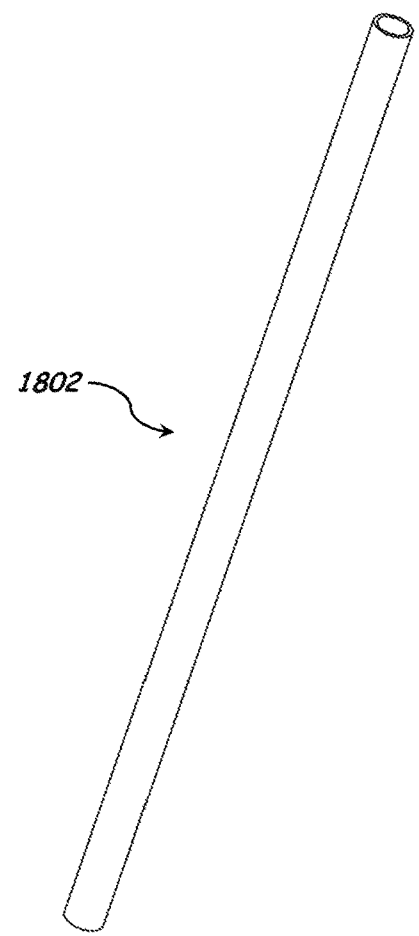
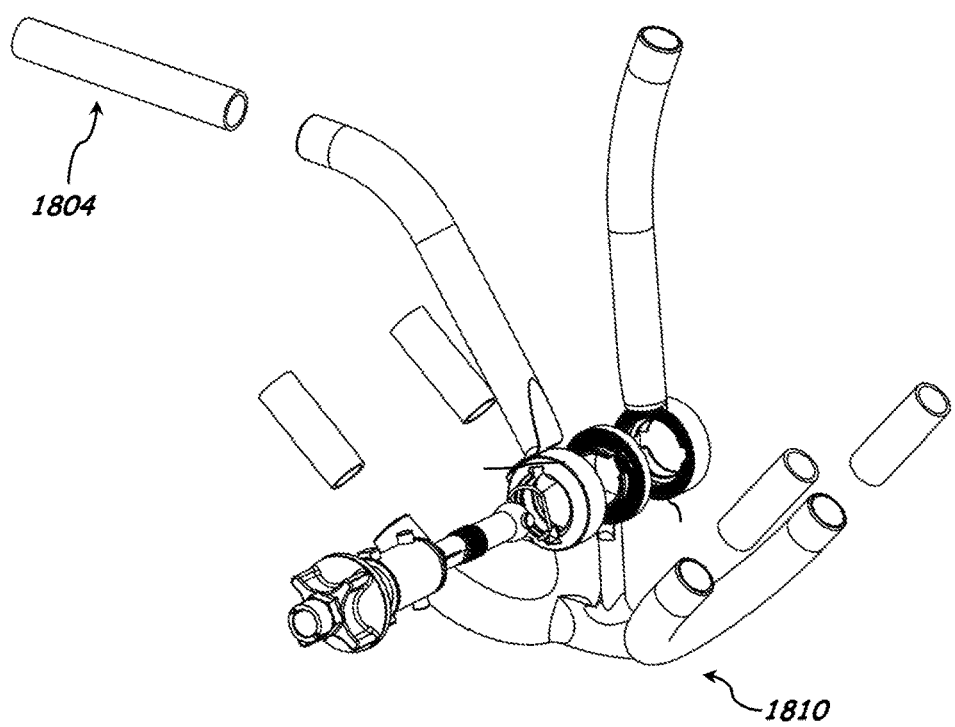
Figure 68

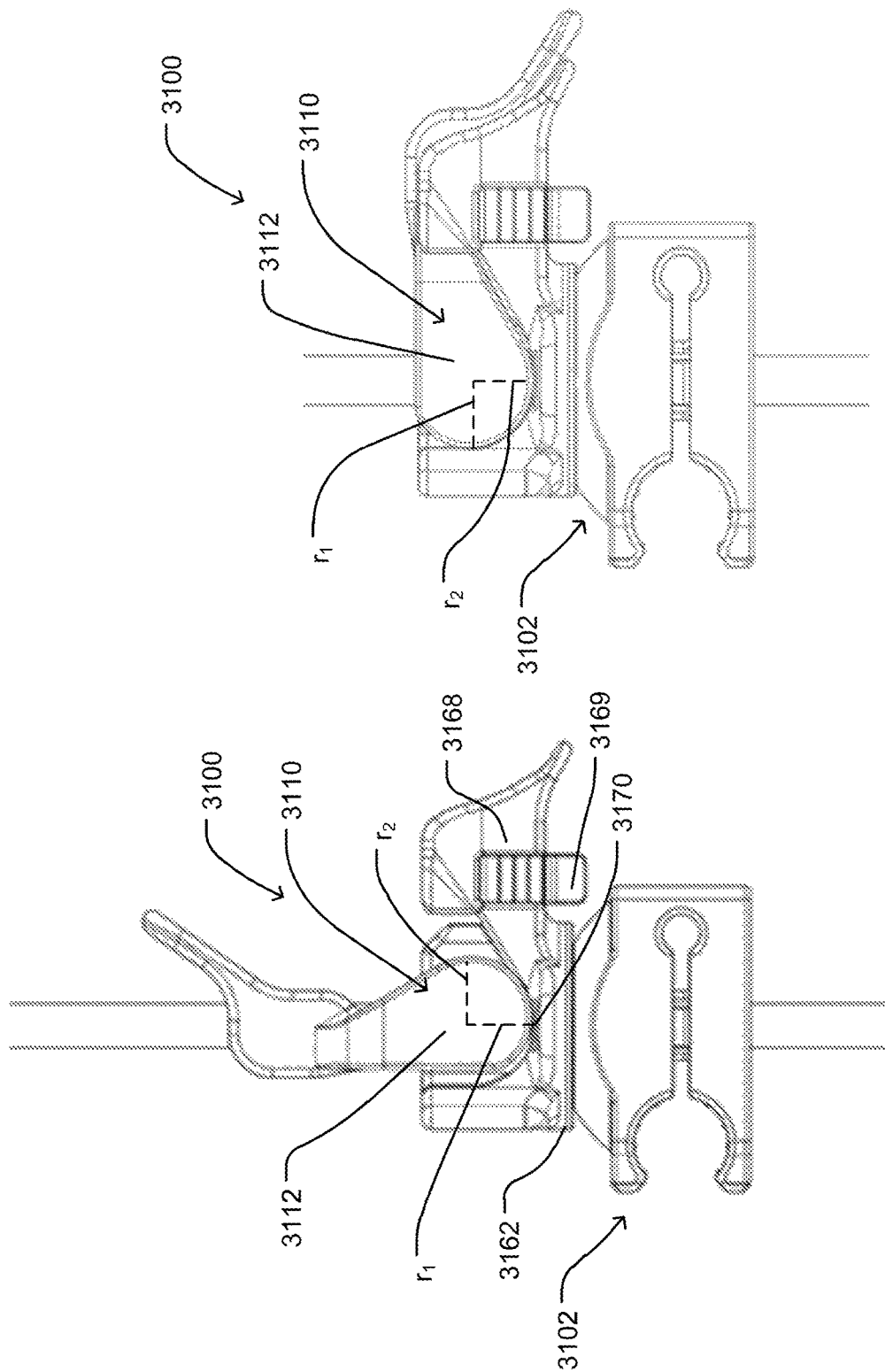

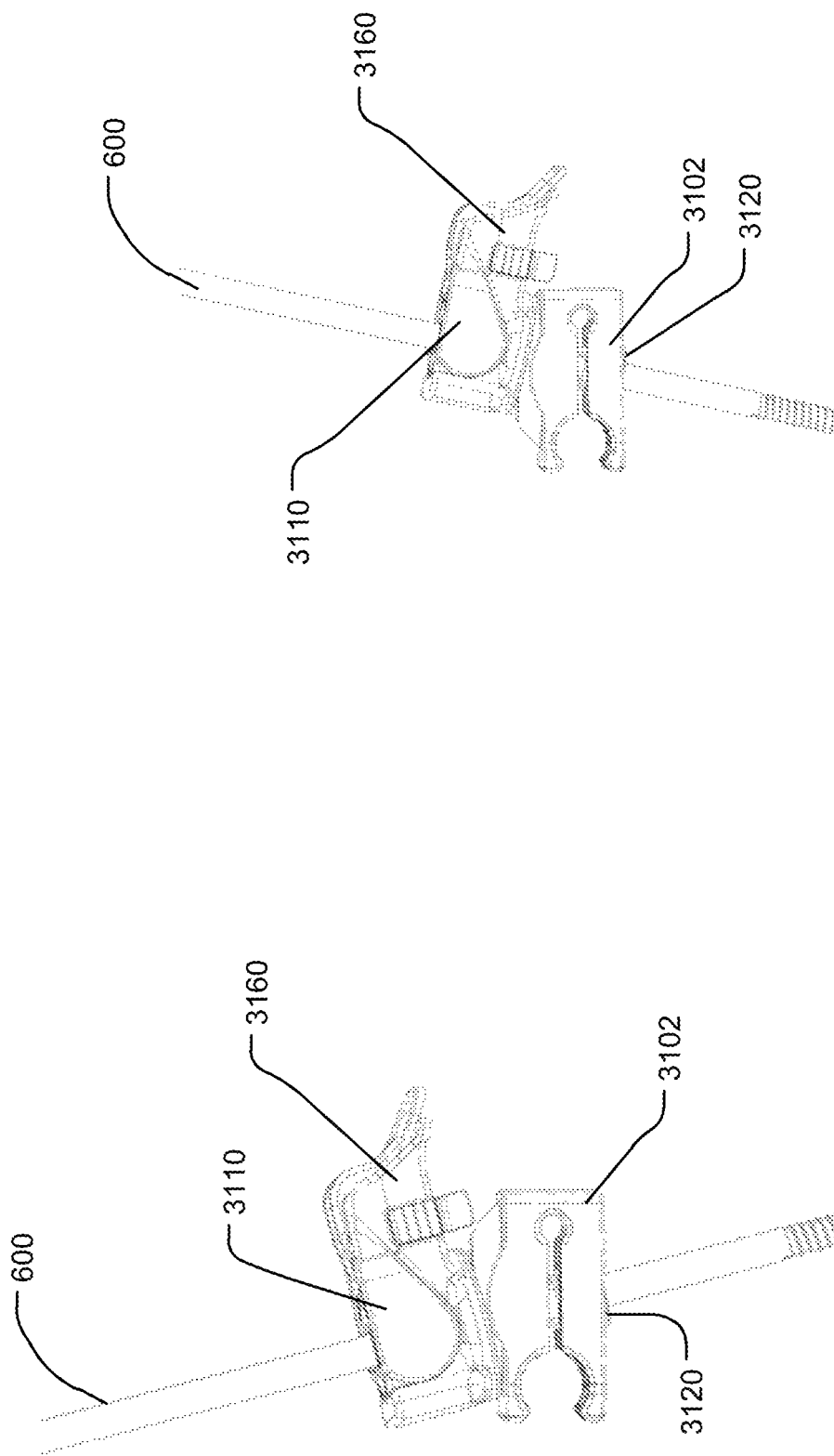

CLAMPING DEVICE FOR USE WITH AN ANATOMIC EXTERNAL FIXATION DEVICE

CROSS-REFERENCE TO RELATED APPLICATIONS

This application is a continuation of U.S. patent application Ser. No. 15/359,479, entitled "CLAMPING DEVICE FOR USE WITH AN ANATOMIC EXTERNAL FIXATION DEVICE," filed Nov. 22, 2016, which is a continuation-in-part of U.S. patent application Ser. No. 14/871,618, entitled "CLAMPING DEVICE FOR USE WITH AN ANATOMIC EXTERNAL FIXATION SYSTEM," filed on Sep. 30, 2015, which claims priority to U.S. Application 62/058,262, entitled "Anatomic External Fixation Device," filed on Oct. 1, 2014, the disclosures of which are incorporated herein by reference in their entireties for all purposes.

TECHNICAL FIELD

The present disclosure relates generally to fracture fixation systems, methods, and components. More particularly, the disclosure relates to improved anatomic external fixation systems, methods, and components. Particular embodiments described herein can be used to set bone fragments in long or flat bone fractures (e.g., tibia fractures, femur fractures, fibula fractures, pelvis fractures, etc. . . . ).

BACKGROUND

External fixation devices have been widely used in the treatment of long bone fractures and are best suited in cases of unstable, comminuted fractures. An example of this would be a compound fracture of the tibia that would generally be fixed with a cast. If the fracture is too comminuted, the cast will be unable to provide enough support to the fragments, thus leading to a malunion or a nonunion. The external fixation device helps stabilize the bone fragments and allow the patient a quicker recovery time with fewer complications.

Current external fixation devices consist of straight rods and ring-frames made of carbon fiber that can be interconnected through the use of clamps. The clamps can be two sided with one side clamping to the straight bar and the other side clamping to a bone pin that is fixed to a bone or bone fragment. These two clamps are connected to each other via a rotating joint joint that allows for some adjustability along one plane, thus allowing various angles in between the rods and the pins. Once the surgeon has adjusted the rods and pins to the desired positions, they have to lock everything in place by tightening nuts on each side of the clamp. The process of locking each clamp in place can be cumbersome and may require multiple assistants to aid in the procedure. This adds complexity and wastes valuable resources.

External fixator devices with hinges for fixing injury around joints such as the elbow, the knee, and the ankle are generally designed for use only on the right side or only on the left side of the joint or limb. These hinged systems must be mounted on the bone with the mechanical pivot axis of the device aligned with the natural pivot axis of the joint. These designed limitations not only demand that hospitals dedicate a large inventory for accommodating high volume of external fixator devices, but also increase surgical time and complexity in installing the devices on patients.

Therefore, a need exists for improved external fixation systems, methods, and components for use in fracture fixation.

SUMMARY

The present disclosure provides components and systems for externally fixing and precisely adjusting fractures in general, and more particularly fractures in a bone or near a joint, such as fractures near the elbow, knee, and ankle. The components and systems according to some exemplary embodiments wherein the same system can be used on either the right side or the left side of a bone or joint. According to some other exemplary embodiments, a single system can be used across both sides of the bone or joint simultaneously. The systems and their components include unitary construction, unitary modular construction and modular construction.

According to an aspect of the present disclosure, a clamping device for an external fixation system includes a clamp body and a locking assembly. The clamp body includes a first jaw and a second jaw and defines a first channel configured to accommodate a fixation element along a longitudinal axis of the first channel. The first jaw defines a first opening and the second jaw defines a second opening. The locking assembly includes a first locking element, a second locking element, and a lever configured to couple to the second locking element. The first locking element includes a first end and a shaft portion extending from the first end. The shaft portion is sized to pass through the first opening and the second opening. The second opening is sized to restrict the first end from passing through the second opening. The first locking element defines a second channel sized to receive a bone pin. The locking assembly is configured to reduce a distance between the first jaw and the second jaw responsive to rotation of the second locking element relative to the first locking element. The lever is configured to attach to the second locking element and rotate about the second locking element from a first position to a second position to cause the distance between the first jaw and the second jaw to be reduced further while the first end is in contact with the second opening.

According to another aspect of the present disclosure, a clamping device for an external fixation system includes a clamp body and a locking assembly. The clamp body includes a first jaw and a second jaw. The first jaw defines a first opening and the second jaw defines a second opening. The locking assembly includes a first locking element, a second locking element, and a lever. The first locking element includes a first end and a shaft portion extending from the first end. The shaft portion is sized to pass through the first opening and the second opening. The lever is configured to be attached to the second locking element and rotated about the second locking element to cause a distance between the first jaw and the second jaw to be reduced while the first locking element is in contact with the second opening.

Some or all of the systems, components and subcomponents of the present invention can be single-use or disposable. Also some or all of the systems, components and subcomponents of the present invention can be made of a unitary construction (formed from a single piece of metal or material) or unitary modular construction (plurality of components and/or subcomponents permanently connected by standard means, such as injection molding, welding, or soldering), or of modular construction (plurality of components and/or subcomponents removably connected by standard means, such as threading or snap-fitting).

These and other features of various embodiments can be understood from a review of the following detailed description in conjunction with the accompanying drawings.

It is to be understood that both the foregoing general description and the following detailed description are exemplary and explanatory and are not restrictive of the present invention, as claimed.

BRIEF DESCRIPTION OF THE DRAWINGS

FIG. 4 is a detailed anterior-medial exploded view of the first embodiment of the elbow external fixator.

FIG. 5 is a detailed anterior-lateral exploded view of the first embodiment of the elbow external fixator.

FIG. 6 is a perspective view of a first embodiment of a closed clamp that can be utilized in all the embodiments of the external fixator.

FIG. 6A is a cross-sectional view taken along the line 6A-6A of FIG. 6

FIG. 7 is a perspective view of a double diameter pin that can be utilized in the first embodiment of the closed clamp.

FIG. 8 is an exploded bottom perspective view of the first embodiment of the closed clamp that can be utilized in all the embodiments of the external fixator.

FIG. 9 is an exploded side view of the first embodiment of the closed clamp that can be utilized in all the embodiments of the external fixator.

FIG. 9A is a cross-sectional view taken along the line 9A-9A of FIG. 9

FIG. 10 is an exploded top perspective view of the first embodiment of the closed clamp that can be utilized in all the embodiments of the external fixator.

FIG. 11 is a perspective view of a first embodiment of an open clamp that can be utilized in all the embodiments of the external fixator.

FIG. 11A is a cross-sectional view taken along the line 11A-11A of FIG. 11

FIG. 12 is a perspective view of a double diameter pin used in the first embodiment of the open clamp.

FIG. 13 is an exploded top perspective view of the first embodiment of the open clamp that can be utilized in all the embodiments of the external fixator.

FIG. 14 is an exploded side view of the first embodiment of the open clamp that can be utilized in all the embodiments of the external fixator.

FIG. 15 is an exploded bottom perspective view of the first embodiment of the open clamp that can be utilized in all the embodiments of the external fixator.

FIG. 16 is a perspective view of a third embodiment of a multiple-part/multiple-material open clamp that can be utilized in all the embodiments of the external fixator.

FIG. 17 is an exploded perspective view of the third embodiment of the multiple-part/multiple-material open clamp that can be utilized in all the embodiments of the external fixator.

FIG. 17A is a cross-sectional view taken along the line 17A-17A of FIG. 17.

FIG. 21 is a detailed posterior-lateral exploded view of the second embodiment of the elbow external fixator.

FIG. 21A is a cross-sectional view taken along the line 21A-21A of FIG. 21.

FIG. 21B is a cross-sectional view taken along the line 21B-21B of FIG. 21.

FIG. 22 is a detailed anterior-lateral exploded view of the second embodiment of the elbow external fixator.

FIG. 22A is a cross-sectional view taken along the line 22A-22A of FIG. 22.

FIG. 40 is a detailed superior-medial exploded view of the fourth embodiment of the knee external fixator.

FIG. 41 is a detailed superior-lateral exploded view of the fourth embodiment of the knee external fixator.

FIG. 68 is a detailed posterior-medial exploded view of the sixth embodiment of the ankle external fixator.

FIG. 74A is a side view of an embodiment of the clamping device of FIG. 71 in which the lever is in a first position.

FIG. 74B is a side view of an embodiment of the clamping device of FIG. 71 in which the lever is in a second position.

FIG. 76A is a side view of an embodiment of the clamping device of FIG. 71 in which the bone pin is secured in a first orientation.

FIG. 76B is a side view of an embodiment of the clamping device of FIG. 71 in which the bone pin is secured in a second orientation.

DETAILED DESCRIPTION

Figure 1:
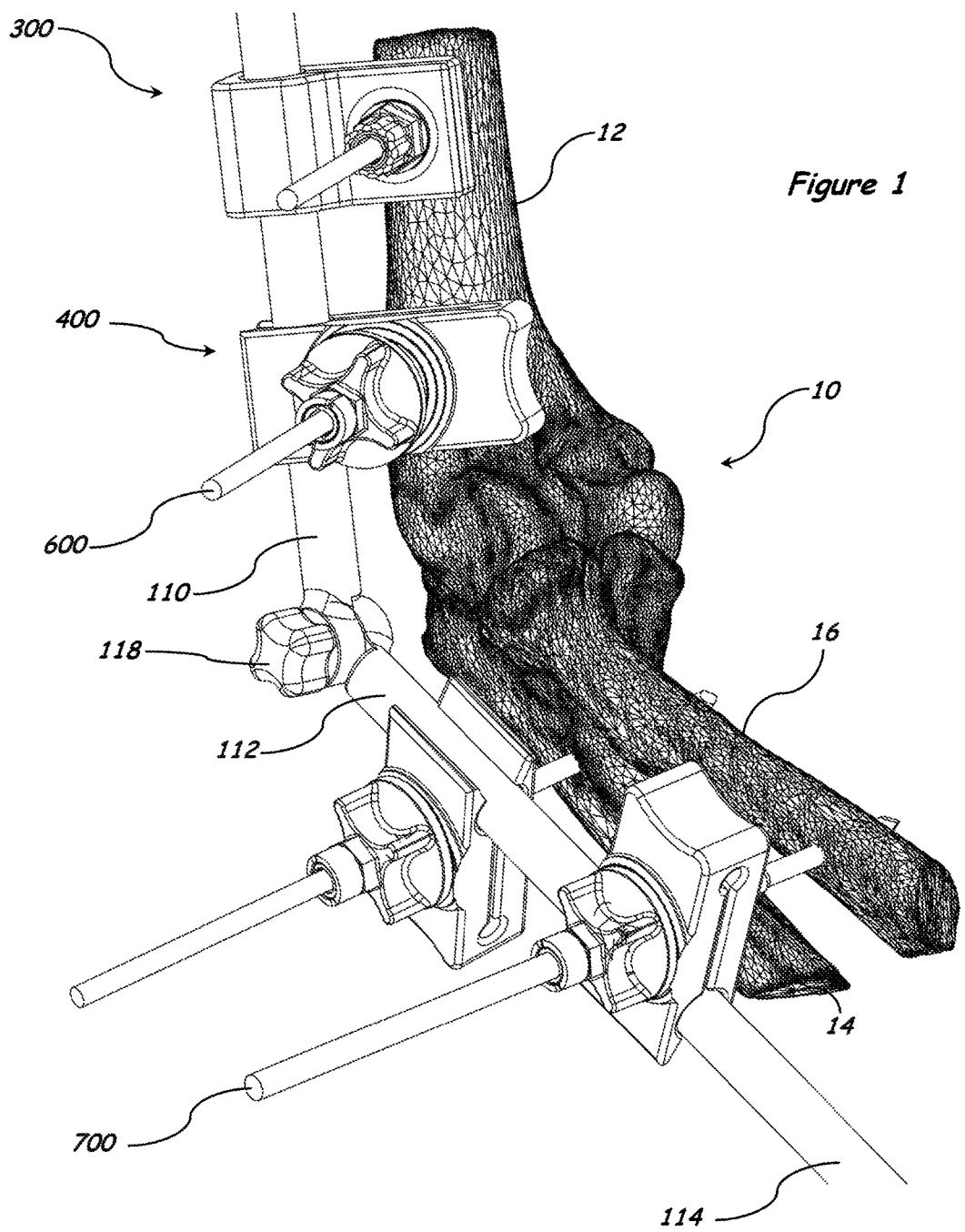
FIG. 1 is a superior-lateral perspective view of an elbow with a first embodiment of the elbow external fixator and its associated clamps.

The following detailed description and the appended drawings describe and illustrate various exemplary external fixation systems, methods, and components. The description and drawings are exemplary in nature and are provided to enable one skilled in the art to make and use one or more exemplary external fixation systems and/or components, and/or practice one or more exemplary methods. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "exemplary" refers to "an example of" and is not intended to convey a meaning of an ideal or preferred embodiment. The use of "attached" and "coupled" grammatically related terms refers to the fixed, releasable, or integrated association of two or more elements and/or devices with or without one or more other elements in between. Thus, the term "attached" or "coupled" and grammatically related terms includes releasably attaching or fixedly attaching two or more elements and/or devices in the present or absence of one or more other elements in between. As used herein, the terms "proximal" and "distal" are used to describe opposing axial ends of the particular elements or features being described in relation to anatomical placement. As used herein, the terms "proximal," "distal," "inferior," "posterior," and any other relative position terms are intended to facilitate clarity regarding the disclosed embodiments, and do not limit the disclosure to any particular frame of reference.

While the systems, methods, and components described herein are exemplified by systems and methods for external fixation of bones, the systems, methods, and components described and illustrated herein can be used to treat any suitable ailment or joint within the body of an animal, including, but not limited to, humans. Skilled artisans will be able to select a suitable ailment and/or joint within the body of an animal to utilize a system and/or method described herein according to a particular embodiment based on various considerations, including the type of ailment and/or the structural arrangement at a treatment site. Example joints considered suitable to utilize a system, method, and/or component described herein include, but are not limited to, the elbow joint, the knee joint, and the ankle joint.

A. External Fixation Systems and Clamping Systems

In some embodiments, components disclosed herein may be disposed in a substantially perpendicular orientation (e.g., having longitudinal axes that are less than 20 degrees from 90 degrees apart, less than 10 degrees from 90 degrees apart, less than 5 degrees from 90 degrees apart, less than 1 degree from 90 degrees apart, etc.). In some embodiments, components disclosed herein may be disposed in a substantially coplanar (e.g., being disposed in planes that are less than 20 degrees from coplanar, less than 10 degrees from coplanar, less than 5 degrees from coplanar, less than 1 degree from coplanar, etc.).

Figure 2:
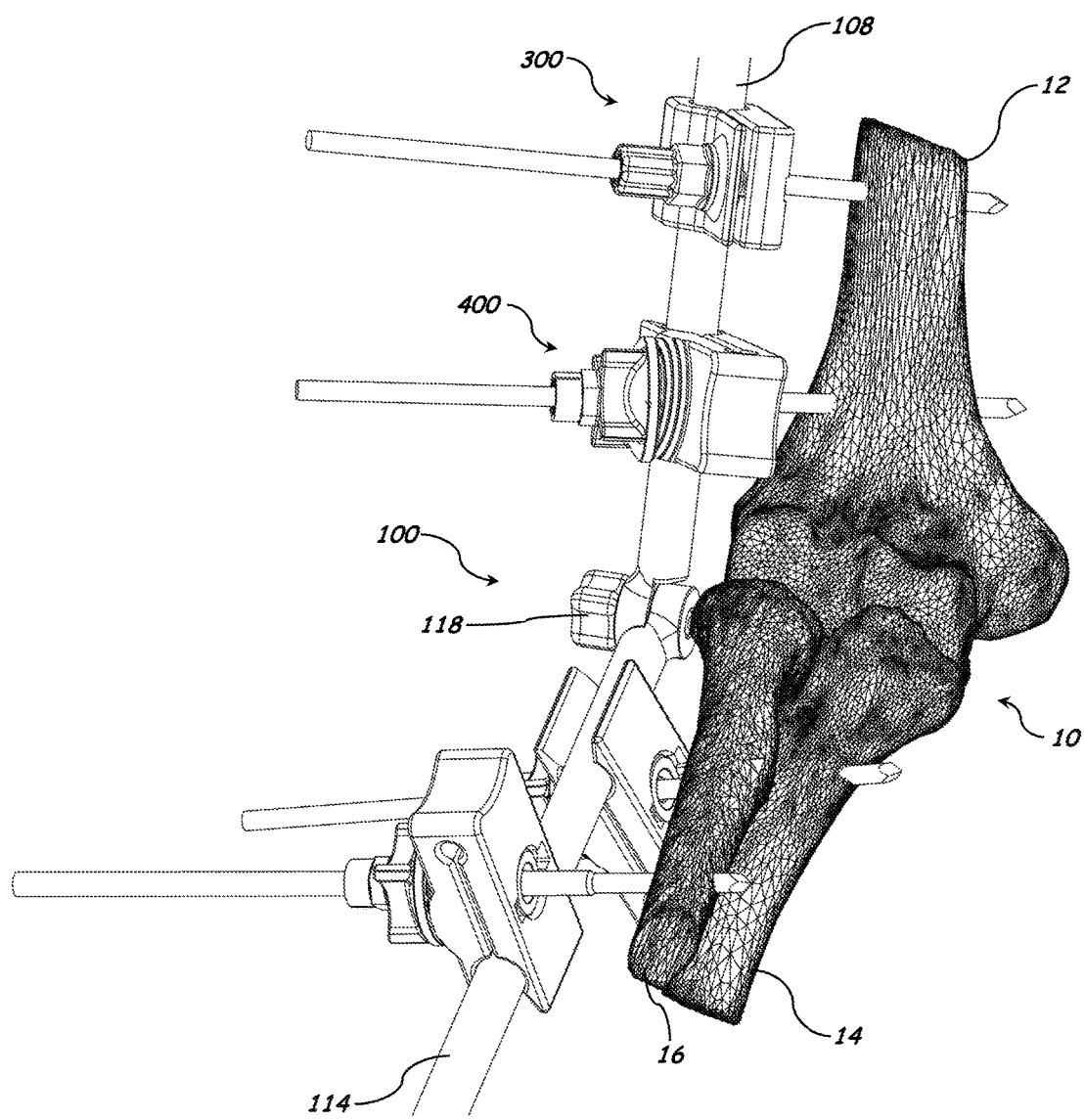
FIG. 2 is a superior-medial perspective view of an elbow with the first embodiment of the elbow external fixator and its associated clamps.
Figure 3:
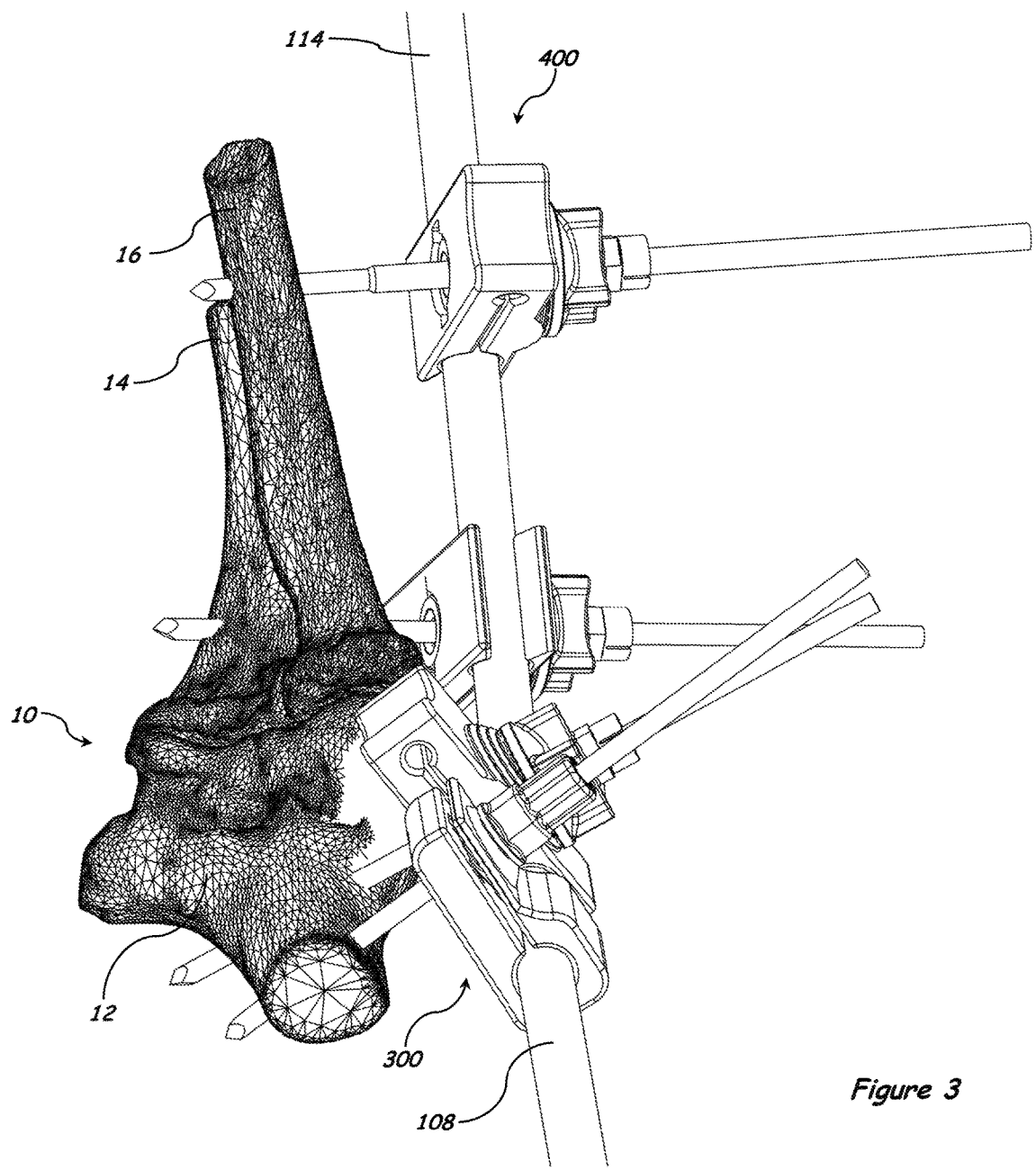
FIG. 3 is a superior perspective view of an elbow with the first embodiment of the elbow external fixator and its associated clamps.
Figure 15A:
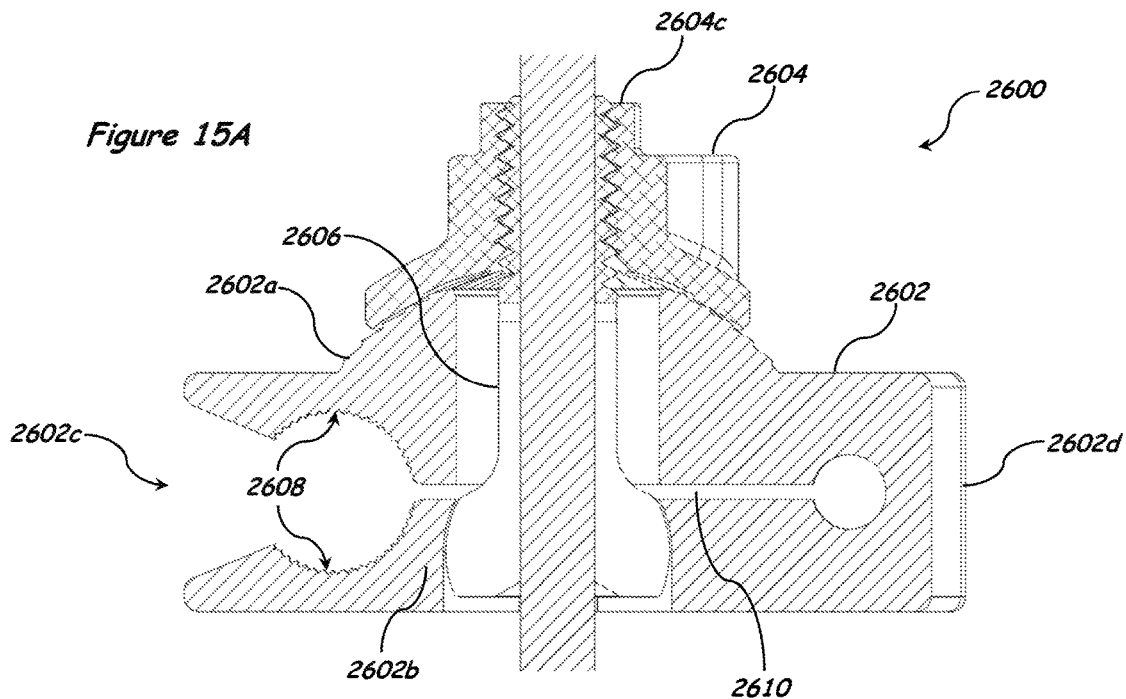
FIG. 15A is a cross-sectional view of a second embodiment of the open clamp system that can be utilized in all the embodiments of the external fixator.
Figure 15B:
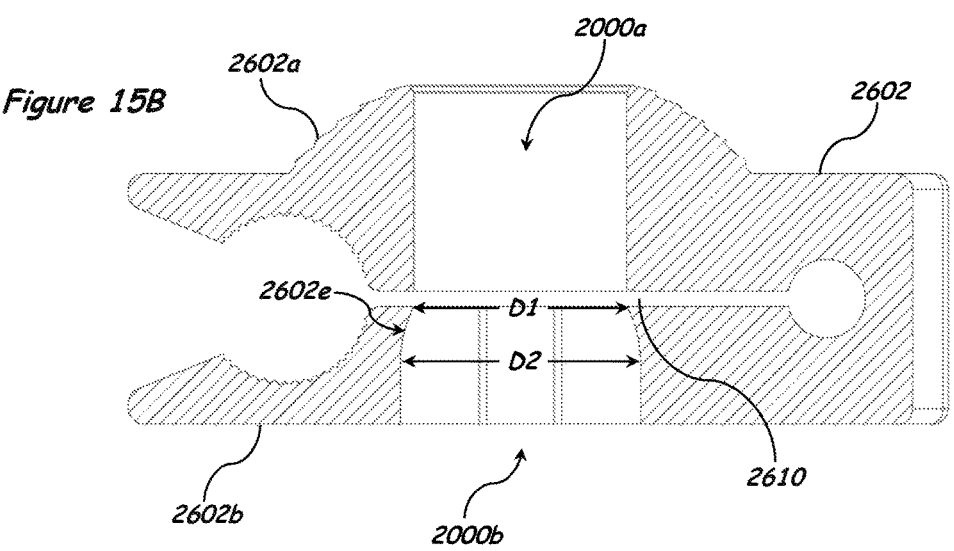
FIG. 15B is a cross-sectional view of the clamp body of FIG. 15A.
Figure 15C:
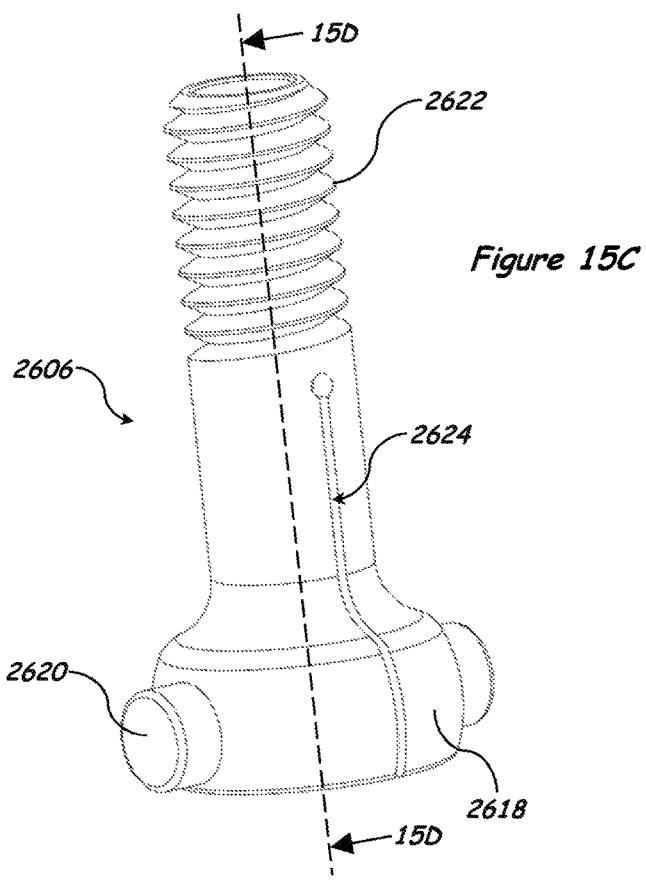
FIG. 15C is a side view of the shaft of FIG. 15A.
Figure 15D:
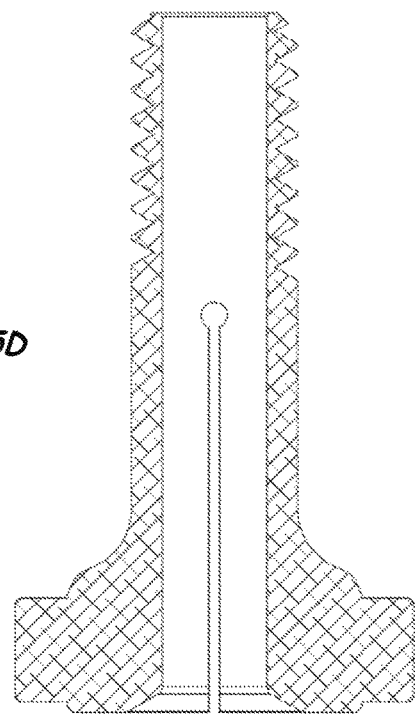
FIG. 15D is a cross-sectional view taken along the line 15D-15D of FIG. 15C.

FIGS. 1-3 illustrate an exemplary human elbow 10 comprising a humerus 12, ulna 14, and radius 16 and one embodiment of an exemplary elbow-spanning external fixation system 100.

FIGS. 1-5 illustrate a first embodiment of an exemplary elbow-spanning external fixation system 100 comprising a first external fixation component 102, a second external fixation component 104, a fastener or locking means 106, a closed-end clamp system 300 and an open-end clamp system 400. The first external fixation component 102 can be adapted to attach to the humerus 12, the ulna 14 and/or the radius 16 by use of the closed-end clamp system 300 and/or open-end clamp system 400. The second external fixation component 104 can be adapted to attach to the humerus 12, the ulna 14 and/or the radius 16 by use of the closed-end clamp system 300 and/or open-end clamp system 400.

The first external fixation component 102, second external fixation component 104, fastener 106, closed-end clamp system 300 and open-end clamp systems 400 and 500 (shown in FIGS. 16-17) can be formed of any suitable material known to one skilled in the art that provides an adequate stiffness or resistance to torsion, stress, torque and/or other forces that may be applied to the system 100, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form a first external fixation component, a second external fixation component, a fastener, a closed-end clamp system and an open-end clamp system of aluminum, stainless steel and/or carbon fiber, at least because these materials have properties that are well suited to external fixation of fractures.

In the illustrated embodiment 100 shown in FIGS. 1-5, the first external fixation component 102 comprises a first component proximal (e.g., first) end portion 108 and a first component distal (e.g., second) end portion 110. At least a portion of the first component proximal end portion 108 and at least a portion of the first component distal end portion 110 can be straight or curved. The first component distal end portion 110 includes a pivot structure 122 having a rough surface 124 and a through-bore having a circular cross-sectional shape for receiving a fastener such as fastener 106. The second external fixation component 104 comprises a second component proximal (e.g., first) end portion 112 and a second component distal (e.g., second) end portion 114. At least a portion of the second component proximal end portion 112 can be straight or curved. The second component proximal end portion 112 also includes a pivot structure 126 having a rough surface 128 and a threaded through-bore 132 having a circular cross-sectional shape for receiving a fastener such as fastener 106. The first external fixation component 102 and second external fixation component 104 are coupled and locked via a locking means such as a fastener 106 having a head 116 and at least a portion of its shaft threaded 120. The fastener 106 is configured to extend through the through-bore of the first pivot structure 122 and the threaded through-bore of the second pivot structure 126 to form a threaded connection with the second pivot structure 126 to form a movable hinge, articulator or mechanical joint 130. The hinge 130 is then locked in position by further tightening the fastener 106 which then interlocks the rough surface 124 of the first pivot structure 122 with the rough surface 128 of the second pivot structure 126. The interlocking or engagement of the rough surfaces 124 and 128 prevents the first and second external components 102 and 104 from rotating relatively to each other in a locking state.

Each of the first and second external fixation components 102 and 104 including their respective pivot structures 122 and 126 can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy). The first and second external fixation components 102 and 104 each can have any cross-sectional shape including circular, and non-circular such as oval, square, rectangle, triangle, or any polygonal shapes, and the cross-sectional shape can be different along the length of each component (e.g. semi-circle, circle). Each of the first and second external fixation components 102 and 104 can have uniform or varying diameter or thickness along its length. The first external fixation component 102 can be dimensioned and/or shaped to be the same or different from the second external fixation component 104.

The pivot structures 122 and 126 can be integrally formed or permanently attached by standard means such as welding or soldering or gluing, or removably coupled by standard means such as threading or snap-fitting, to any locations along the length of their respective first and second external fixation components 102 and 104 including the portion disposed between the distal end portion and the proximal end portion of each external fixation components 102 and 104. The pivot structures 122 and 126 can have any cross-sectional shape including circular, and non-circular such as oval, square, rectangle, triangle, or any polygonal shape. The length of each of the pivot structures 122 and 126 as measured along its axis of rotation or mechanical pivot axis X can be the same or different from the diameter or thickness of their respective first and second external fixation components 102 and 104. The end surfaces 124 and 128 of pivot structures 122 and 126 comprising the rough surface each lies in a plane perpendicularly intersecting the mechanical pivot axis, but can also lie in a plane intersecting the mechanical pivot axis at an angle other than 90 degrees. The rough surfaces 124 and 128 can include serration or radial interdigitation or other irregularly shaped features which provide friction enhancement or anti-rotation to the fixation components in a locking state. One skilled in the art may choose to have the rough surfaces be disposed on an outer surface of one of the first and second pivot structures 122 and 126 and on an inner surface of the other of the first and second pivot structures 122 and 126 to provide anti-rotation. The rough surfaces can also be provided as separate inserts coupled to the pivot structures 122 and 126. The pivot structures 122 and 126 can be an integral part of their respective external fixation components 102 or 104 or can be formed separately and assembled together later by welding, soldering or threading, for example. The pivot structures 122 and 126 each can be made of a unitary structure, a unitary modular or multi-component structure, or modular structure. An example of a modular pivot structure may include a pivot structure 122 or 126 having a non-circular cross-sectional shaped through-bore for receiving an insert having a matching, non-circular cross-sectional shape and a circular cross-sectional shaped through-bore with or without threads.

The locking means, such as fastener 106, comprises an enlarged structure, such as a head 116, with secure gripping surface features or geometry 118 for ease of handling the fastener during surgery, and a shaft 120 having engagement features such as threads which establish a threaded connection with the threaded through-bore 132 of the pivot structure 126 in the second external fixation component 104 during coupling and locking the external fixation components. The engagement features on the shaft can also include fins, protrusions or other fastening features known to one skilled in the art. The fastener 106 can also be a unitary, unitary modular or modular structure. An example of a modular fastener include a fastener as described but without the engagement features on is shaft, and a sleeve having engagement features on its outer surface adapted to cover the shaft of the fastener. The locking means can also include a first fastener such as fastener 106 and a second fastener such as a threaded nut. In this exemplary dual fastener system, both pivot structures 122 and 126 can have through-bores without threads or any engagement features, and arranged between the head of the first fastener and the nut. As the first fastener 106 or the second fastener (the threaded nut) is tightened down, the external fixation components 102 and 104 are coupled and locked in position.

FIGS. 6-15 describe various embodiments of a novel bone clamp configured to provide simple locking of various fixation elements such as wires, pins, rods and bars simultaneously. These clamping devices as described below can be used with the external fixation systems of the present invention to couple to bones, or with any existing or commercialized external fixation systems.

FIGS. 6-10 show an embodiment of a closed-end clamp system 300 comprising a clamp body 302, a knob 304 and a shaft 306. The clamp body 302 having an open end 302c and a close or hinged end 302d connecting an upper jaw 302a to a lower jaw 302b forming a groove or aperture 308 for receiving an external fixation element such as the first or second external fixation components 102 and 104, and a slot or spacing 310 in communication with the aperture 308. Each of the upper and lower jaws 302a and 302b have a through-bore 000 formed in alignment and configured for receiving and operatively interacting with at least a portion of a locking element or locking assembly such as the shaft 306 configured for operably interacting with the knob 304 for locking the clamp system 300.

The knob 304 comprises a knob body 304a having a clamp body facing end 304b and an opposing end 304c and a through-bore dimensioned for receiving and operatively interacting with a shaft, such as shaft 306, and extending longitudinally from the clamp body facing end 304b to the opposing end 304c. The knob body 304a includes a funnel-like or frusto-conical internal surface 304e or an internal surface having one of more tapered facets to guide, receive and alternatively compress and release a slit end, or a funnel-like or tapered external surface, of a shaft such as the shaft 306 for clamping a fixation element such as bone pin 600. The funnel-like or frusto-conical internal surface 304e, or more generally the through-bore bound by walls extending from the clamp body facing end 304b to the opposing end 304c of the knob body 304a, is designed to be larger toward the clamp body facing end 304b than toward the opposing end 304c of the knob body 304a, and includes a first locking feature such as threads 350. The tapered internal surface 304e can also be an insert. The through-bore 002 or opening in the opposing end 304c of the knob 304 has a diameter smaller than the uncompressed diameter of the slit end 324 of the shaft 306 to provide interference fit among the inner surface 304e of the knob 304, the slit end 324 and the bone pin such as bone pin 600. The opposing end 304c of the knob body 304a can include one or more slits 426a or breakable lines as shown in FIG. 11A for accommodating a broader range of dimensional tolerances of the bone pin 600 or 700. The knob 304 can have irregularly shaped geometry 314 for providing a secure grip surface and optionally a hexagonally shaped geometry 316 that interfaces with a wrench.

The variable position shaft or shaft 306 includes an elongated body with a through-bore extending longitudinally along its length and dimensioned for receiving a fixation element, such as a bone pin 600 or 700, an end portion including a stopper or an enlarged structure or structures, such as head 318, which operatively interacts with at least a portion of an internal surface of one of said upper and lower jaws, such as jaws 302a and 302b, for preventing the shaft 306 from passing completely through the clamp body 302 or through the jaw 302a or 302b, which the stopper 318 first comes in contact with, and a locking or engagement feature such as threads 322 on the external surface of the shaft 306, and one or more breakable lines or slits 324 on an opposing end portion of the shaft. The slits 324 can also be disposed on the stopper 318 to provide similar compression onto the bone pin 600 or 700 during locking as shown in alternative embodiments of this invention. The tapered internal surface 304*e* of the knob body 304*a* and the interaction of the engagement features such as the threads 322 and 350 guide and releasably compress the slit end 324 of the shaft 306 to provide clamping of a fixation element, such as bone pin 600. In the case where no slits are provided to the end 324 of the shaft, or even if slits are provided, the end 324 of the shaft 306 can be tapered or have a funnel-like shape to match the tapered internal surface 304*e* of the knob body 304*a*. A portion of the shaft 306 or the stopper 318 can include an at least partially spherical surface to permit the shaft 306, and thus, the bone pin 600 or 700 disposed in the through-bore of the shaft 306 to orient relative to the clamp body 302, and can have at least one anti-rotation feature such as protrusion 320 adapted to sit in a key way 004 in the clamp body 302. Other anti-rotation features can be pins, recesses, splines, and the like. The shaft 306 is configured to extend through the clamp body 302 via the through-bores 000 in the upper and lower jaws 302*a* and 302*b* and into the through-bore of the knob 304 such that the stopper 318 is disposed in the clamp body 302 and at least a portion of the threads 322 of the shaft and the slit end 324 disposed inside the knob body 304*a*. The shaft threads 322 operably engage the internal threads 350 of the knob 304 in forming a threaded connection between the shaft 306 and the knob 304 to form a cannulation or reception for receiving a bone pin such as bone pin 600 of uniform diameter or bone pin 700 of varying diameter.

In operation, the tightening of the knob 304 shortens the distance between the knob 304 and the stopper 318 and thus, flexes the upper and lower jaws 302*a* and 302*b* towards each other to clamp on an external fixation element such as the first or second external fixation components 102 and 104 disposed in aperture 308. Simultaneously, the slit end 324 of the shaft 306 is pushed and guided by the tapered internal surface 304*e* of the knob body 304*a* toward the opposing end 304*c* of the knob 304 and compressed circumferentially onto the bone pin 600 or 700 at the opposing end 304*c* of the knob 304 as the slit end 324 is pushed through the smaller opening 002 at the opposing end 304*c* of the knob 304, and thus, clamping onto the bone pin 600 or 700 by interference fit.

The clamp body 302 can include an annular protrusion such as a convex annular protrusion 312 disposed adjacent to the through-bore of the upper jaw 302*a* for operably engaging with the clamp body facing end 304*b* of the knob 304 for secure engagement. The annular protrusion 312 can have engagement features on its external convex surface to lock angularly with other engagement features on an underside of the clamp body facing end 304*b* of the knob 304.

FIGS. 11-15 illustrate an alternative embodiment 400 of the closed-end clamp system 300. The open-end clamp device 400 is similar in design to the closed-end clamp device 300 except that the groove or aperture 408 is disposed adjacent to the open end 402*c* of the clamp body 402. The outer edges of the sides of the groove or aperture 408 along its length are chamfered to allow the clamp system 400 to easily snap onto a fixation element such as fixation components 102 and 104. The knob 404 has an under surface 428 having a rough surface such as a radial interdigitation pattern operably engaging a convex protrusion 412 having a rough surface such as circular steps disposed adjacent to the through-bore in the upper jaw 402*a*.

FIGS. 15A-15D illustrate an alternative embodiment 2600 of the open-end clamp system 400. The open-end clamp system 2600 comprises a clamp body 2602, a knob 2604 and a shaft 2606. The clamp body 2602 having an open end 2602*c* and a close or hinged end 2602*d* connecting an upper jaw 2602*a* to a lower jaw 2602*b* forming a groove or aperture 2608 for receiving an external fixation element such as the first or second external fixation components 102 and 104, and a slot or spacing 2610 in communication with the aperture 2608. The upper and lower jaws 2602*a* and 2602*b* have through-bores 2000*a* and 2000*b* formed in at least partial alignment and dimensioned for receiving at least a portion of a locking element or assembly, such as the illustrated assembly comprising the knob 2604 and the shaft 2606. One of the through-bores 2000*a* and 2000*b* of the upper and lower jaws 2602*a* and 2602*b*, such as through-bore 2000*b*, defines a first diameter D1 and a second diameter D2, wherein D1 is smaller and located closer to the slot 2610. The inner surface 2602*e* containing D1 and D2 is shown as partially spherical, but it can be conical, partially conical or frusto-conical, or faceted. The inner surface 2602*e* is configured and dimensioned to operatively interact with an external surface of a slit portion of the shaft 2606 to clamp onto a fixation element, such as bone pin 600 or 700, received in a through-bore formed along a length of the shaft 2606.

The knob 2604 comprises a longitudinally formed through-bore having an internal thread and dimensioned for receiving and operatively interacting with the shaft 2606. Other engagement features, such as tabs and fins, can be used in place of or in addition to the thread on the internal surface of the knob 2604. The opposing end 2604*c* of the knob body 2604 can include one or more slits, such as slits 426*a* as shown in FIG. 11A for accommodating a broader range of dimensional tolerances of the bone pin 600 or 700. The knob 2604 can have an external surface and/or shape for providing a secure grip surface and optionally a hexagonally shaped geometry that interfaces with a wrench.

The variable position shaft or shaft 2606 includes an elongated body with a through-bore extending longitudinally along its length and dimensioned for receiving a fixation element, such as a bone pin 600 or 700, a locking or engagement feature such as threads 2622 on the external surface of the shaft 2606, and a stopper or an enlarged structure, such as head 2618, formed with one or more slits 2624 extending longitudinally along at least a portion of the length of the shaft 2606, and operatively interacting with at least a portion of an inner surface of one of said upper and lower jaws, such as inner surface 2602*e*, for compressing the slit stopper 2618 to clamp onto the bone pin 600 or 700. The inner surface 2602*e* also, but not necessary, prevents the shaft 2606 from passing completely through the clamp body 2602, or through at least one of the jaws 2602*a* or 2602*b* which the stopper 2618 first comes in contact with, such as the jaw 2602*b*. Other features and designs on the inner surface of the clamp body 2602, or of any of its upper and lower jaws that operatively interact with at least a portion of the shaft 2606 to prevent the shaft 2606 from passing completely through are still within the spirit and scope of the present invention. The stopper 2618 has a partially spherical external shape and at least one anti-rotation feature, such as anti-rotation pin 2620 configured to mate with a feature, such as a key way, on an inner surface of the clamp body 2602. Other anti-rotation features can be splines, recesses, protrusions or the like. Other shapes including conical and faceted external shapes of the stopper are considered within the spirit and scope of the present invention. The through-bore of the shaft 2606 and the width of the slit 2624 are dimensioned to receive a fixation element, such as bone pin 600 or 700, with very little play between the shaft 2606 and the bone pin 600 in an uncompressed state and a tight fit between the shaft 2606 and the bone pin 600 or 700 in a compressed state. The shaft 2606 can comprise a tapered end. The engagement feature 2622 on the external surface of the shaft 2606 can have other forms such as fins and tabs for interacting with the corresponding engagement feature on the inner surface of the knob 2604 to form a mechanical connection for clamping the fixation components and elements. The shaft 2606 is configured to extend through the clamp body 2602 via the through-bores in the upper and lower jaws 2602a and 2602b and into the through-bore of the knob 2604 such that the stopper 2618 is disposed in the clamp body 2602 and at least a portion of the threads 2622 of the shaft is disposed and operatively interacts with the threads on the inner surface of the knob 2604a.

FIGS. 16-17 and 17A describe an alternate embodiment 500 of the open-end clamp system 400. The open-end clamp system 500 is of a modular type. The open-end clamp system 500 is similar to the open-end clamp system 400 except that the convex annular protrusion 512 being a two-piece insert made of a separate upper part 504 and a separate lower part 506, and each of the parts 504 and 506 being formed with two key ways matching the key ways on the inner surfaces of the through-bores in the upper and lower jaws 502a and 502b of the clamp body 502 for receiving the anti-rotation features 320, or 420. The open-end clamp system 500 further includes a separate clip or insert 508 disposed between the upper and lower jaws 502a and 502b of the clamp body 502 for modifying the space therein. The insert 508 including an upper jaw jacket 508a connected to a lower jaw jacket 508b to form an insert groove 518 for laterally receiving a fixation element such as fixation components 102 or 104. A through-bore is formed in each of said upper and lower jaw jackets 508a and 508b of the insert 508 and aligned with aligned through-bores formed in the upper and lower jaws 502a and 502b of the clamp body 502 for receiving the convex annular protrusion insert 512. The insert 508 includes a slot or spacing between said jaw jackets 508a and 508b and in communication with said insert groove 518 to allow the upper and lower jaws 502a and 502b of the clamp body 502 and the jaw jackets 508a and 508b of the insert 508 to flex during locking and unlocking of the clamp system 500. The insert 508 is configured to have an outer cross-sectional shape (FIG. 17A) being substantially the same as an inner cross-sectional shape of the clamp body 502 to allow the insert 508 to easily slide into the space between the upper and lower jaws 502a and 502b of the clamp body 502 and mate or attach to the inner surface of the clamp body 502. The insert groove 518 can include splines to help secure gripping onto the fixation element.

Although the foregoing exemplary embodiments describe clamping systems having upper and lower jaws joined together by a hinged or closed end, the clamping systems of various embodiments of the present invention can comprise two or pairs of two separate upper and lower jaws spaced apart via a flexible structure, such as a spring coil surrounding a fastener, such as shaft 306, extending through the through-bores in the upper and lower jaws of the clamp to form one or more grooves for receiving external fixation elements such as rods, bars, pins, and a slot between the upper and lower jaws to allow the jaws to flex during locking and unlocking.

Figure 18:
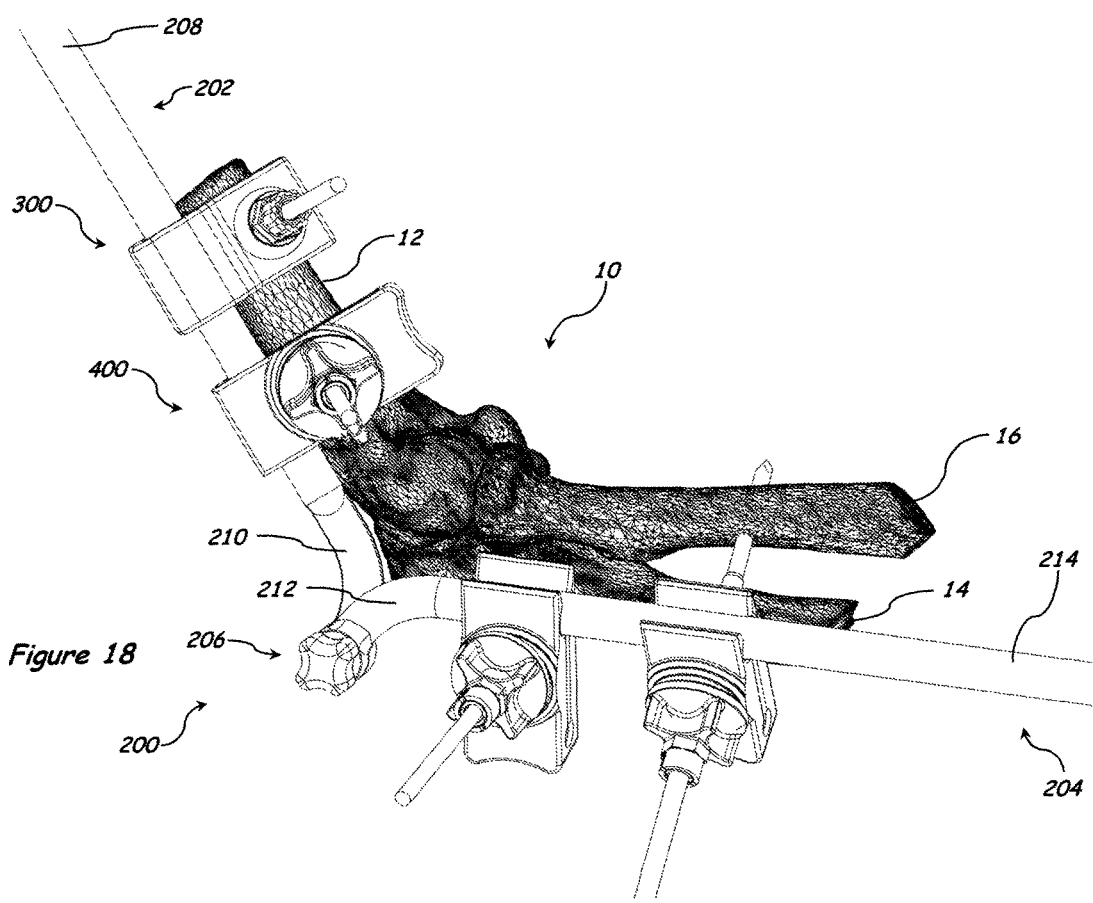
FIG. 18 is a lateral perspective view of an elbow with a second embodiment of the elbow external fixator and its associated clamps.
Figure 19:
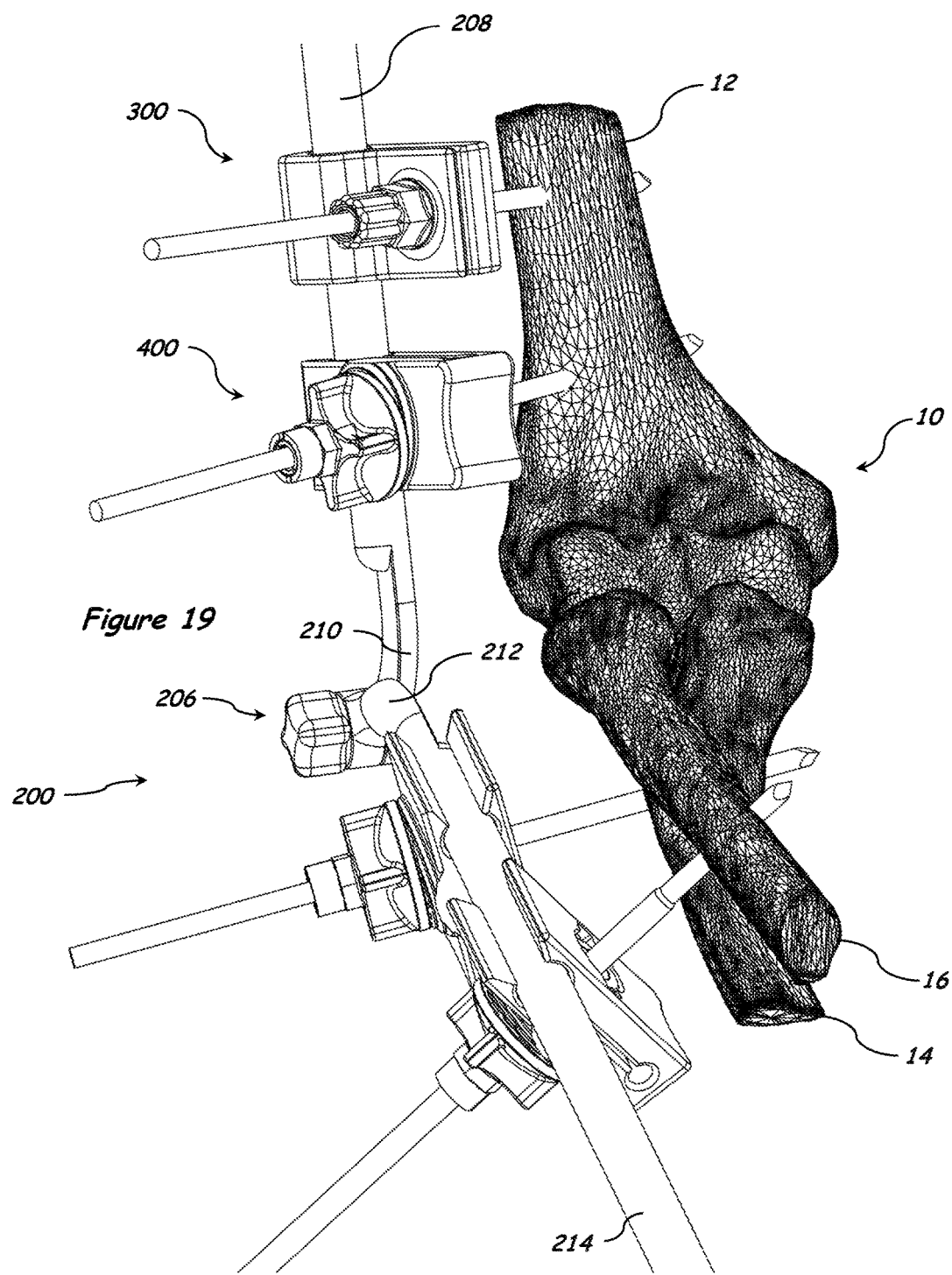
FIG. 19 is a superior-lateral perspective view of an elbow with the second embodiment of the elbow external fixator and its associated clamps.
Figure 20:
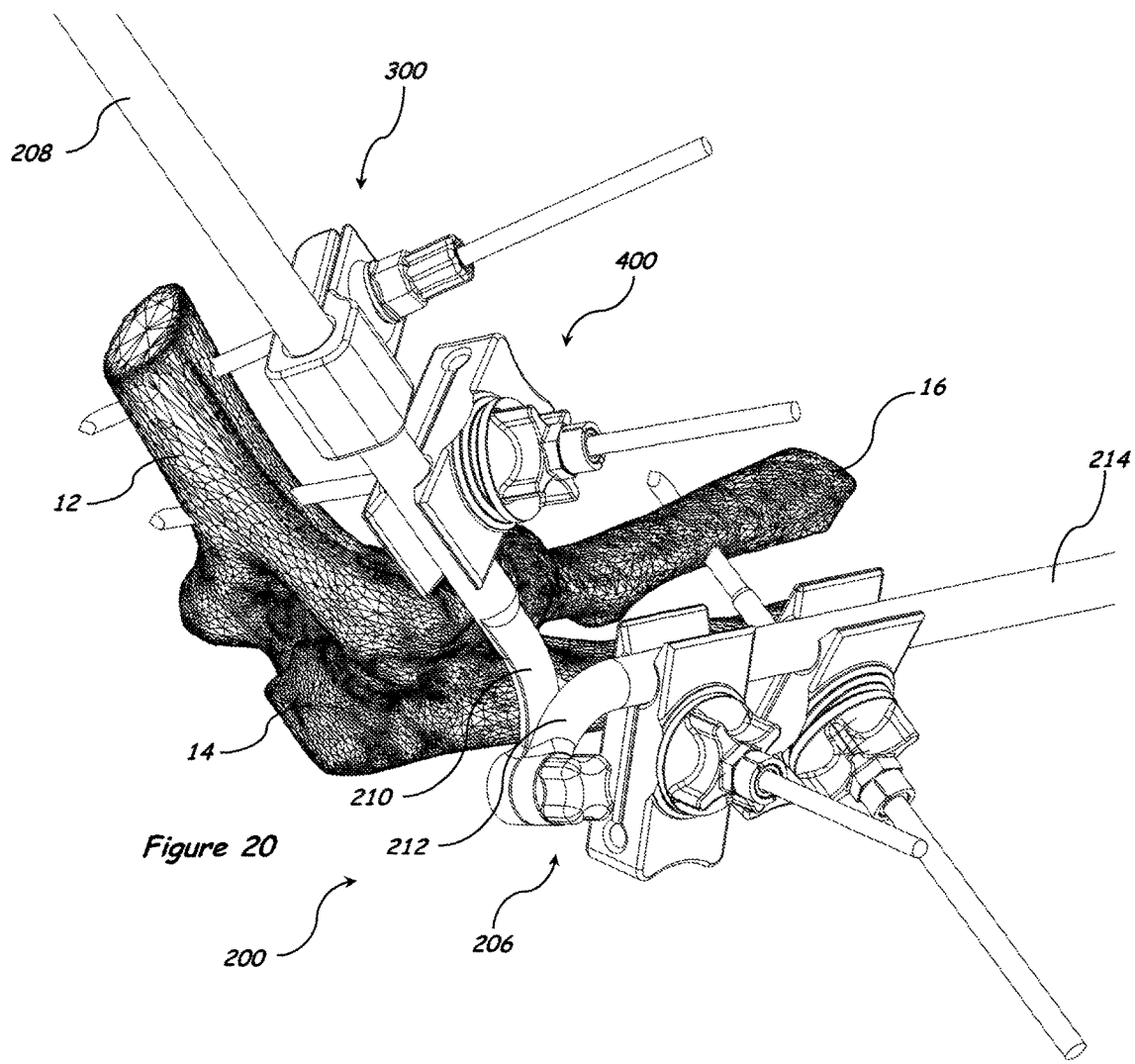
FIG. 20 is a posterior-lateral perspective view of an elbow with the second embodiment of the elbow external fixator and its associated clamps.

FIGS. 18-20 show an exemplary embodiment of an elbow-spanning hinged external fixation system 200 using the external fixator system including the novel clamp devices of the present invention. The system 200 is coupled to a human elbow 10 comprising a humerus 12, ulna 14, and radius 16. FIGS. 21-22 show exploded views of the hinge or articulator of the system 200.

Now referring to FIGS. 18-22, the elbow-spanning hinged external fixation system 200 comprising a first external fixation component 202, a second external fixation component 204, a fastener 206, a closed-end clamp system 300 and an open-end clamp system 400. The first external fixation component 202 can be adapted to attach to the humerus 12, the ulna 14 and/or the radius 16 by use of the closed-end clamp system 300 and/or open-end clamp system 400 and fixation elements such as bone pins. The second external fixation component 204 can be adapted to attach to the humerus 12, the ulna 14 and/or the radius 16 by use of the closed-end clamp system 300 and/or open-end clamp system 400.

The first external fixation component 202, second external fixation component 204, fastener 206, closed-end clamp system 300 and open-end clamp system 400 can be formed of any suitable material known to one skilled in the art that provides an adequate stiffness or resistance to torsion, stress, torque and/or other forces that may be applied to the system 200, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form a first external fixation component, a second external fixation component, a fastener, a closed-end clamp system and an open-end clamp system of aluminum, stainless steel and/or carbon fiber, at least because these materials have properties that are well suited to external fixation of fractures.

In the illustrated embodiment 200 in FIGS. 18-22, the first external fixation component 202 comprises a first component proximal (e.g., first) end 208 having a straight portion with circular cross-sectional shape (FIG. 21A) and a first component distal (e.g., second) end 210 comprising a curved portion with a semi-circular cross-sectional shape (FIG. 21B) formed with a first pivot structure 222 having a circular cross-sectional shape (FIG. 22A), and a through-bore with an internal thread 232 and a rough end surface 224. The first component proximal end 208 can be straight or curved. The second external fixation component 204 comprises a straight portion of cylindrical structure and a curved portion with semi-circular cross-sectional shape (FIG. 21B), a second component distal (e.g., first) end 214 and a second component proximal (e.g., second) end 212 comprising the curved portion formed with a second pivot structure 226 having a circular cross-sectional shape (FIG. 22A), a through-bore with no internal threads and a rough end surface 228. The second component distal end 214 can be straight or curved. Each of the first and second external fixation components 202 and 204 including their respective pivot structures 222 and 226 can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy). A fastener 206 having threads on its shaft 220 is configured to extend through the through-bore in the cylindrical pivot structure 226 of the second external fixation component 204 and the through-bore in the cylindrical pivot structure 222 of the first external fixation component 202, and forms a threaded connection with the cylindrical pivot structure 222. The first external fixation component 202 and second external fixation component 204 are attached to each other via the fastener 206 to form a movable hinge or joint 230. This movable hinge or joint 230 is then fixed in position by further tightening the fastener 206 which then interlocks the rough end surface 224 of the first pivot structure 222 with the rough end surface 228 of the second pivot structure 226. Thus, the first external fixation component 202 and the second fixation component 204 are now locked in position to reduce the bone fracture. The fastener 206 can have a distal end 216 with irregularly shaped external geometry 218 to provide a secure gripping surface, and a shaft 220 with engagement features that can interface with the engagement features such as fins or threads 232 in the second external fixation component 204.

The elbow-spanning hinged external fixation system 200 uses a combination of foregoing described embodiments of novel clamp systems 300, 400, and 500 for coupling the external fixation system 200 to the bone for fixing bone injury. This novel hinged system 200 significantly reduces surgical time by providing surgeons with flexibility in using the system on either side of the joint/body without having to align the mechanical pivot axis with the natural pivot axis of the joint, and ease of locking multiple fixation elements at once with a single tightening of a knob.

Figure 23:
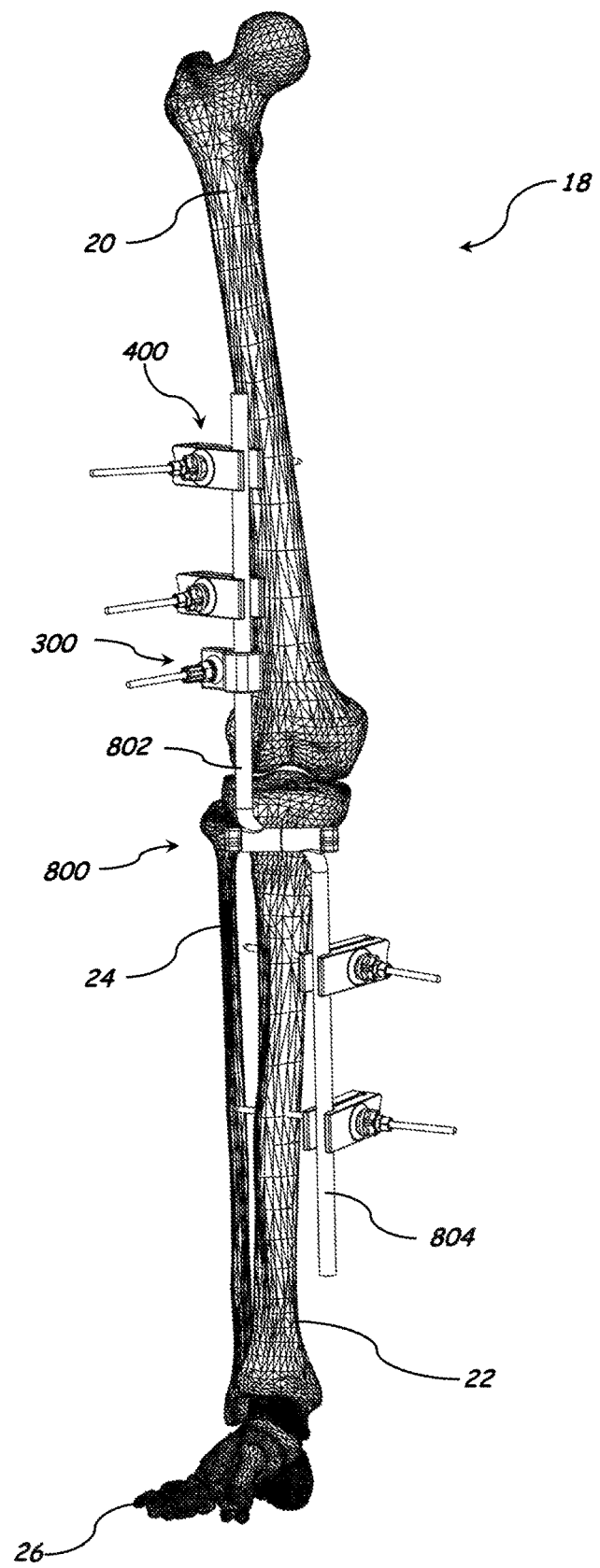
FIG. 23 is an anterior perspective view of a leg with a first embodiment of the knee external fixator and its associated clamps.
Figure 24:
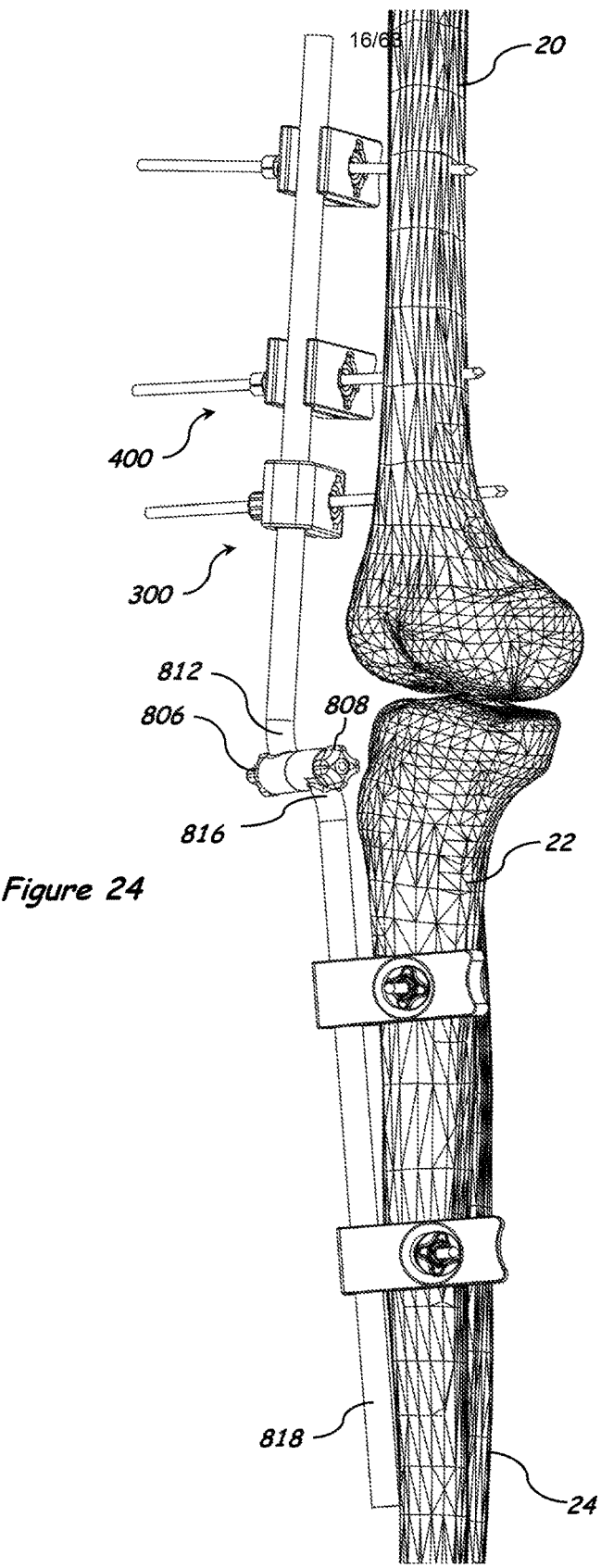
FIG. 24 is an anterior-medial perspective view of a leg with the first embodiment of the knee external fixator and its associated clamps.
Figure 25:
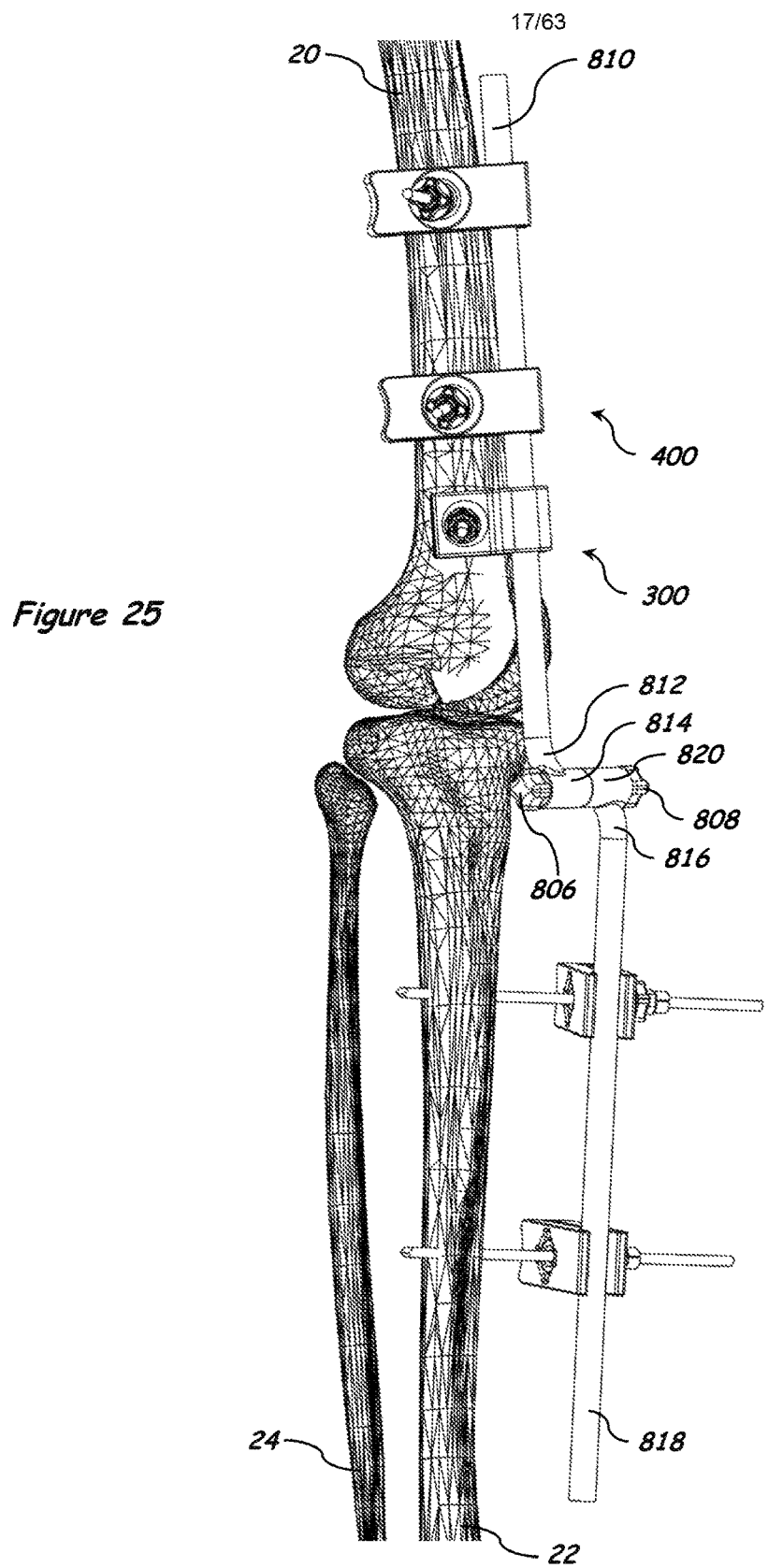
FIG. 25 is an anterior-lateral perspective view of a leg with the first embodiment of the knee external fixator and its associated clamps.
Figure 26:
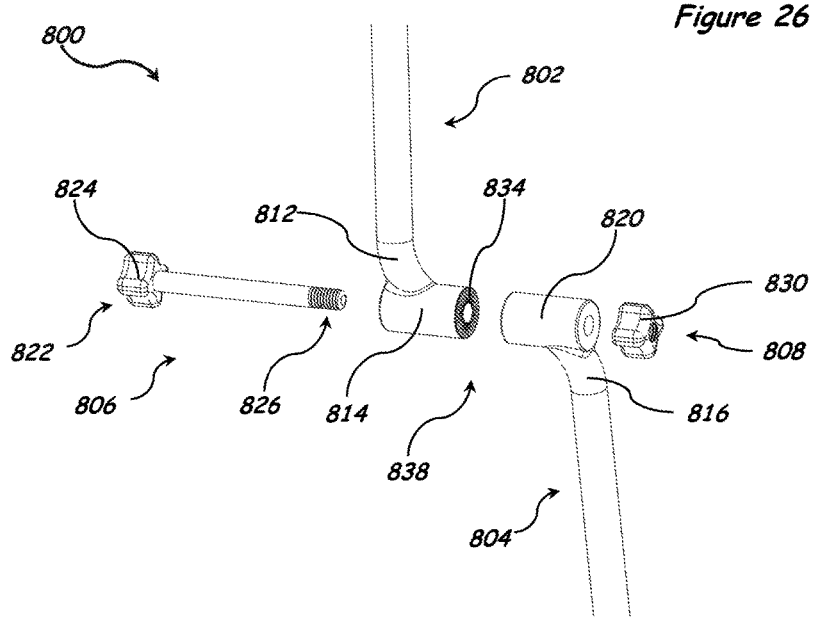
FIG. 26 is a detailed anterior-medial exploded view of the first embodiment of the knee external fixator.
Figure 27:
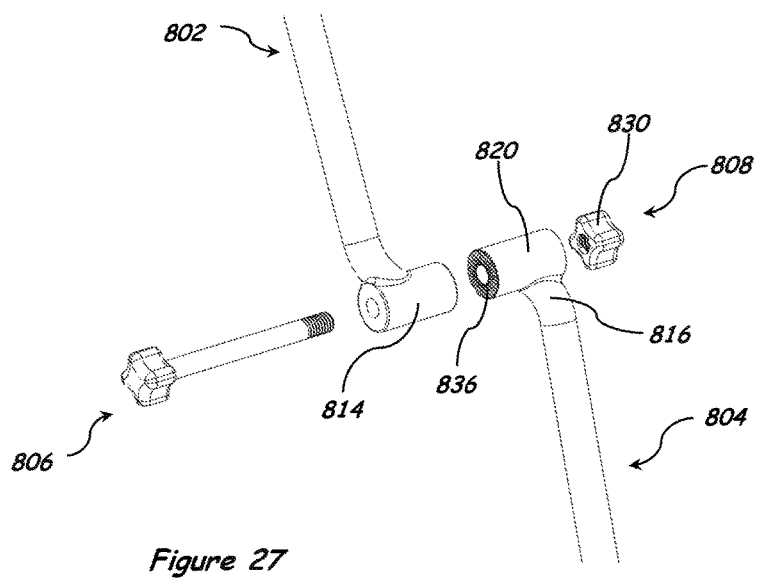
FIG. 27 is a detailed anterior-lateral exploded view of the first embodiment of the knee external fixator.
Figure 28:
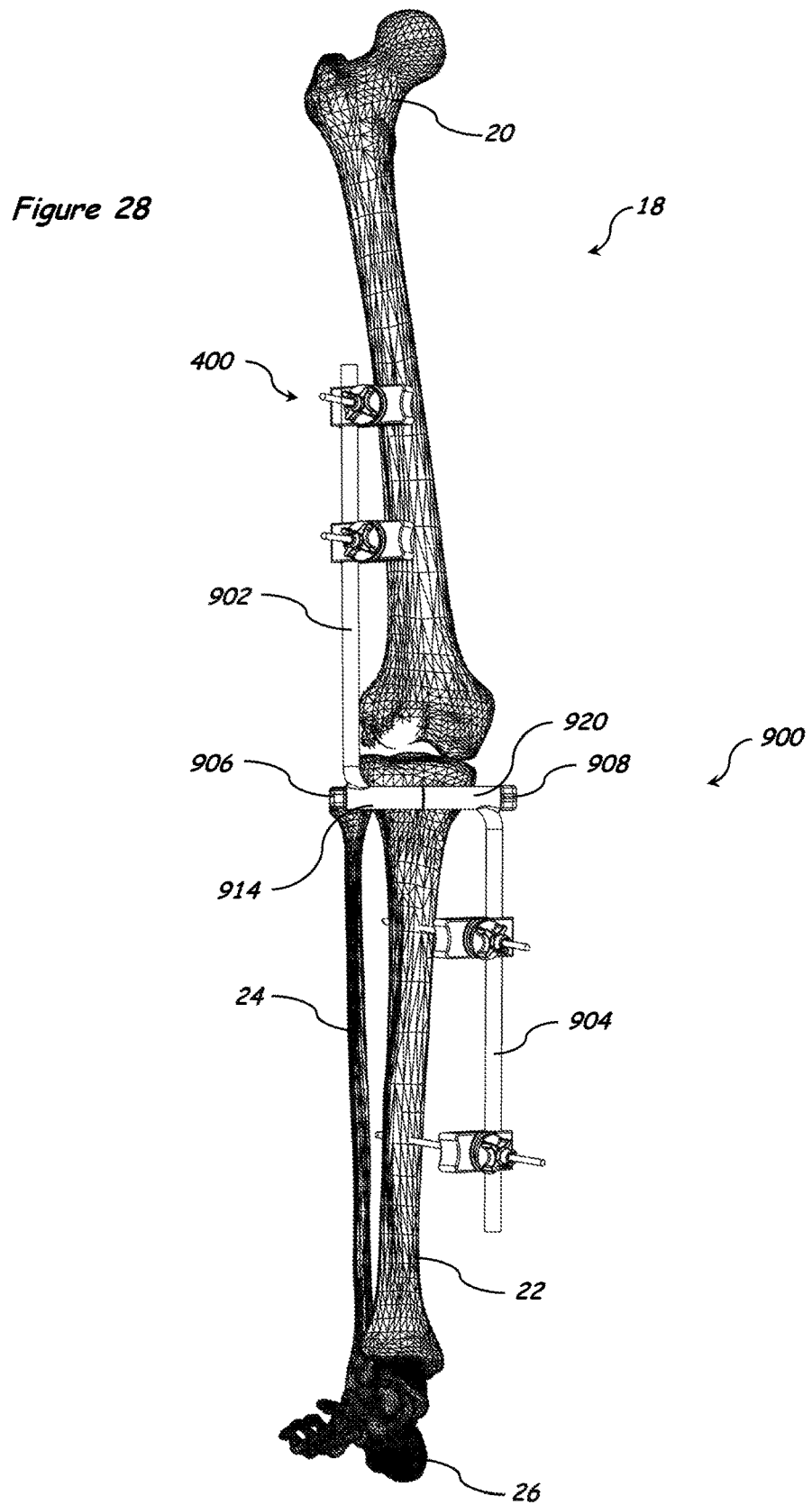
FIG. 28 is an anterior perspective view of a leg with a second embodiment of the knee external fixator and its associated clamps.
Figure 29:
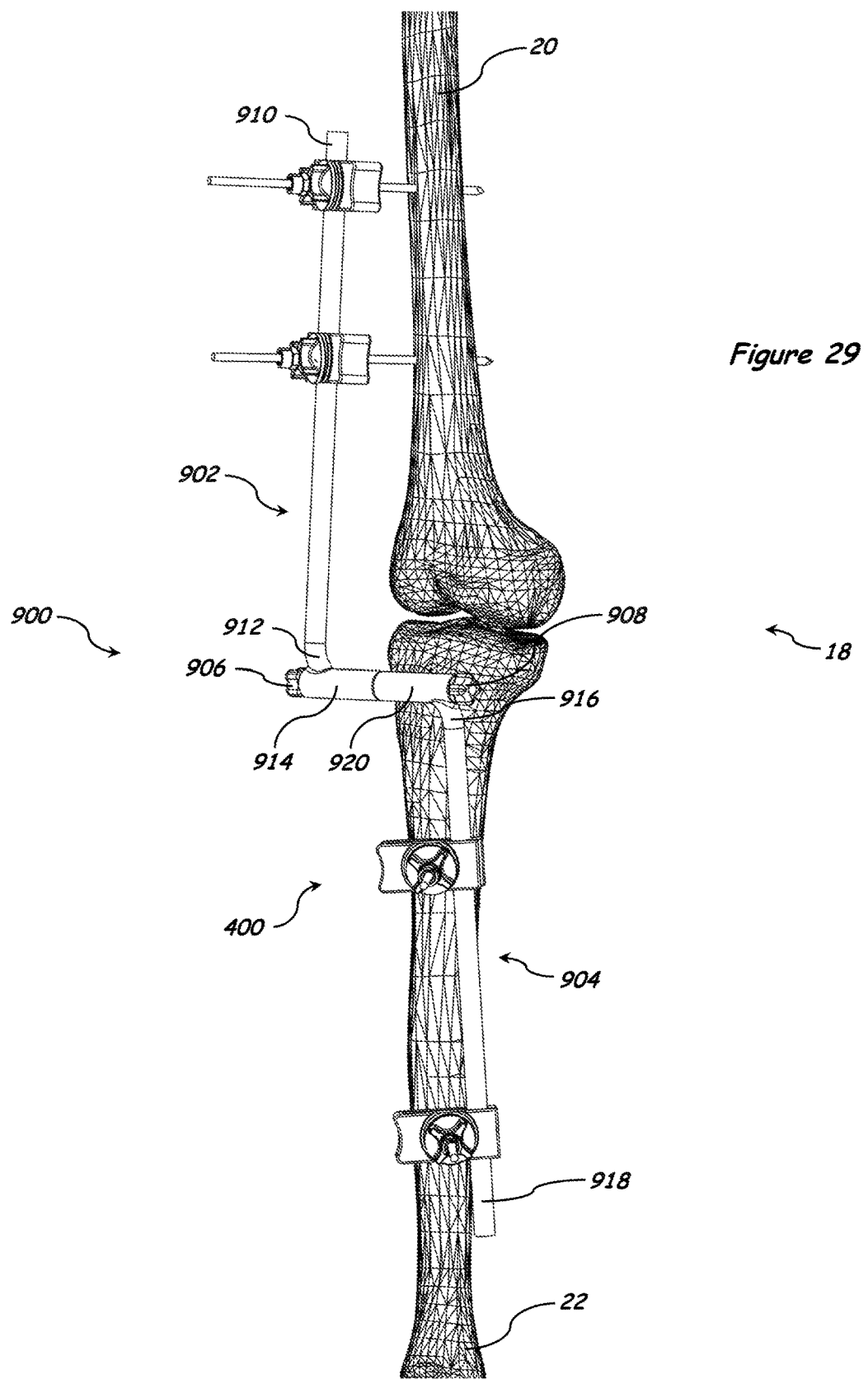
FIG. 29 is an anterior-medial perspective view of a leg with the second embodiment of the knee external fixator and its associated clamps.
Figure 30:
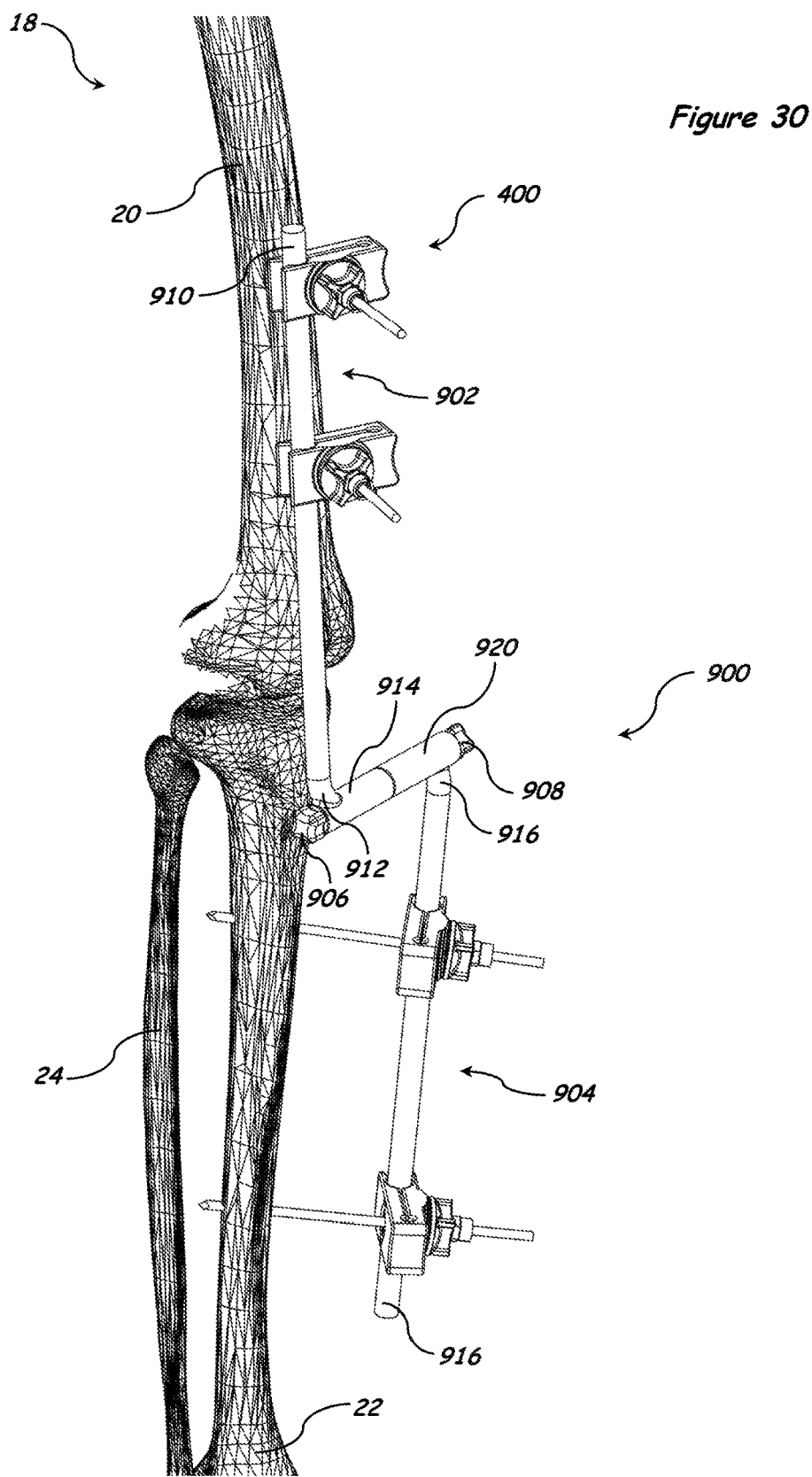
FIG. 30 is an anterior-lateral perspective view of a leg with the second embodiment of the knee external fixator and its associated clamps.
Figure 31:
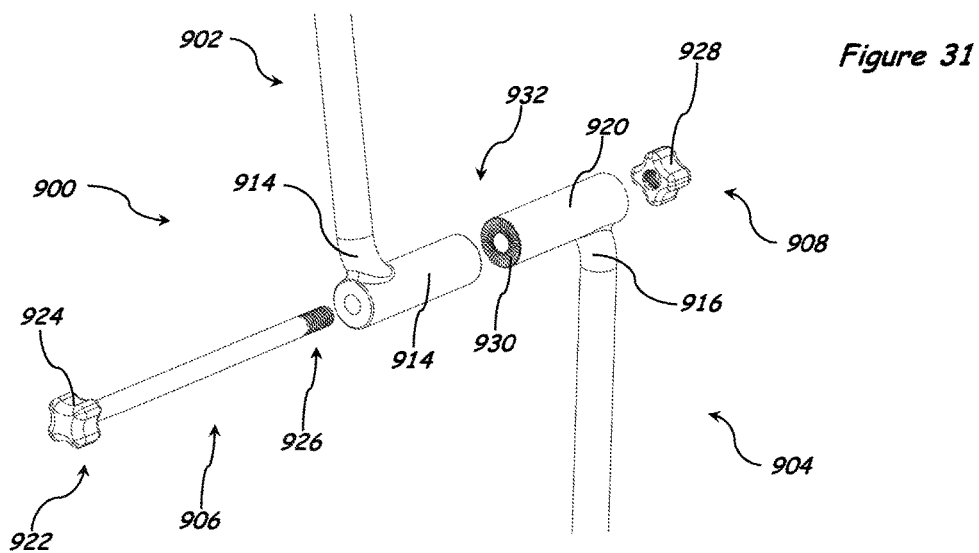
FIG. 31 is a detailed anterior-lateral exploded view of the second embodiment of the knee external fixator.
Figure 32:
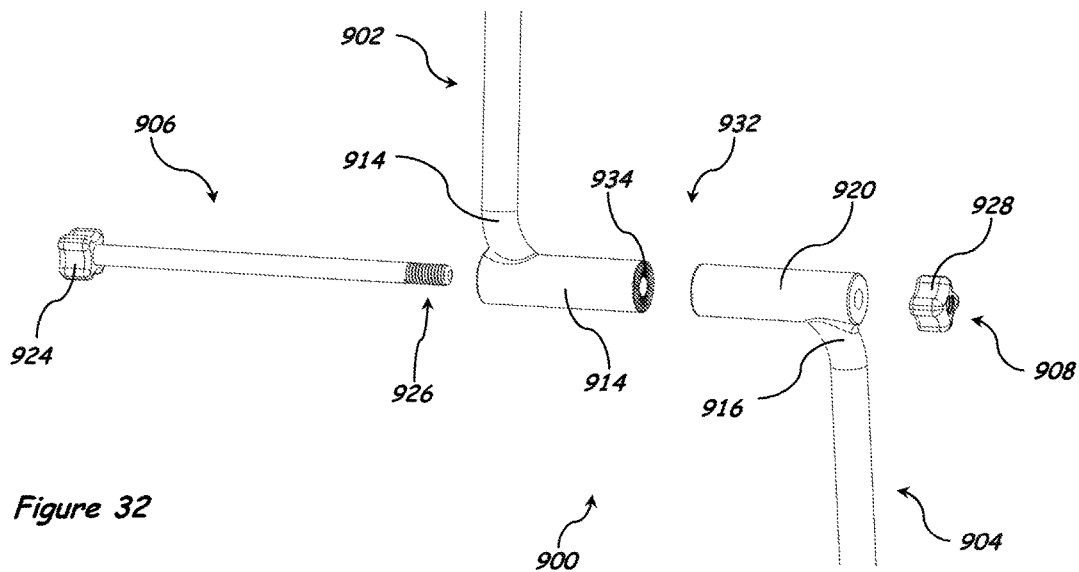
FIG. 32 is a detailed anterior-medial exploded view of the second embodiment of the knee external fixator.
Figure 33:
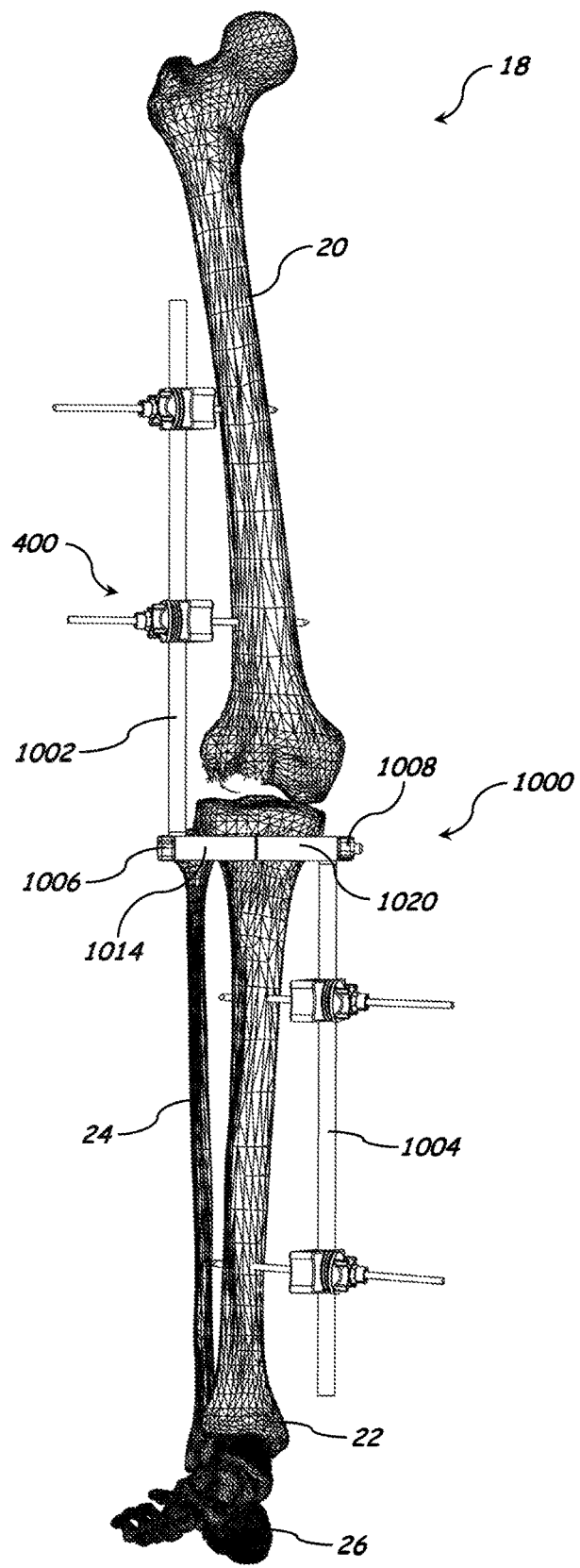
FIG. 33 is an anterior perspective view of a leg with a third embodiment of the knee external fixator and its associated clamps.
Figure 34:
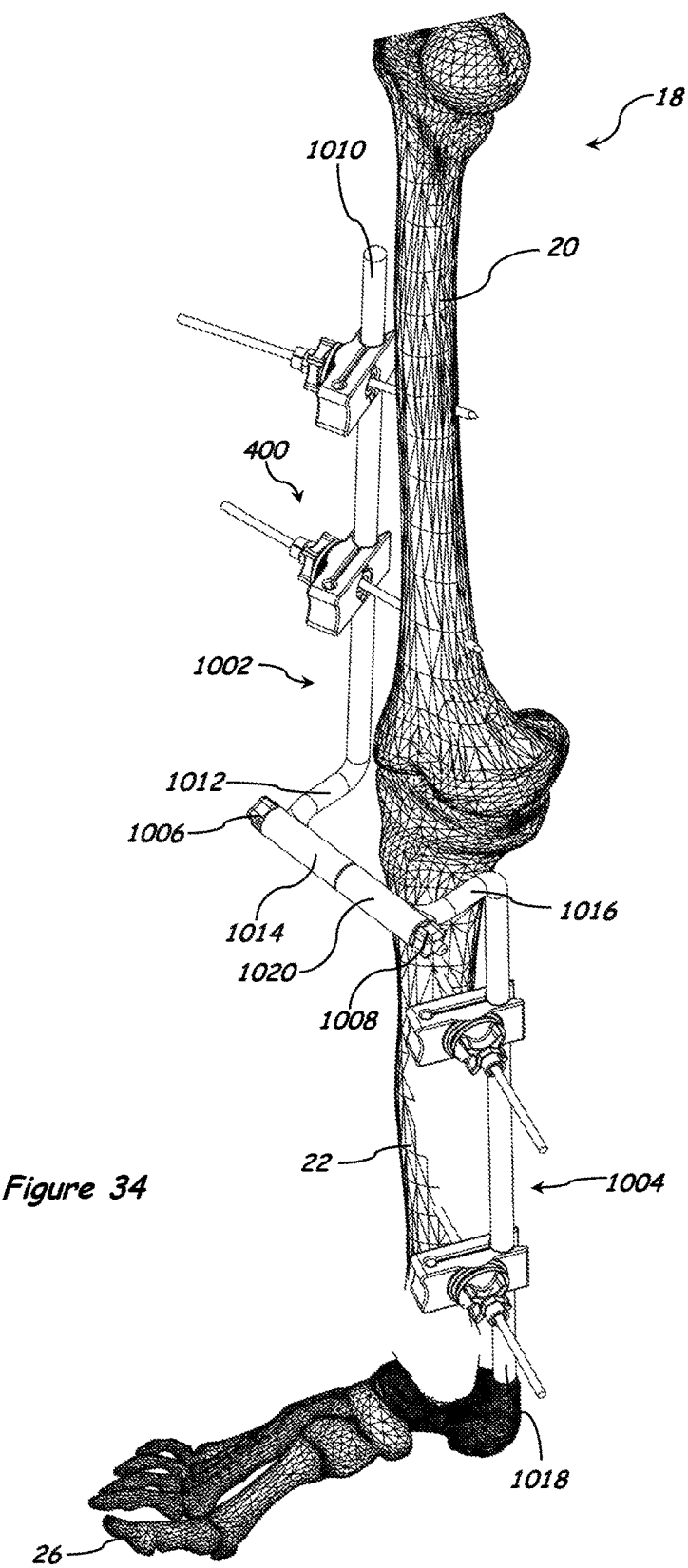
FIG. 34 is a superior-medial perspective view of a leg with the third embodiment of the knee external fixator and its associated clamps.
Figure 35:
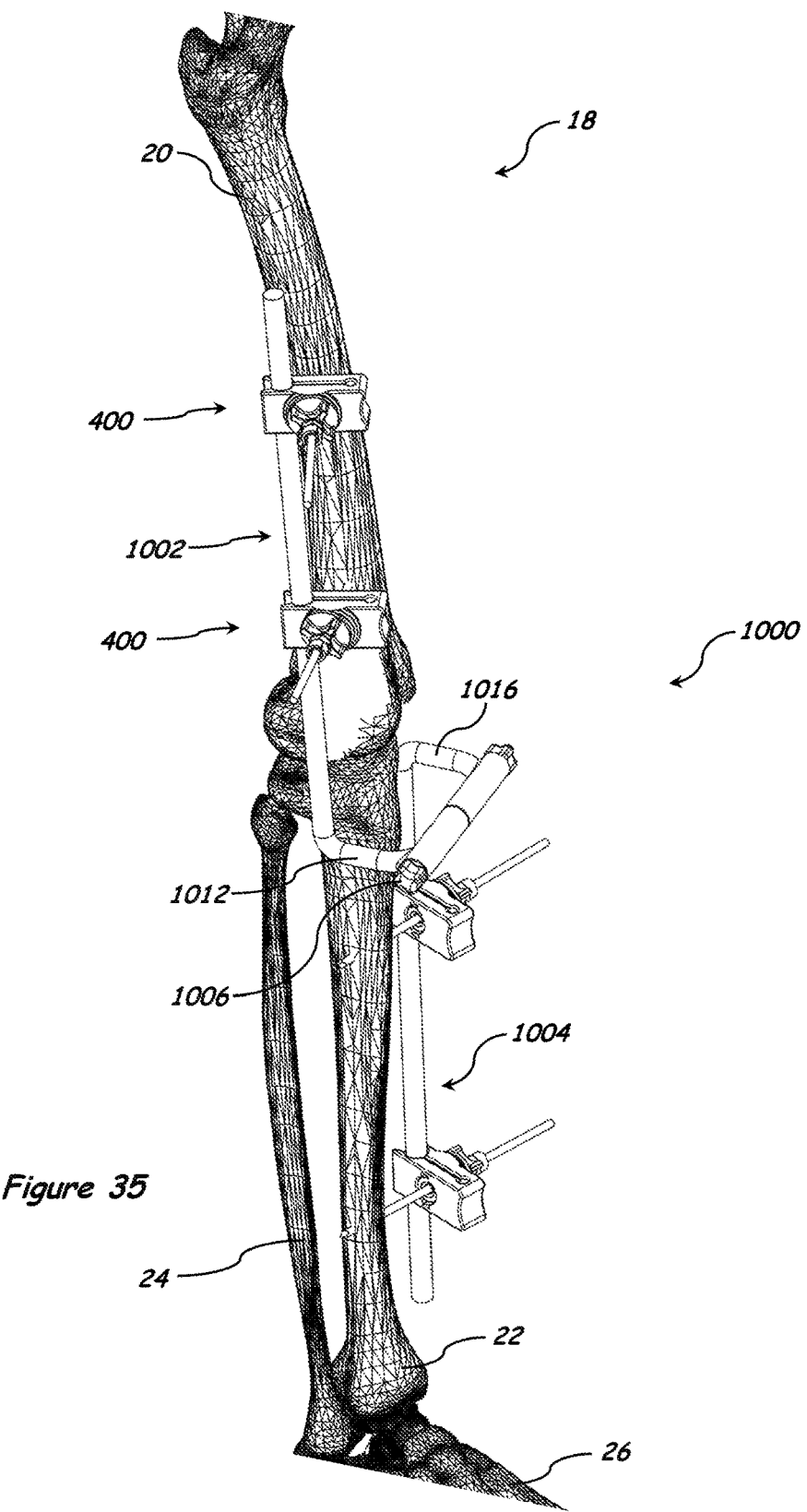
FIG. 35 is a superior-lateral perspective view of a leg with the third embodiment of the knee external fixator and its associated clamps.
Figure 36:
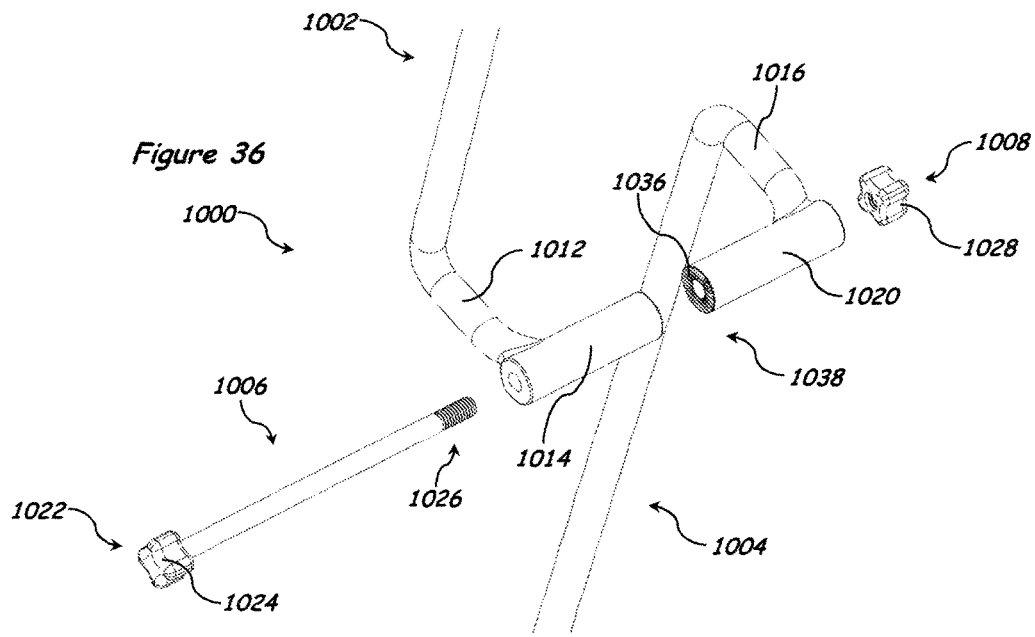
FIG. 36 is a detailed superior-lateral exploded view of the third embodiment of the knee external fixator.
Figure 37:
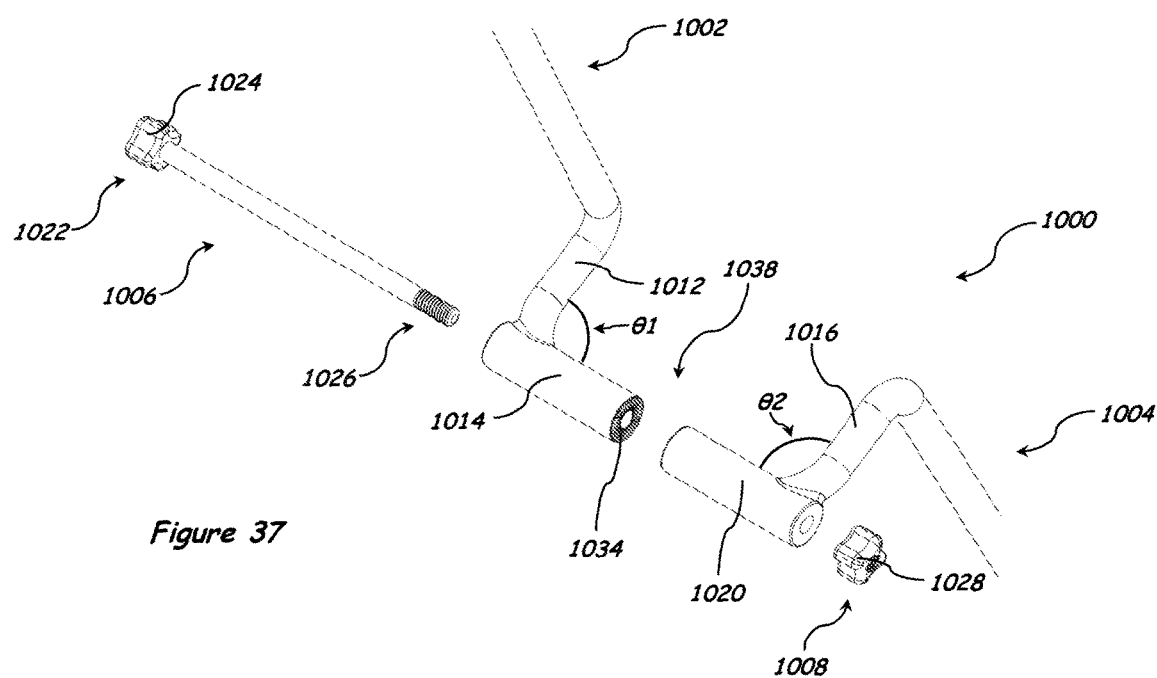
FIG. 37 is a detailed superior-medial exploded view of the third embodiment of the knee external fixator.

Referring now to FIGS. 23-25, a first embodiment of an exemplary knee-spanning external fixation system 800 is illustrated mounted on a lower extremity 18 comprising a femur 20, tibia 22, fibula 24 and a foot 26.

FIGS. 23-27 illustrate a first embodiment of an exemplary knee-spanning external fixation system 800 comprising a first external fixation component 802, a second external fixation component 804, a first fastener 806, a second fastener 808, a closed-end clamp system 300 and an open-end clamp system 400. The first external fixation component 802 can be adapted to couple to the femur 20, the tibia 22, the fibula 24 and/or the foot 26 by use of the closed-end clamp system 300 and/or open-end clamp system 400. The second external fixation component 804 can be adapted to attach to the femur 20, the tibia 22, the fibula 24 and/or the foot 26 by use of the closed-end clamp system 300 and/or open-end clamp system 400.

The first external fixation component 802, second external fixation component 804, first fastener 806, second fastener 808, closed-end clamp system 300 and open-end clamp system 400 can be formed of any suitable material known to one skilled in the art that provides an adequate stiffness or resistance to torsion, stress, torque and/or other forces that may be applied to the system 800, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form a first external fixation component, a second external fixation component, a fastener, a closed-end clamp system and an open-end clamp system of aluminum, stainless steel and/or carbon fiber, at least because these materials have properties that are well suited to external fixation of fractures.

In the illustrated embodiment 800 in FIGS. 23-27, the first external fixation component 802 comprises a straight portion of cylindrical structure and a curved portion also of cylindrical structure, a first component proximal (e.g., first) end 810 and a first component distal (e.g., second) end 812 comprising the curved portion formed with a pivot structure of cylindrical body 814 having a through-bore bound by smooth walls extending along its pivot axis and further having a rough end surface 834. The first component proximal end 810 can be straight or curved. The second external fixation component 804 comprises a straight portion of cylindrical structure and a curved portion also of cylindrical structure, a second component distal (e.g., first) end 818 and a second component proximal (e.g., second) end 816 comprising the curved portion formed with a pivot structure of cylindrical body 820 having a through-bore bound by smooth walls extending along its pivot axis and a rough end surface 836. The second component distal end 818 can be straight or curved. The pivot structures 814 and 820 each has a length along the pivot axis such that when the two pivot structures 814 and 820 are joined end to end at their rough surfaces by a fastener, such as 806 or 808, the first external fixation component 802 and the second external fixation component 804 are disposed on different sides of the bone or knee (e.g., right side, left side, anterior, posterior). Each of the first and second external fixation components 802 and 804 including their respective pivot structures 814 and 820 can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy). A fastener 806 having threads 826 on its shaft is configured to extend through the through-bore in the cylindrical pivot structure 814 of the first external fixation component 802 and the through-bore in the cylindrical pivot structure 820 of the second external fixation component 804 and into a second fastener such as a threaded nut 808, and forms a threaded connection with the nut 808. The first external fixation component 802 and second external fixation component 804 are thus attached to each other via the coupling and interactions of the pivot structures 814 and 820 and the fasteners 806 and 808 to form a movable hinge or joint 838. This movable hinge or joint 838 is then locked in position by further tightening the fasteners 806 and 808 which interlocks the rough end surface 834 of the first external fixation component 802 with the rough end surface 836 of the second external fixation component 804. The fastener 806 can have a distal end or head 822 with irregularly shaped external geometry 824 to provide a secure gripping surface, and a shaft with engagement features such as threads 826 that can interface with the engagement features such as fins or threads inside the second fastener 808. Similarly, the second fastener 808 can also have an outer surface geometry for secure gripping surface.

FIGS. 28-32 illustrate an alternative embodiment 900 of the exemplary knee-spanning external fixation system 800 comprising a first external fixation component 902, a second external fixation component 904, a first fastener 906, a second fastener 908 and an open-end clamp system 400. The first external fixation component 902 can be adapted to attach to the femur 20, the tibia 22, the fibula 24 and/or the foot 26 by use of the closed-end clamp system 300 and/or open-end clamp system 400. The second external fixation component 904 can be adapted to attach to the femur 20, the tibia 22, the fibula 24 and/or the foot 26 by use of a closed-end clamp system 300 and/or open-end clamp system 400.

The exemplary knee-spanning external fixation system 900 is similar to the foregoing described system 800 except that the lockable and movable hinge of the knee-spanning external fixation system 900 is dimensioned to accommodate a wider joint or bone size. This is made possible by designing the pivot structures 914 and 920 to have a longer length along their mechanical pivot axis for accommodating a broader range of pin sites and/or body or joint sizes.

FIGS. 33-37 show a third embodiment of an exemplary knee-spanning external fixation system 1000 for mounting on a lower extremity 18 comprising a femur 20, tibia 22, fibula 24 and a foot 26.

The third embodiment of an exemplary knee-spanning external fixation system 1000 comprises a first external fixation component 1002, a second external fixation component 1004, a first fastener 1006, a second fastener 1008 and an open-end clamp system 400 or a close-end clamp system 300. The first external fixation component 1002 can be adapted to couple to the femur 20, the tibia 22, the fibula 24 and/or the foot 26 by use of the closed-end clamp system 300 and/or open-end clamp system 400. The second external fixation component 1004 can be adapted to couple to the femur 20, the tibia 22, the fibula 24 and/or the foot 26 by use of a closed-end clamp system 300 and/or open-end clamp system 400.

The first external fixation component 1002, second external fixation component 1004, first fastener 1006, second fastener 1008 and open-end clamp system 400 and optionally close-end clamp system 300 can be formed of any suitable material known to one skilled in the art that provides an adequate stiffness or resistance to torsion, stress, torque and/or other forces that may be applied to the system 1000, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form a first external fixation component, a second external fixation component, a fastener, a closed-end clamp system and an open-end clamp system of aluminum, stainless steel and/or carbon fiber, at least because these materials have properties that are well suited to external fixation of fractures.

In the illustrated embodiment 1000 in FIGS. 33-37, the first external fixation component 1002 having an "L" shape and a circular cross-sectional shape, comprises a first component proximal (e.g., first) end portion 1010 and a first component distal (e.g., second) end portion 1012. The first component distal end portion 1012 comprises the shorter leg of the "L" shape and is coupled to or formed at its open end a pivot structure of cylindrical body 1014 having a through-bore bound by smooth walls extending along its pivot axis and a rough end surface 1034. The first component distal end portion 1012 comprises a straight middle segment connecting two curved end segments. However, these segments can all be straight or curved. The first component proximal end 1010 can be straight or curved. The second external fixation component 1004 having an inverted "L" shape, comprises a second component proximal (e.g., second) end portion 1016 and a second component distal (e.g., second) end portion 1018. The second component proximal end portion 1016 comprises the shorter leg of the inverted "L" shape and is coupled to, or formed at, its open end a pivot structure of cylindrical body 1020 having a through-bore bound by smooth walls extending along its pivot axis and a rough end surface 1036. The second component proximal end portion 1016 comprises a straight middle segment connecting two curved end segments. However, these segments can all be straight or curved. The second component distal end portion 1018 can be straight or curved. The pivot structures 1014 and 1020 each has a length along the pivot axis such that when the two pivot structures 1014 and 1020 are joined end to end at their rough surfaces 1034 and 1036 by a fastener, the first external fixation component 1002 and the second external fixation component 1004 are disposed on different sides of the bone or knee (e.g., right side, left side, anterior, posterior). Each of the first and second external fixation components 1002 and 1004 including their respective pivot structures 1014 and 1020 can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy).

A fastener 1006 having threads 1026 on its shaft is configured to extend through the through-bore in the cylindrical pivot structure 1014 of the first external fixation component 1002 and the through-bore in the cylindrical pivot structure 1020 of the second external fixation component 1004 and into a second fastener such as a threaded nut 1008, and forms a threaded connection with the nut 1008. The first external fixation component 1002 and second external fixation component 1004 are thus attached to each other via fasteners 1006 and 1008 to form a movable hinge or joint 1038. This movable hinge or joint 1038 is then locked in position by further tightening the fasteners 1006 and 1008 which interlocks the rough end surface 1034 of the pivot structure 1014 with the rough end surface 1036 of the pivot structure 1020. The fastener 1006 can have a distal end or head 1022 with irregularly shaped external geometry 1024 to provide a secure gripping surface, and a shaft with engagement features such as threads 1026 that can interface with the engagement features such as fins or threads inside the second fastener 1008. Similarly, the second fastener 1008 can also have an outer surface geometry for secure gripping surface.

In this exemplary embodiment, the first component distal end portion 1012 and the second component proximal end portion 1016 form a right angle with their respective first component proximal end portion 1010 and second component distal end portion 1018. One skilled in the art can select other angles such as 60 or 120 degrees to accommodate the type of fracture or body shape, for example. Other shapes and dimensions of the first and second external fixation components 1002 and 1004 also are within the spirit and scope of various embodiments of the present invention. Similarly, the angles ($\theta 1$, $\theta 2$) between the pivot structures 1014 and 1020 and their respective first component distal end portion 1012 and second component proximal end portion 1016 are 90 degrees as schematically illustrated in FIGS. 33-37, but angles other than 90 degrees are contemplated and within the spirit and scope of various embodiments of the present invention.

The first external fixation component 1002 and the second external fixation component 1004 including their respective pivot structures 1014 and 1020 can each be formed as a unitary modular structure or a modular structure. In the case of a unitary modular structure, for example, the first external fixation component 1002 can be formed from a single rod or bar and bent into the "L" shape, and welded to the pivot structure 1014. In the case of a modular structure, the first external fixation component 1002 and the pivot structure 1014 can be formed by removably connecting plurality of straight and/or curved rod segments and the pivot structure 1014 by snap-fitting, or threading, for example. The first and second external fixation components 1002 and 1004 and the pivot structures 1014 and 1020 can have any cross-sectional shapes (e.g. hexagonal, oval, square) and dimensions other than the circular cross-sectional shape as schematically illustrated in FIGS. 33-37.

Figure 38:
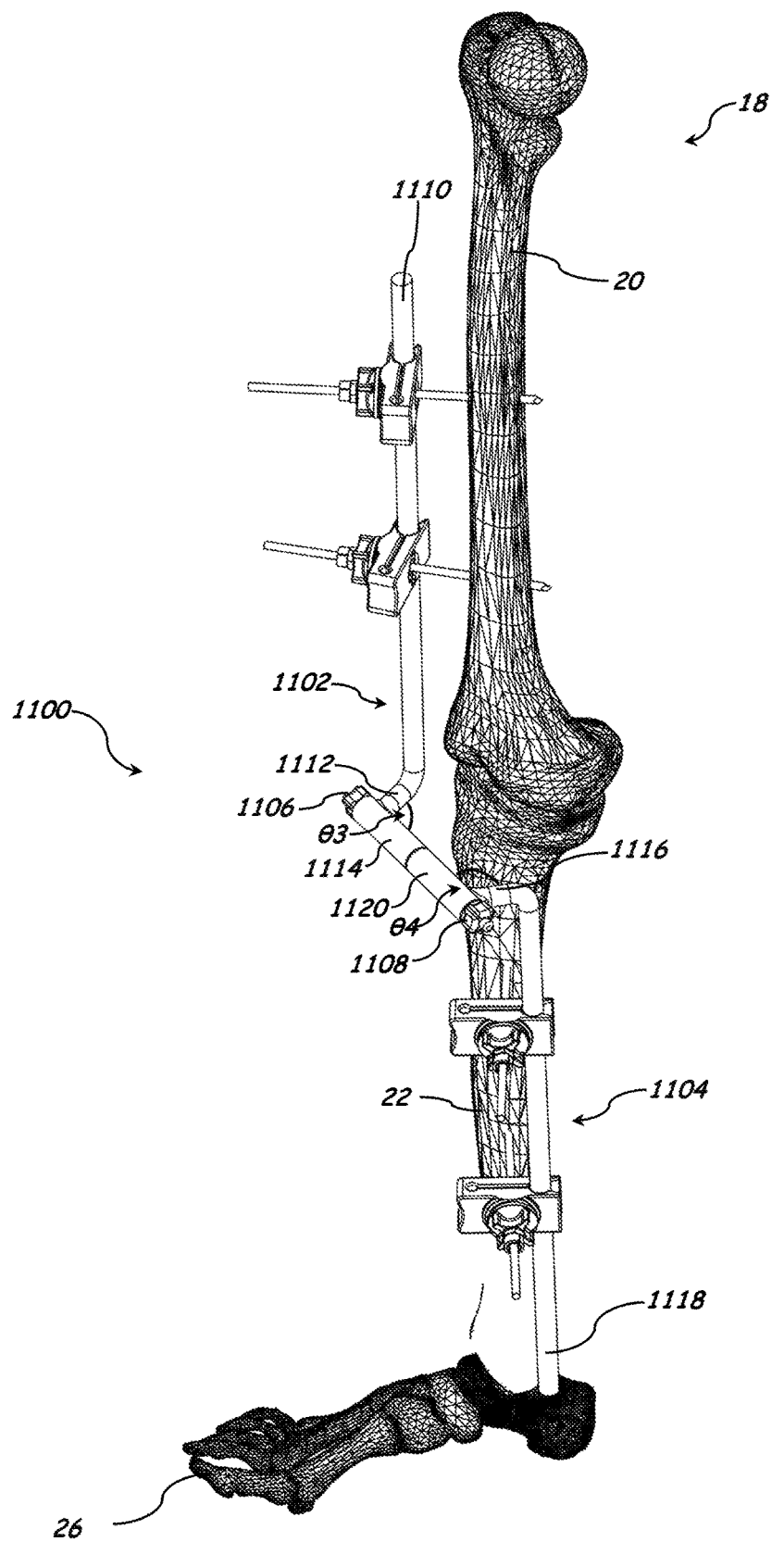
FIG. 38 is a superior-medial perspective view of a leg with a fourth embodiment of the knee external fixator and its associated clamps.
Figure 39:
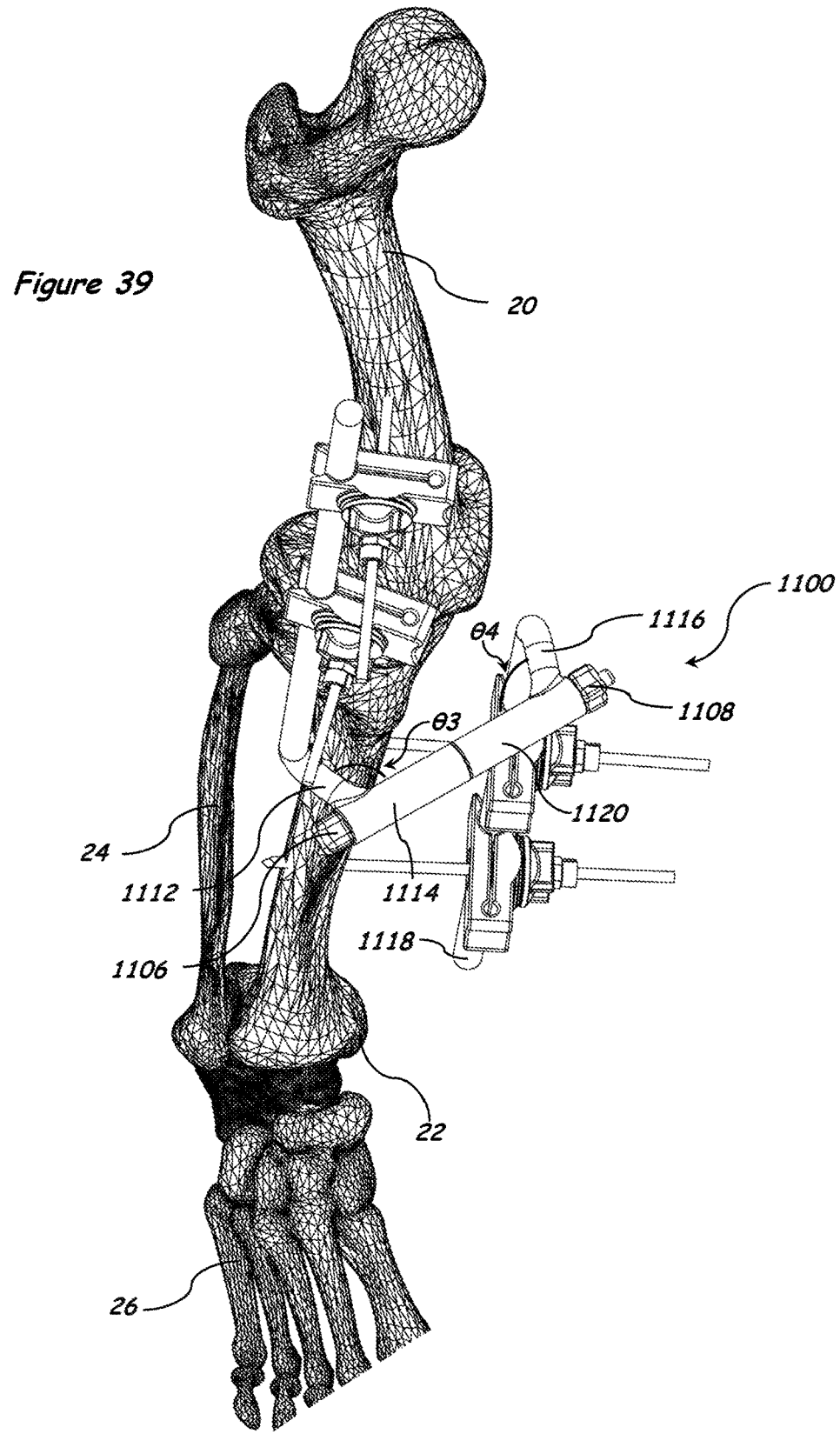
FIG. 39 is a superior-lateral perspective view of a leg with the fourth embodiment of the knee external fixator and its associated clamps.

Referring now to FIGS. 38-39, an alternative embodiment 1100 of the exemplary knee-spanning external fixation system 1000 is shown mounted by pins on the lower extremity 18 comprising a femur 20, tibia 22, fibula 24 and a foot 26.

The knee-spanning external fixation system 1100 illustrated in FIGS. 38-41 is similar to exemplary knee-spanning external fixation system 1000 in FIGS. 33-37 except that the first component distal (e.g., first) end 1112 and the second component proximal (e.g., second) end 1116 are each connected to their respective pivot structures 1114 and 1120 at an angle greater than 90 degrees (θ3, θ4).

FIGS. 42-69 show various exemplary ankle-spanning external fixation systems, some are of unitary, prefabricated modular construction (e.g. from multiple pieces welded together), or unitary construction (e.g. from a single piece of material by molding), while others are of modular construction (e.g. multiple pieces removably threaded together to allow surgeons to use the assembled system as is or to reconfigure the assembled system to match the patient anatomy). The illustrated ankle-spanning external fixation systems comprise a proximal or upper frame coupled to a distal or lower frame such as the curved foot frame including a posterior frame segment extending angularly from and above an inferior frame segment designed for placement and use substantially adjacent to the ankle area of the body to protect both the posterior and the inferior of a foot or ankle while healing is taken place. The system can be used adjacent to other joints such as the elbow or the knee, and is capable of being any shape and size that allows for support of the joint and area round the joint such as the foot, ankle, and/or lower extremity.

Figure 42:
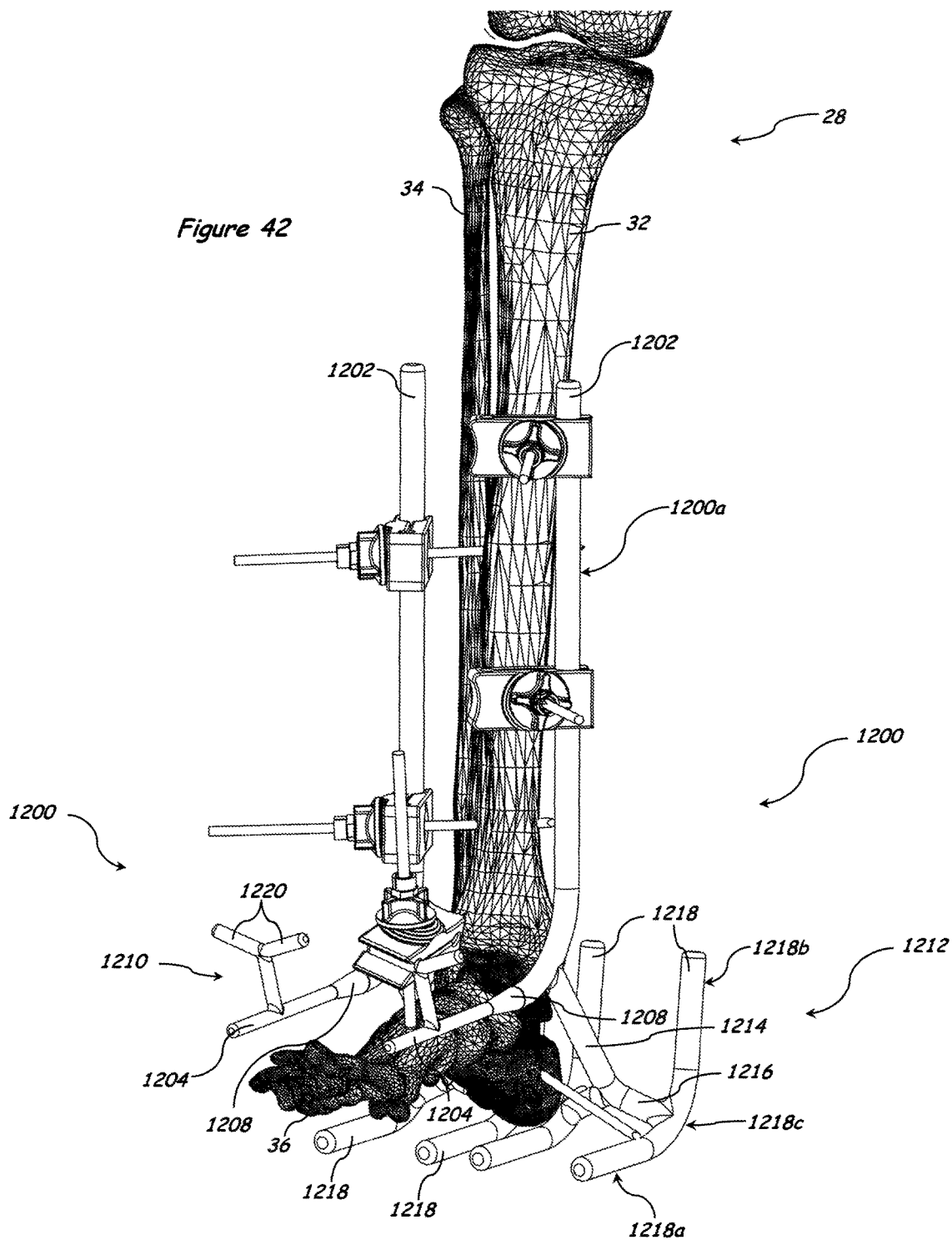
FIG. 42 is an anterior-medial perspective view of a leg with a first embodiment of the ankle external fixator and its associated clamps.
Figure 43:
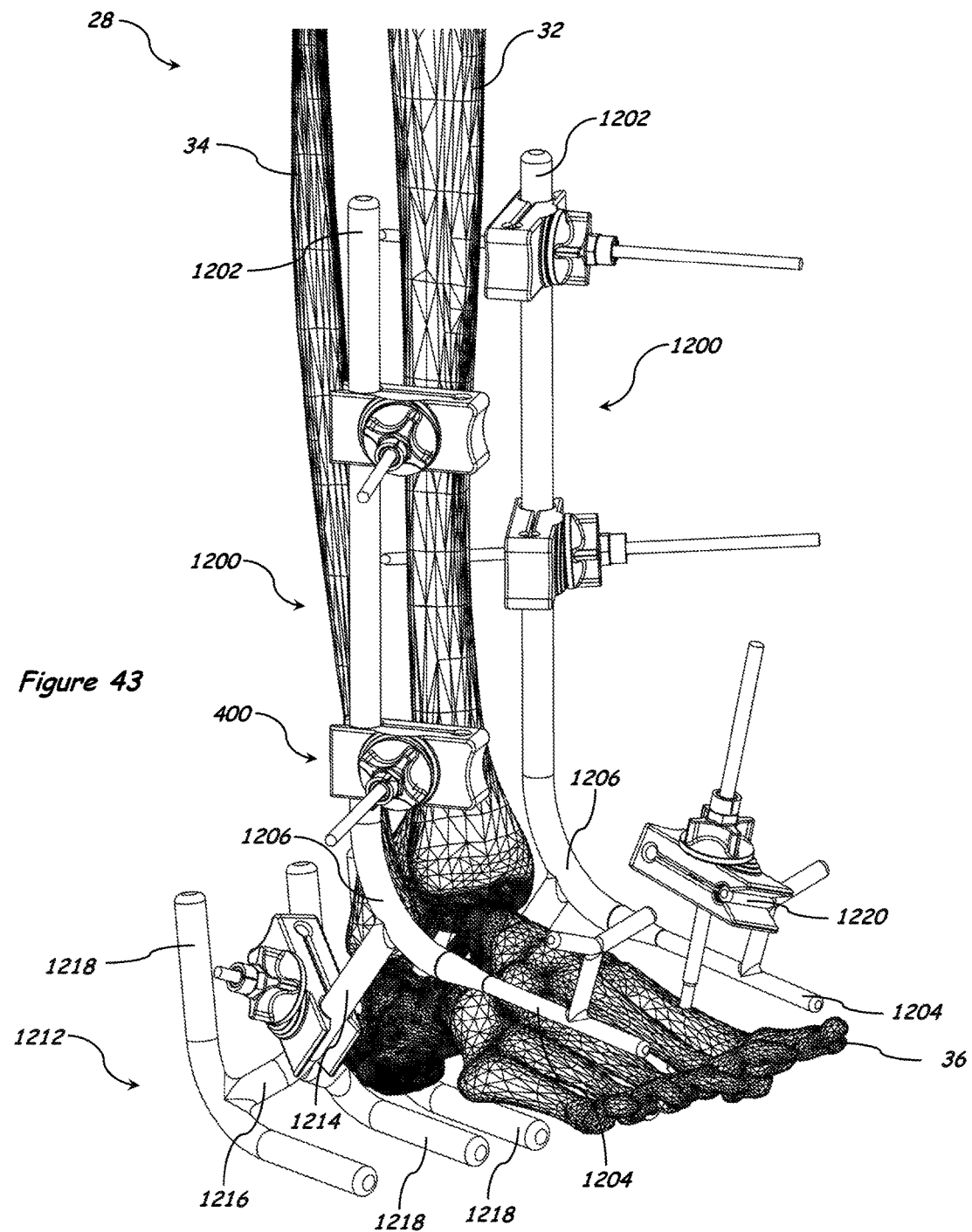
FIG. 43 is an anterior-lateral perspective view of a leg with the first embodiment of the ankle external fixator and its associated clamps.
Figure 44:
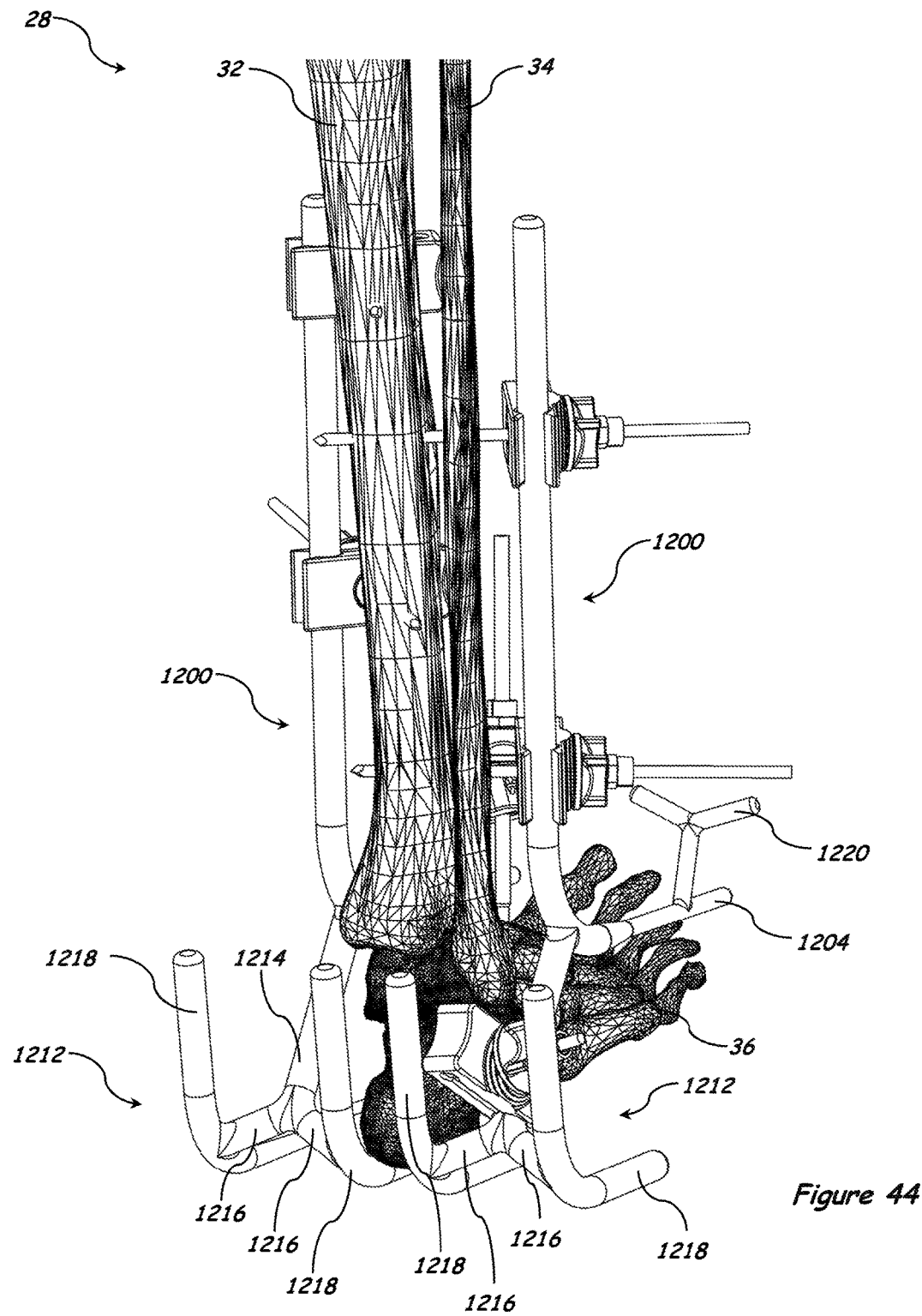
FIG. 44 is a posterior-lateral perspective view of a leg with the first embodiment of the ankle external fixator and its associated clamps.

Referring now to FIGS. 42-44, a first embodiment of an exemplary ankle-spanning external fixation system 1200 is shown mounted via pins on an exemplary lower extremity 28 comprising a tibia 32, fibula 34 and a foot 36. The fixation system 1200 includes one or more open-end clamps 400 and 1300 and optionally closed-end clamps for clamping fixation elements such as bars, rods, pins, or wires of various diameters.

The external fixation system 1200 and open-end clamp systems 400 and 1300 can be formed of any suitable material known to one skilled in the art that provides an adequate stiffness or resistance to torsion, stress, torque and/or other forces that may be applied to the system 1200, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form the system 1200 of aluminum, stainless steel and/or carbon fiber, at least because these materials have properties that are well suited to external fixation of fractures.

The illustrated embodiment 1200 in FIGS. 42-44 comprises two ankle-spanning external fixation systems 1200 which are substantially the same and mounted on each side of the foot to protect the ankle and area around the ankle. Each external fixation system 1200 comprises a single piece, unitary prefabricated modular frame comprising a proximal (e.g., first) frame 1200a, a connector 1214 and 1216 and a distal (e.g., second) frame 1212 attached together by standard means, such as welding, soldering, brazing, crimping, or adhesives. The proximal frame defines a single bar or rod such as bar 1200a including a proximal (e.g., first) end portion 1202 and a distal (e.g., second) end portion 1204 and a curved portion 1206 connecting the proximal and distal end portions 1202 and 1204. The distal end 1204 can be of a reduced diameter 1208 and comprises an extension or outrigger 1210 which can be divided into two or more branches, such as bifurcation 1220, for attaching a clamp such as the open-end clamp system 300 or closed-end clamp system 400. A distal frame, such as the foot frame 1212, configured to capture the posterior and the inferior aspects of a joint, such as the ankle, comprising two parallel curved rods 1218, is coupled to the proximal frame, such as the bar 1200a, via a Y-shaped connector having two arms 1216 and a trunk 1214. Other shapes of the connector also are within the spirit and scope of various embodiments of the present invention. Each curved rod 1218 comprises a straight inferior (e.g., first) frame section or portion 1218a and a straight posterior (e.g., second) frame section or portion 1218b and a curved frame section or portion 1218c connecting the straight inferior frame section 1218a to the straight posterior frame section 1218b, wherein said inferior frame portion 1218a and said posterior frame portion 1218b are operatively disposed in at least partially surrounding and spatial relation to the ankle or the heel of the foot 36, wherein said posterior frame portion 1218b extends angularly from and above said inferior frame portion 1218a. Each arm 1216 of the Y-shaped connector connects to one of the rods 1218 of the foot frame 1212 at the concave surface side of the curved frame section, and the trunk 1214 of the Y-shaped connector connects to the curved portion 1206 of the proximal frame such as the bar frame 1200a at the convex surface side of the curved portion 1206.

The foot frame 1212 is generally configured to capture the posterior and the inferior aspects of a foot or ankle and thus may take various shapes as illustrated in other exemplary embodiments. In the single piece, unitary modular construction, the proximal and distal frames 1200a and 1212 and connector(s) 1214 and 1216 and their subcomponents such as outrigger 1220 can be welded, soldered, crimped, brazed or glued/epoxied together during manufacturing. Alternatively, in a unitary construction, the proximal frame 1200a, the connector 1214 and 1216 and the distal frame 1212 and optionally any subcomponents such as an outrigger 1220 may be integral-machined or formed from a single piece of metal or other material by standard means such as molding or machining. In a multi-piece, or modular construction, the proximal and distal frames 1200a and 1212 and connector 1214 and 1216 and their subcomponents 1220 can be removably connected by standard means such as threads, plug-socket joint, snap-fit, interference fit or a combination thereof during manufacturing or immediately prior to use to provide surgeons the flexibility of design choices to fit the patient anatomy. The proximal and distal end portions 1202 and 1204 of the bar frame 1200a and the Y-shaped connector may be formed of various curved and/or straight pieces or subcomponents connected together and may have any profiles. The components of the system 1200 are shown as having circular cross-sectional shape. Other cross-sectional shapes such as hexagonal shape, square, rectangle, for example, are within the spirit and scope of the various embodiments of the present invention.

Figure 45:
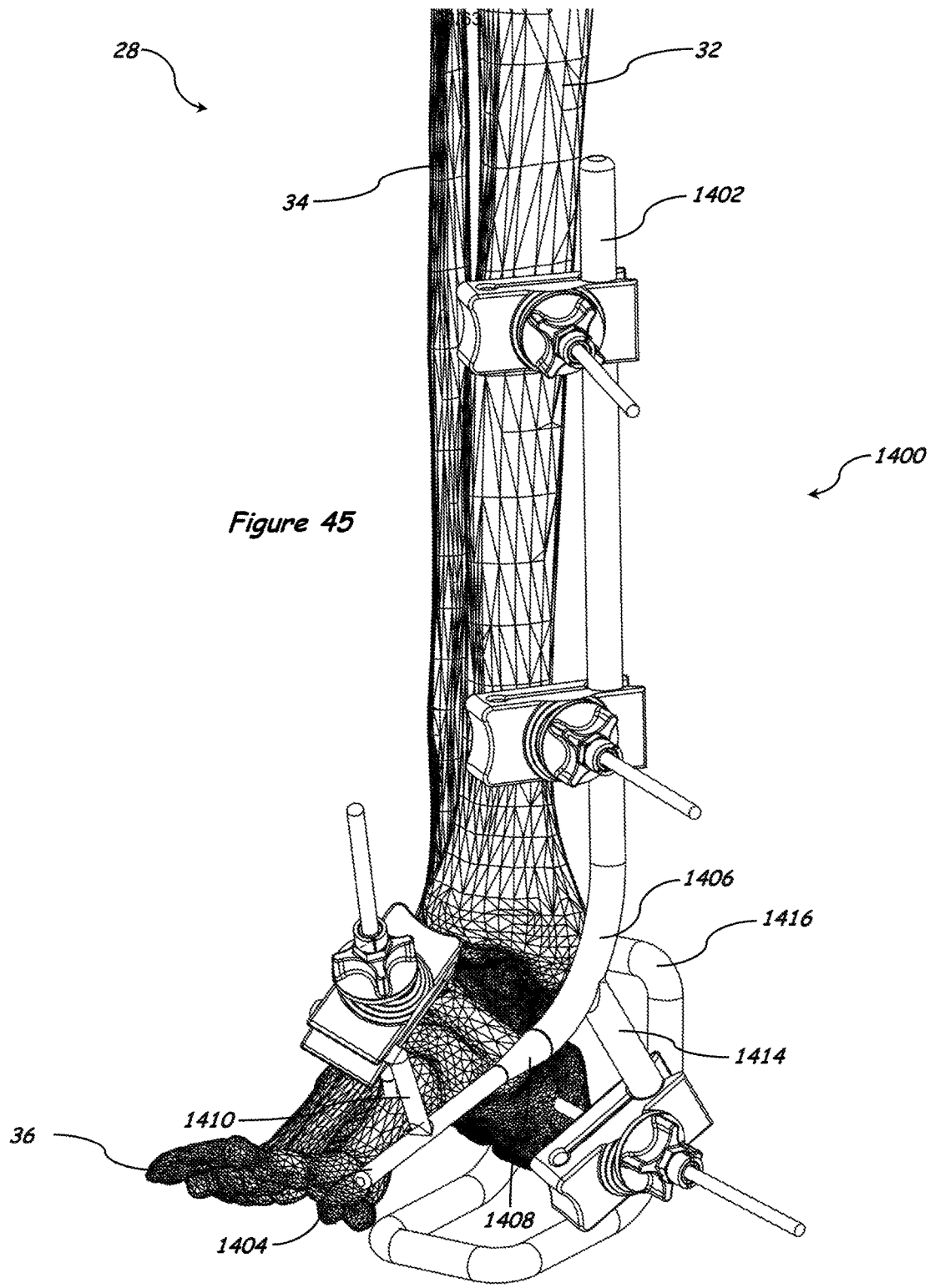
FIG. 45 is an anterior-medial perspective view of a leg with a second embodiment of the ankle external fixator and its associated clamps.
Figure 46:
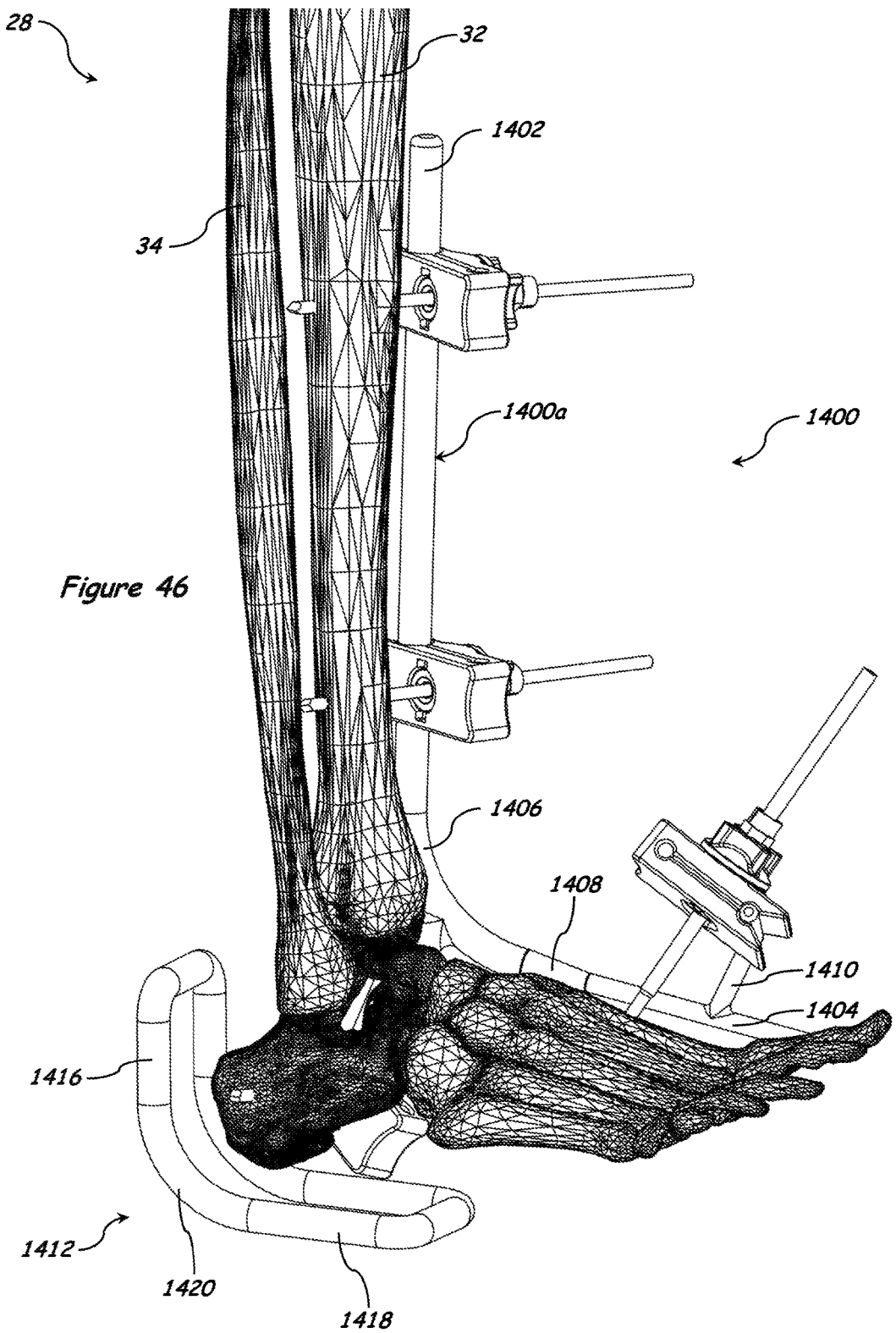
FIG. 46 is an anterior-lateral perspective view of a leg with the second embodiment of the ankle external fixator and its associated clamps.
Figure 47:
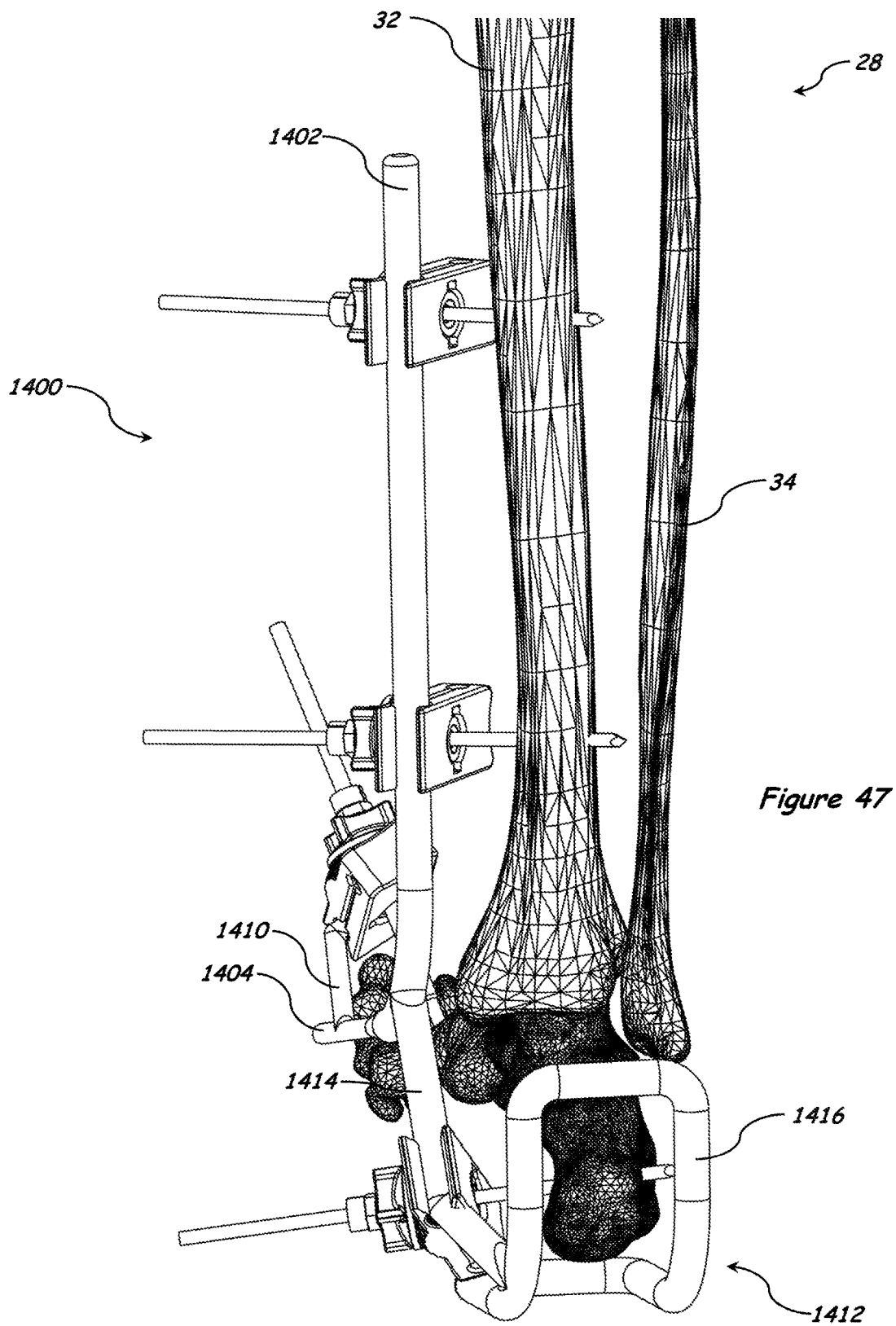
FIG. 47 is a posterior-medial perspective view of a leg with the second embodiment of the ankle external fixator and its associated clamps.

Referring now to FIGS. 45-47, an alternative embodiment 1400 of the exemplary ankle-spanning external fixation system 1200 is shown mounted by pins on the lower extremity 28 comprising a femur 30, tibia 32, fibula 34 and a foot 36, wherein the foot frame is of a different design.

The exemplary ankle-spanning external fixation system 1400 comprises a single piece, unitary prefabricated modular frame comprising a proximal (e.g., first) frame 1400a, a connector 1414 and a distal (e.g., second) frame 1412 attached together by standard means such as welding, soldering, brazing, crimping, or adhesives. Alternatively, the proximal frame, the connector and the distal frame may be integral-machined or formed from a single piece of metal or other material by standard means such as molding or machining. The exemplary ankle-spanning external fixation system 1400 comprises a proximal frame such as bar frame 1400a coupled to a distal frame such as a foot frame 1412 via a frame connector 1414 wherein the foot frame comprises a continuous elongated ring frame having a U-shaped inferior (e.g., first) frame section 1418 lying in a first plane and a U-shaped posterior (e.g., second) frame section 1416 lying in a second plane and a curved section 1420 connecting each of the legs of the U-shape inferior frame section 1418 to each of those of the U-shaped posterior frame section 1416 to form a closed loop. Other shapes of the inferior and posterior frame portions are also within the spirit and scope of various embodiments of the present invention. The first and second planes containing the inferior frame section 1418 and the posterior frame section 1416 are perpendicular to each other as schematically illustrated. However, the angle between the first and second planes can be other than 90 degrees, such as 60 degrees or 120 degrees. Said inferior frame portion 1418 and said posterior frame portion 1416 are operatively disposed in at least partially surrounding and spatial relation to the ankle or the heel of the foot 36, wherein said posterior frame portion 1416 extends angularly from and above said inferior frame portion 1418. In the single piece, unitary modular construction, the proximal and distal frames 1400a and 1412 and connector(s) 1414 and their subcomponents such as outrigger 1410 can be welded, soldered, crimped, brazed or glued/epoxied together during manufacturing. Alternatively, in a unitary construction, the proximal frame 1400a, the connector 1414 and the distal frame 1412 and optionally any subcomponents such as an outrigger 1410 may be integral-machined or formed from a single piece of metal or other material by standard means such as molding or machining. In a multi-piece, or modular construction, the proximal and distal frames 1400a and 1412 and connector 1414 and their subcomponents 1410 can be removably connected by standard means, such as threads, plug-socket joint, snap-fit, interference fit or a combination thereof during manufacturing or immediately prior to use to provide surgeons the flexibility of design choices to fit the patient anatomy. All the components of the frames and the frame connector can have circular cross-sectional shape as shown or can have other cross-sectional shape including square, oval, hexagon, or others. Each of the proximal and distal frames can be made from a single rod/bar or a plurality of straight and/or curved bar/rod segments or subcomponents connected together end-to-end using welding, soldering, gluing, brazing, crimping, threading, snap-fitting or the like.

Figure 48:
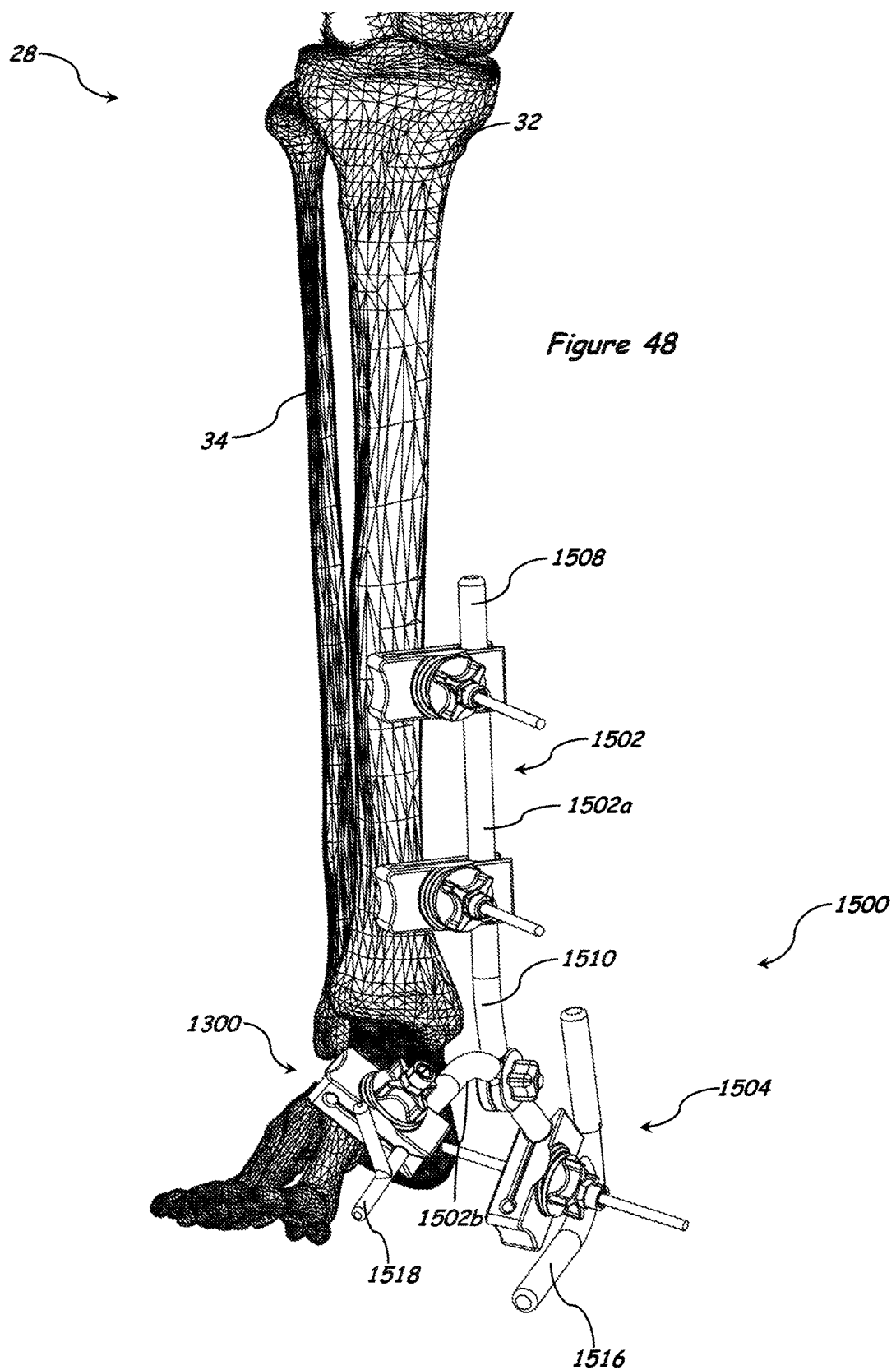
FIG. 48 is an anterior-medial perspective view of a leg with a third embodiment of the ankle external fixator and its associated clamps.
Figure 49:
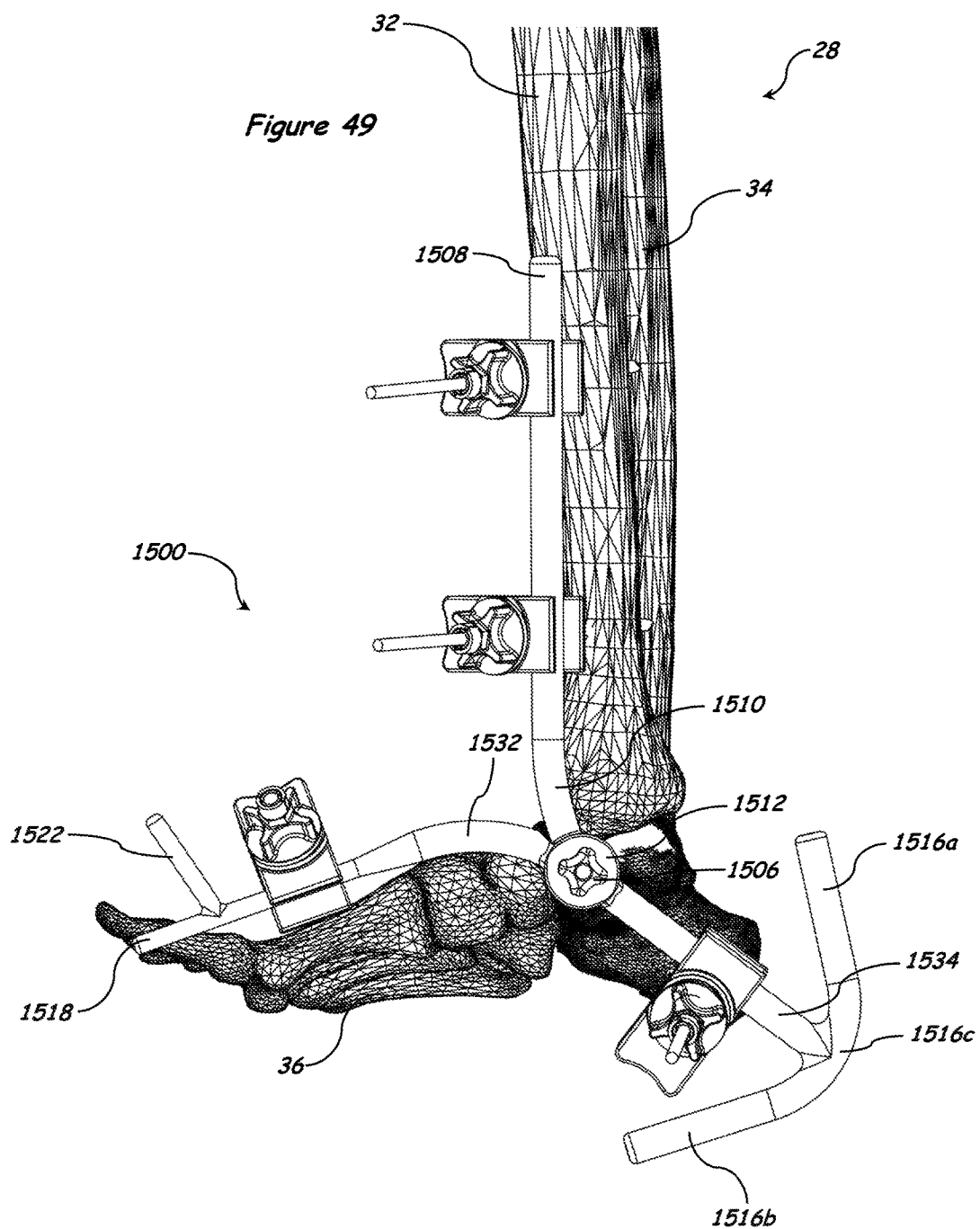
FIG. 49 is a medial perspective view of a leg with the third embodiment of the ankle external fixator and its associated clamps.
Figure 50:
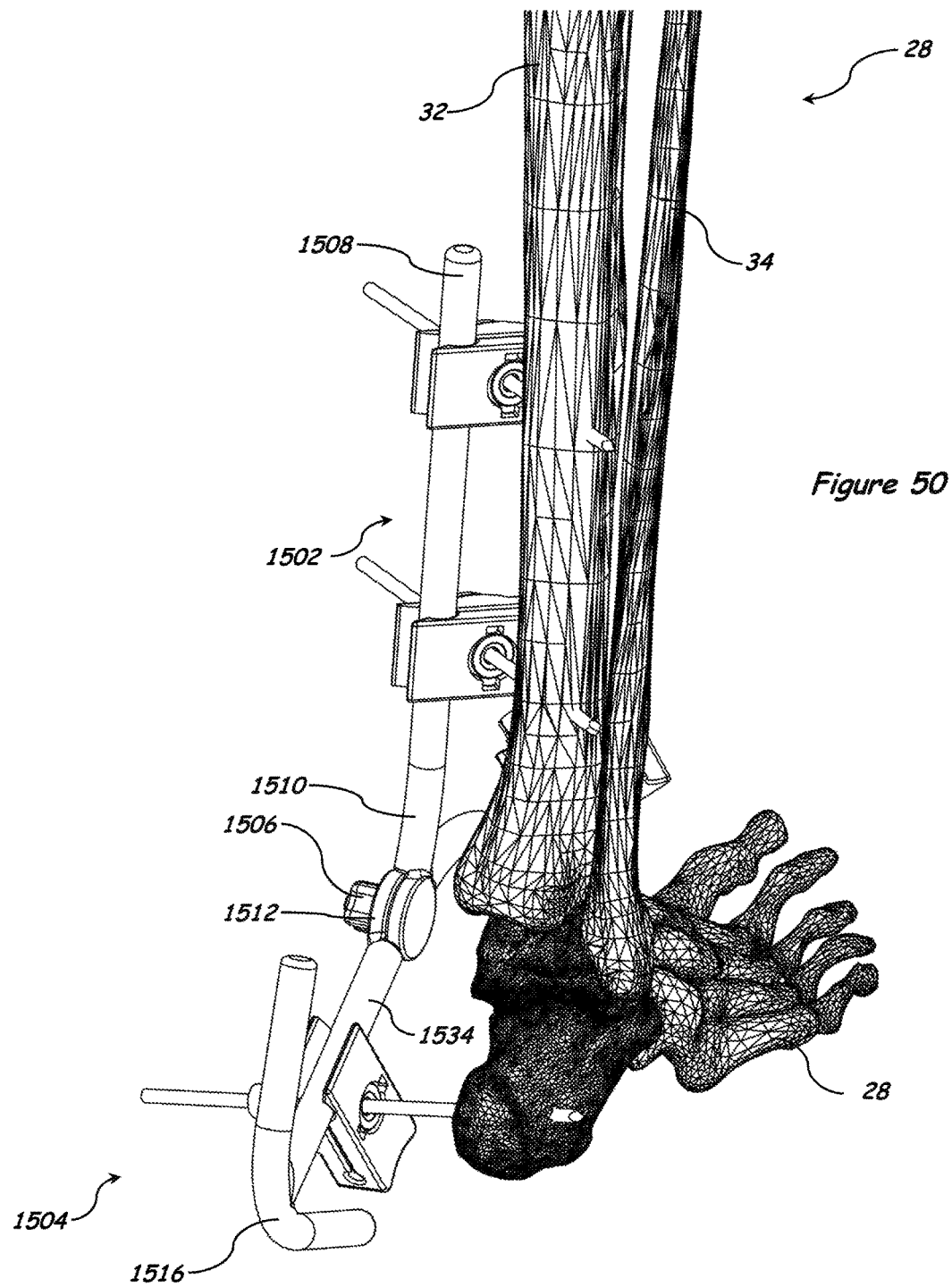
FIG. 50 is a posterior-lateral perspective view of a leg with the third embodiment of the ankle external fixator and its associated clamps.
Figure 51:
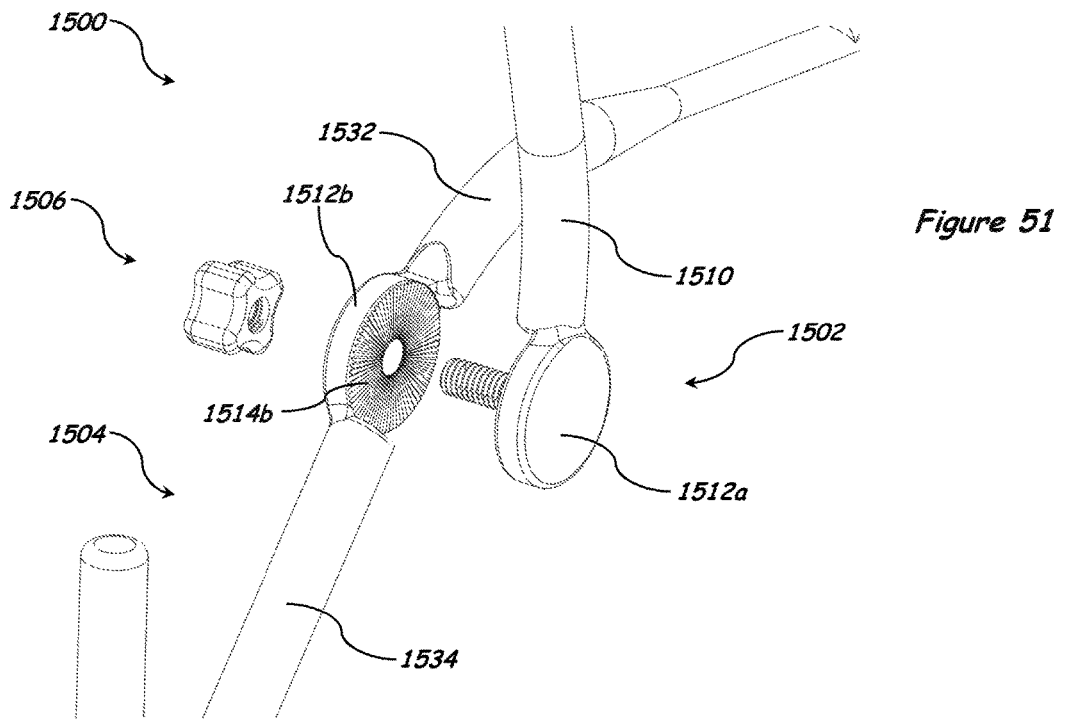
FIG. 51 is a detailed posterior-lateral exploded view of the third embodiment of the ankle external fixator.
Figure 52:
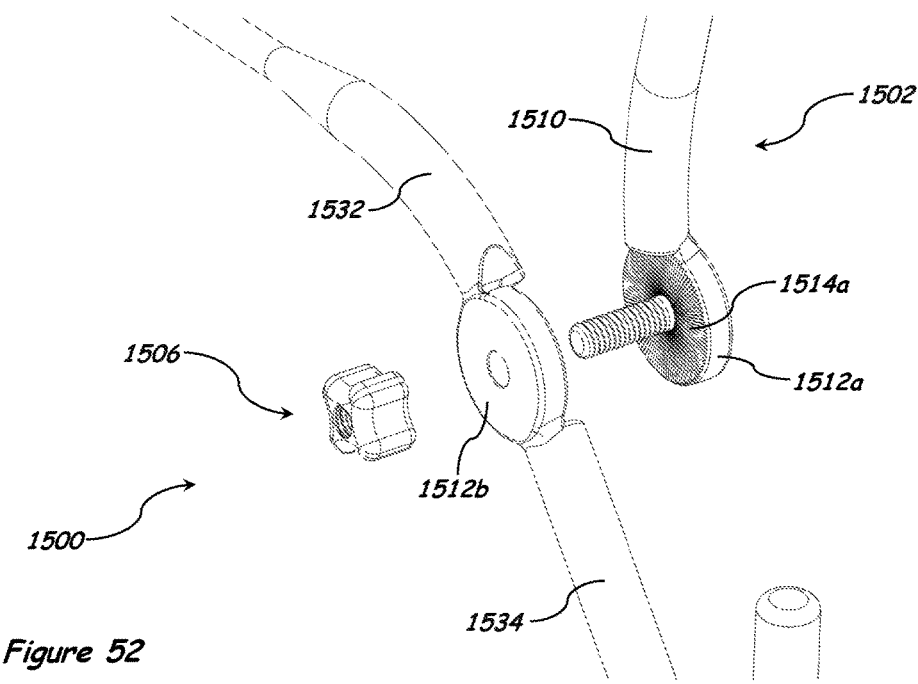
FIG. 52 is a detailed posterior-medial exploded view of the third embodiment of the ankle external fixator.
Figure 53:
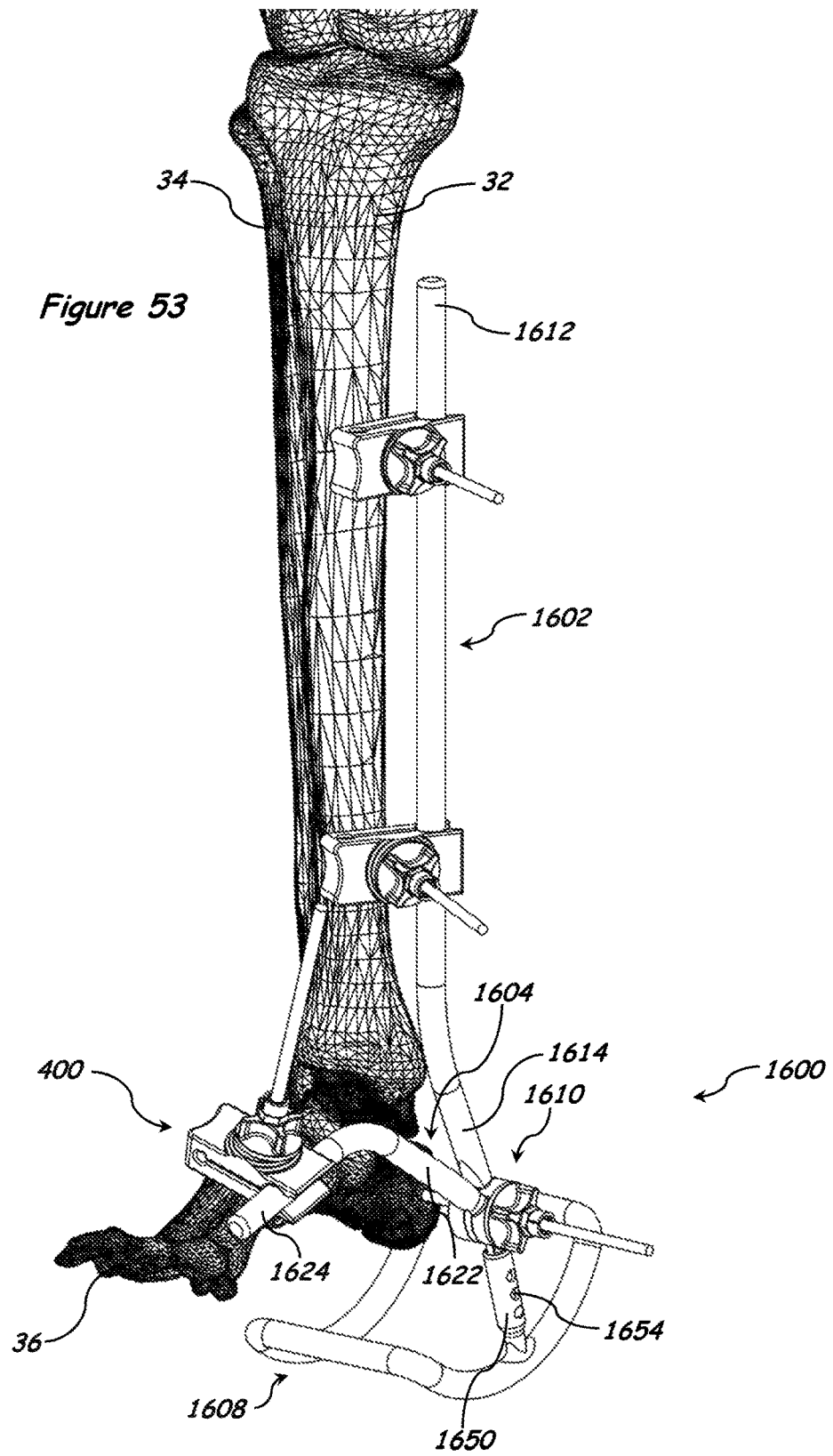
FIG. 53 is an anterior-medial perspective view of a leg with a fourth embodiment of the ankle external fixator and its associated clamps.
Figure 54:
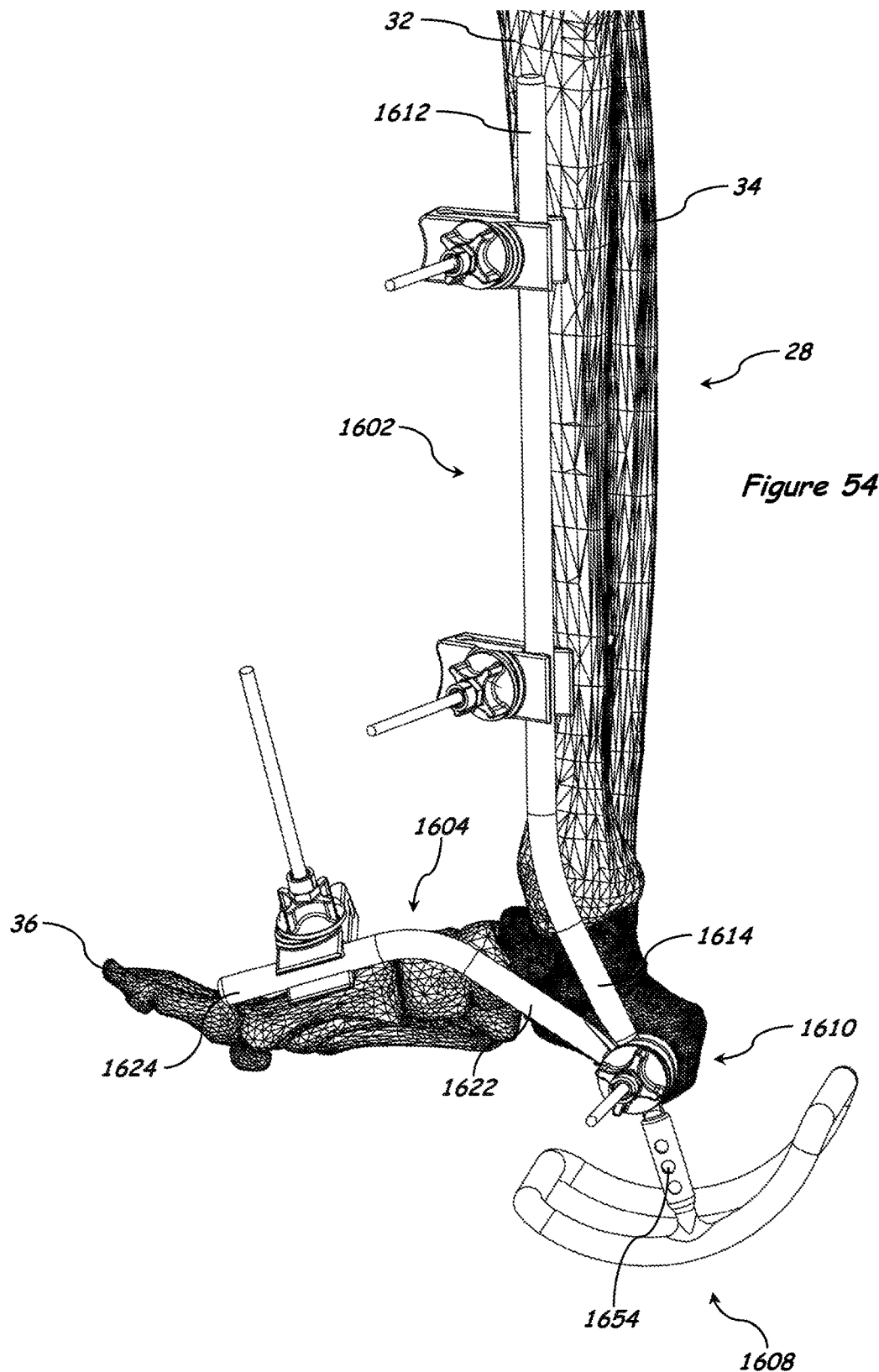
FIG. 54 is a medial perspective view of a leg with the fourth embodiment of the ankle external fixator and its associated clamps.
Figure 55:
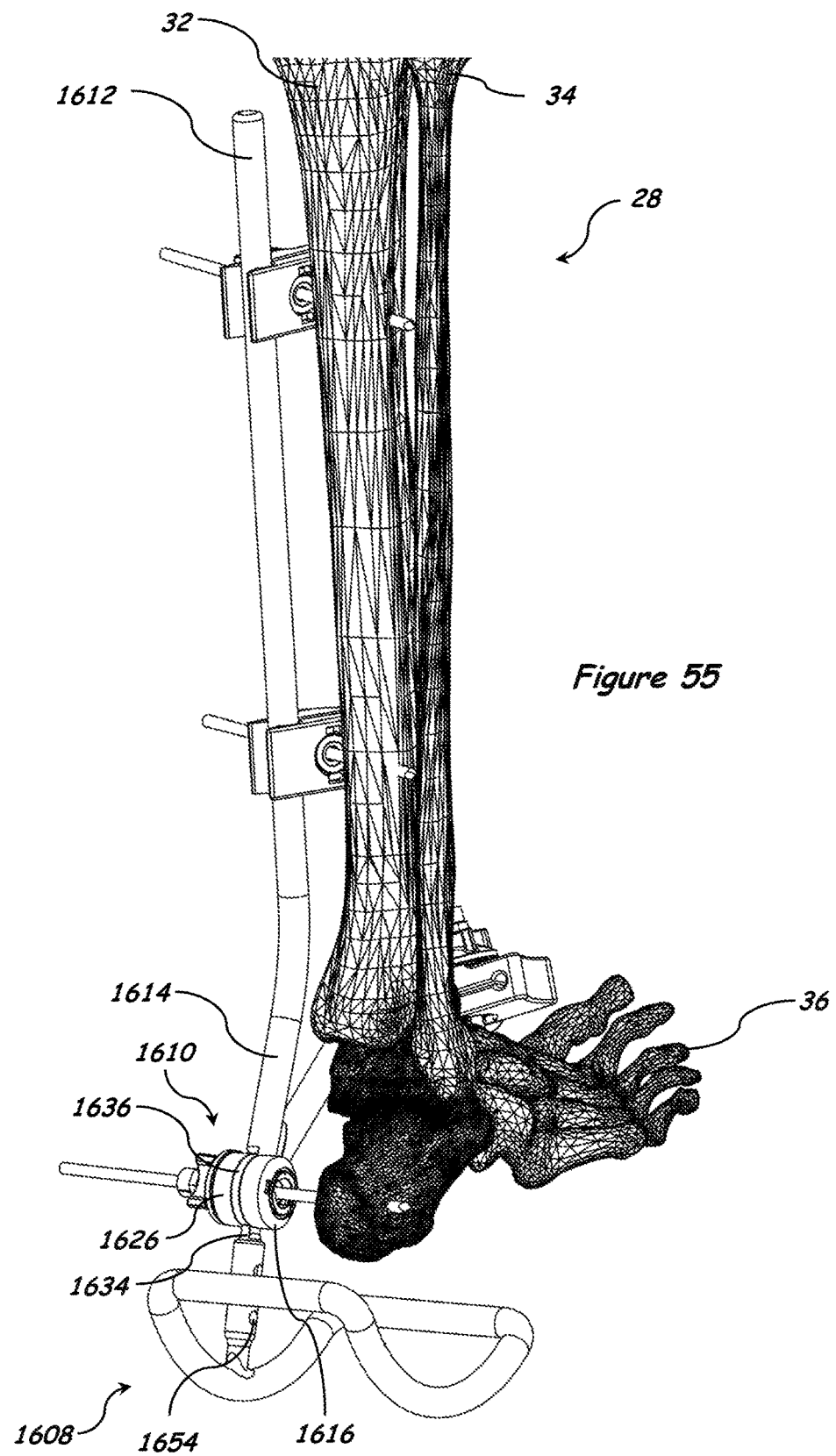
FIG. 55 is a posterior-lateral perspective view of a leg with the fourth embodiment of the ankle external fixator and its associated clamps.
Figure 56:
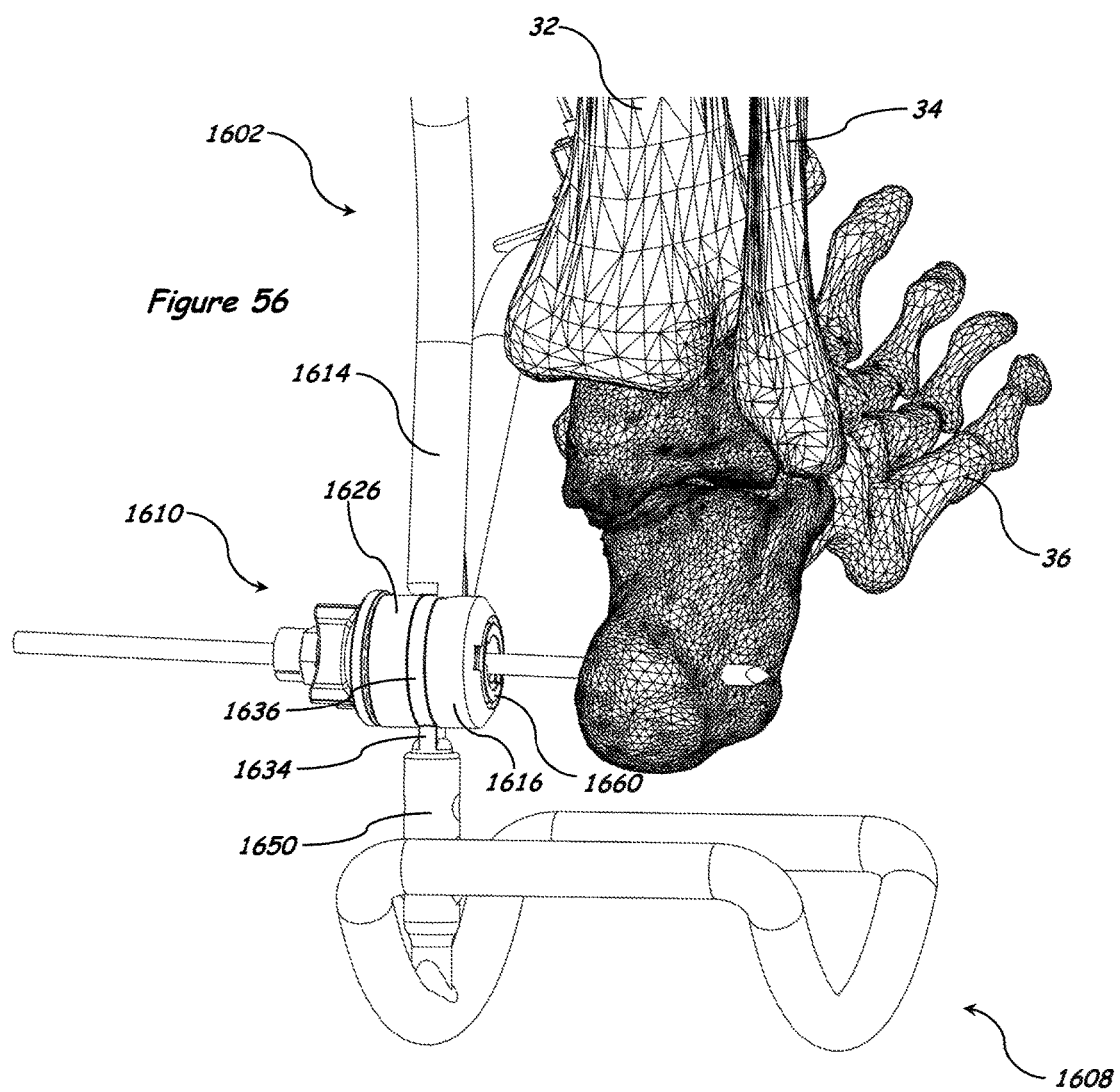
FIG. 56 is a detailed posterior-lateral view of the fourth embodiment of the ankle external fixator.
Figure 57:
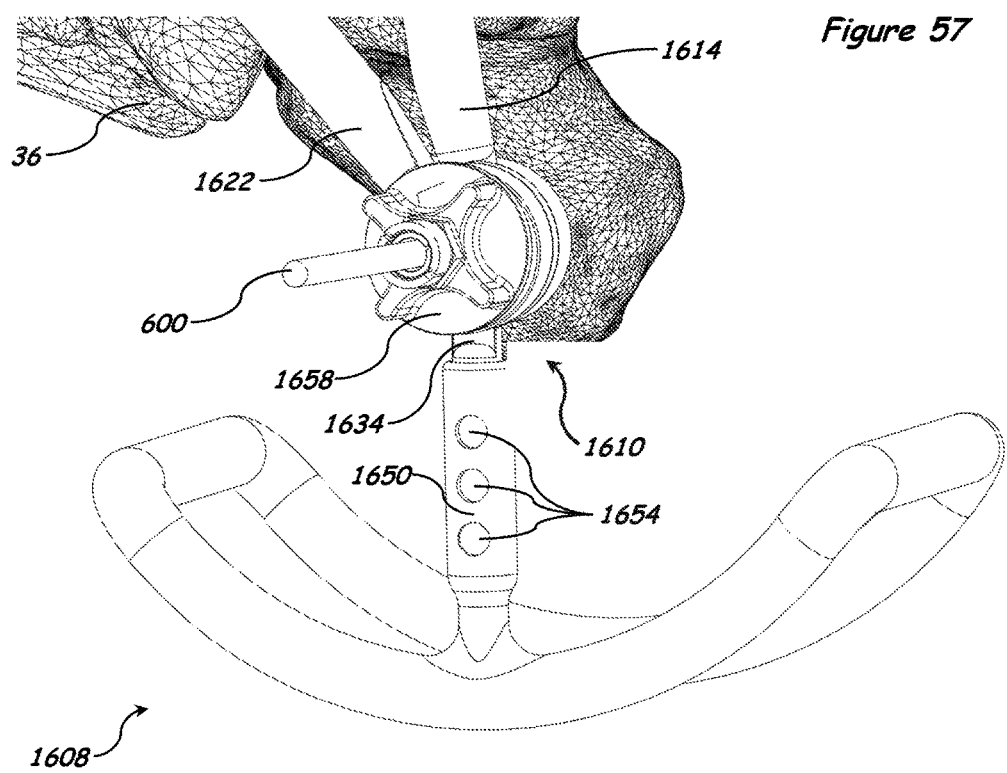
FIG. 57 is a detailed medial view of the fourth embodiment of the ankle external fixator.
Figure 58:
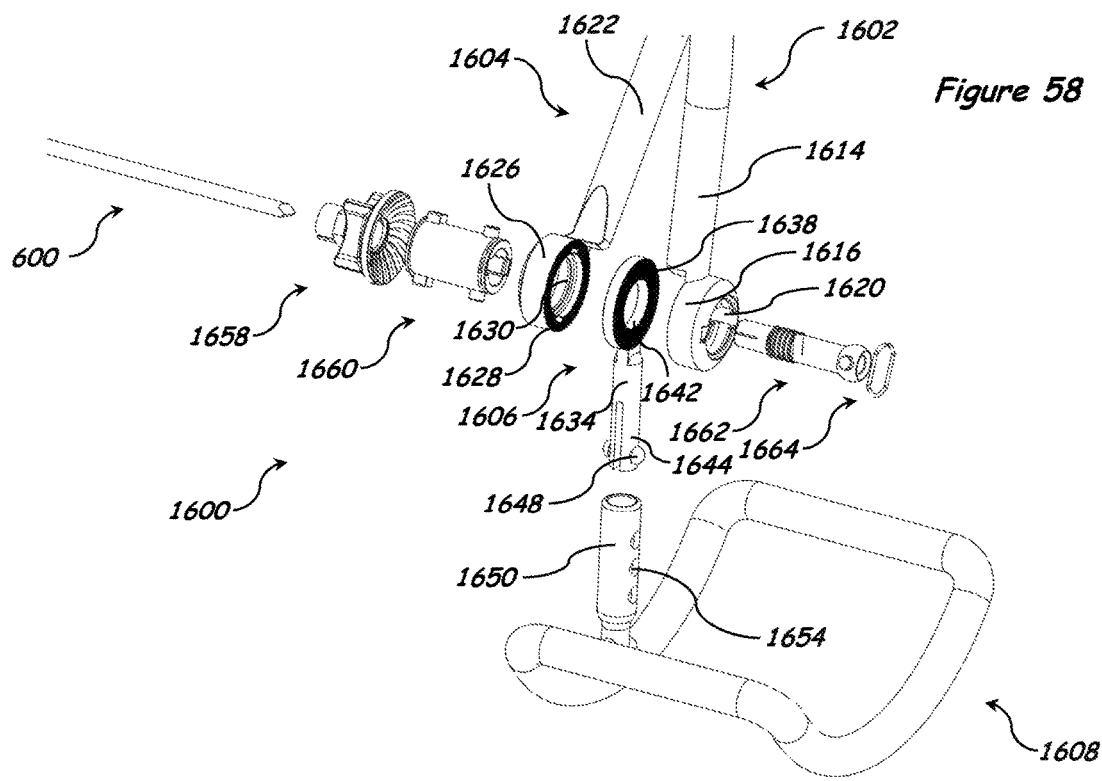
FIG. 58 is a detailed posterior-lateral exploded view of the fourth embodiment of the ankle external fixator.
Figure 59:
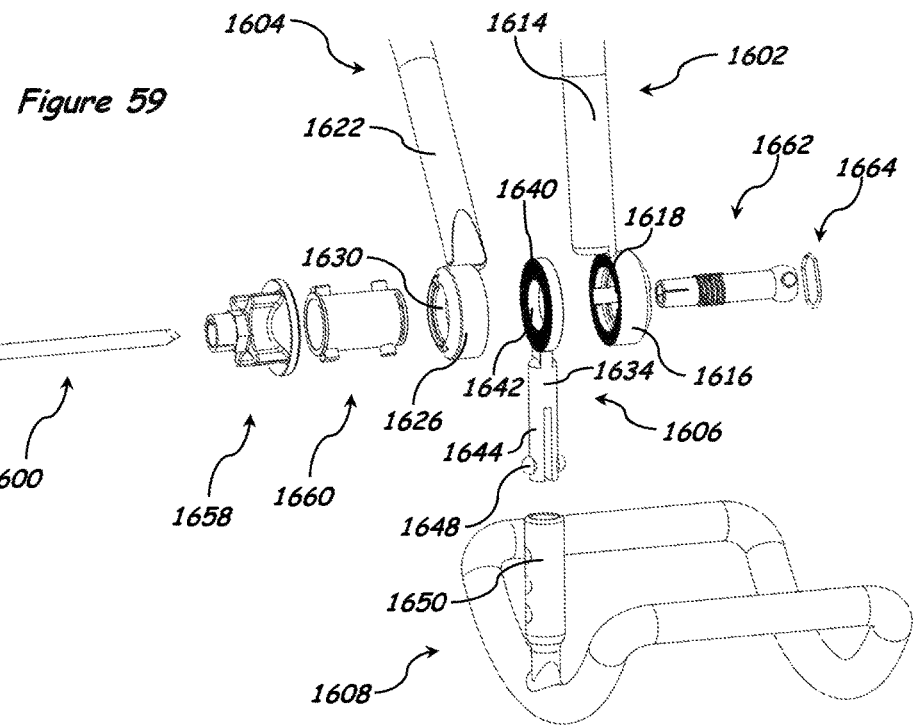
FIG. 59 is a detailed posterior-medial exploded view of the fourth embodiment of the ankle external fixator.
Figure 60:
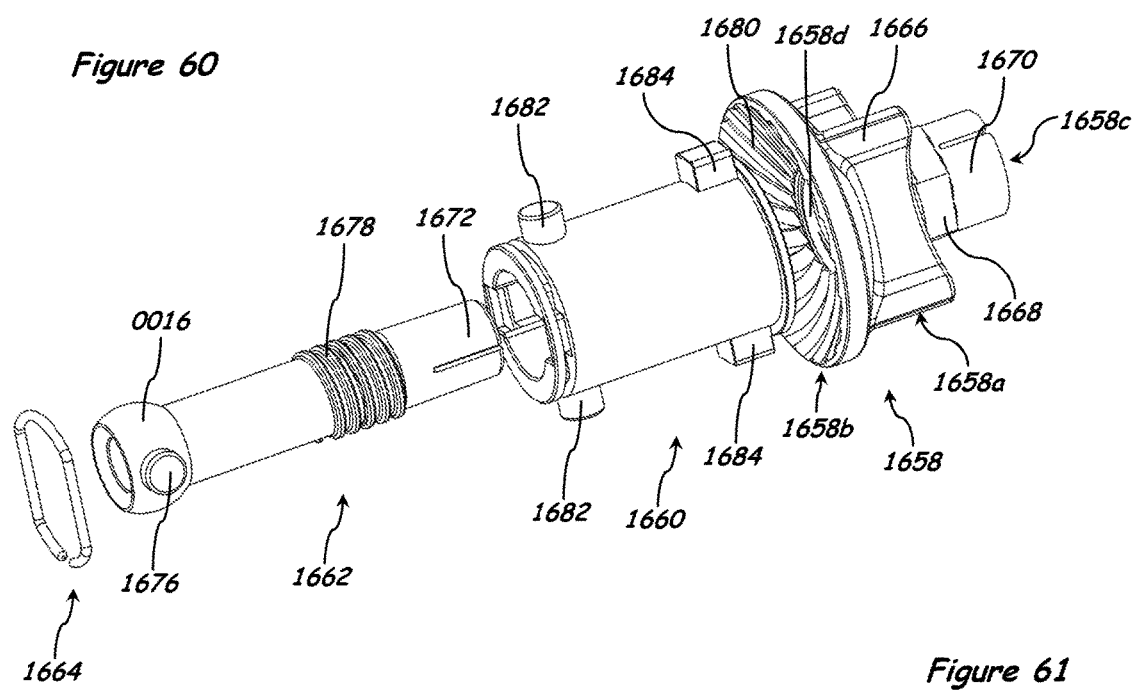
FIG. 60 is a detailed exploded view of the cartridge utilized in the fourth embodiment of the ankle external fixator.
Figure 61:
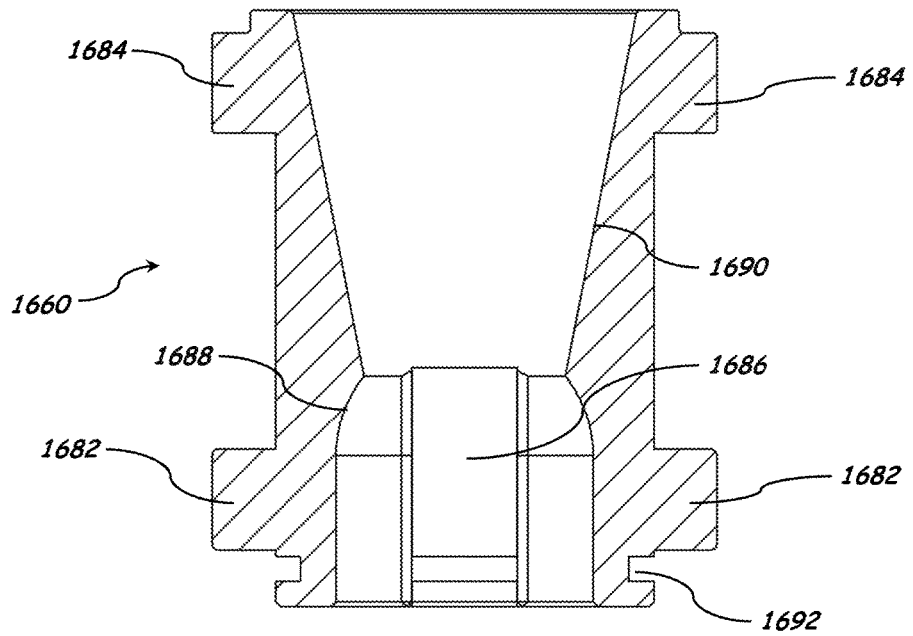
FIG. 61 is a section view of the main body of the cartridge utilized in the fourth embodiment of the ankle external fixator.

Referring now to FIGS. 48-50, a third embodiment of an exemplary ankle-spanning external fixation system 1500 is illustrated mounted on a lower extremity 28 comprising a tibia 32, fibula 34 and a foot 36.

FIGS. 48-52 illustrate a third embodiment of an exemplary ankle-spanning external fixation system 1500 comprises a proximal frame including a first external fixation component 1502a, a second external fixation component 1502b, and a fastener 1506, and connecting to a distal (e.g., first) frame such as foot frame 1504, and open-end clamp systems 400 and 1300. The ankle-spanning external fixation system 1500 can be adapted to couple to the tibia 32, the fibula 34 and/or the foot 36 by use of a closed-end clamp system 300 and/or the open-end clamp systems 400 and 1300.

The first and second external fixation components 1502a and 1502b, and the foot frame 1504, fastener 1506 and open-end clamp systems 400 and 1300 can be formed of any suitable material known to one skilled in the art that provides an adequate stiffness or resistance to torsion, stress, torque and/or other forces that may be applied to the system 1500, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form the first external fixation component, the second external fixation component, the foot frame, the fastener, and the open-end clamp systems of aluminum, stainless steel and/or carbon fiber, at least because these materials have properties that are well suited to external fixation of fractures.

In the illustrated embodiment 1500 in FIGS. 48-52, a proximal (e.g., second) bar frame comprises a first external fixation component 1502a comprising a straight first component proximal (e.g., first) end portion 1508 and a curved first component distal (e.g., second) end portion 1510 including a first pivot structure 1512a comprising a rough surface 1514a and a threaded shaft centered and formed perpendicularly on the rough surface 1514a, and said first external fixation component 1502a pivotedly coupled and locked to a second external fixation component 1502b comprising a straight second component proximal (e.g., first) end portion 1534, a straight second component distal (e.g., second) end portion 1518 of a reduced diameter, and a curved or arc portion 1532 connecting the second component proximal end portion 1534 and a second component distal end portion 1518, said arc portion 1532 having a pivot structure 1512b with a rough surface 1514b and a centered through-bore for receiving the threaded shaft of the pivot structure 1512a to form a movable joint or hinge. A fastener, such as threaded nut 1506, is coupled to the threaded shaft of the first pivot structure 1512a to form a threaded connection to lock the movable joint, thus, also locking the first and second external fixation component 1502a and 1502b in place. The interaction between the rough surfaces 1514a and 1514b in a locking state provides anti-rotation to the first and second fixation components 1502a and 1502b. The second component proximal end portion 1534 is attached by, for example, welding, soldering or gluing to a distal frame, such as the foot frame 1504, to form a unitary, prefabricated modular structure. Alternatively, the foot frame 1504 can be integrally machined or formed with the second external fixation component 1502b from a single piece of metal or other material to form a unitary structure. The foot frame 1504 comprises a straight posterior segment 1516a, a straight inferior segment 1516b, and a curved or arc segment 1516c connecting the straight posterior segment 1516a and the straight inferior segment 1516b to form a curved frame or rod or bar for protecting and supporting both the posterior and the inferior aspects of a foot or joint such as the ankle while healing is taken place. Said inferior frame portion 1516b and said posterior frame portion 1516a are operatively disposed in at least partially surrounding and spatial relation to the ankle or the heel of the foot 36, wherein said posterior frame portion 1516a extends angularly from and above said inferior frame portion 1516b. The second component distal end portion 1518 has a smaller diameter and is attached (e.g. welded, soldered or glued) to an outrigger 1522 used as a clamp attachment, for example. The outrigger 1522 can also be integrally machined or formed with the second external fixation component 1502b.

The first and second component proximal end portions 1508 and 1534, the first and second component distal end portions 1510 and 1518, and more generally the first and second external fixation components 1502a and 1502b and the posterior and inferior segments 1516a and 1516b can be straight or curved. The first and second external fixation components 1502a and 1502b and the foot frame 1504 of the system 1500 can have any cross-sectional shapes such as circle, square, rectangle, hexagon, etc., and can have uniform diameter or varied diameter along their lengths. The first and second external fixation components 1502a and 1502b including the foot frame 1504 of the system 1500 can each be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy).

The pivot structures 1512a and 1512b can have any cross-sectional shapes, not just limited to a circular shape as illustrated in this example. The pivot structures 1512a and 1512b can also have any lengths or thickness as measured along its pivot axis. The pivot structures 1512a and 1512b of the movable hinge or joint can each also be an integral part of (e.g. integrally formed with) or a separate part to (e.g. removably coupled to) their respective first external fixation component 1502a and second external fixation component 1502b. The rough surfaces 1514a and 1514b can include serration or radial interdigitation or combinations thereof. In a system where both pivot structures 1512a and 1512b each comprises a through-bore, a second fastener having a head and a threaded shaft can be used to couple the pivot structures 1512a and 1512b and operably interacts with the threaded nut 1506 to lock the pivot structures 1512a and 1512b. The fastener(s) can have a secure gripping surface for ease of handling during surgery. As illustrated, the first external fixation component 1502a and the second external fixation component 1502b including the foot frame 1504 each is made as a unitary modular structure. In the modular structure, the first external fixation component 1502a and the second external fixation component 1502b and the foot frame 1504 can each be made from a plurality of straight and/or curved segments connected via threads, snap-fit or interference fit.

Referring now to FIGS. 53-57, a fourth embodiment of an exemplary ankle-spanning external fixation system 1600 is shown mounted on an exemplary lower leg 28 comprising a tibia 32, fibula 34 and a foot 36.

FIGS. 53-61 illustrate a fourth embodiment of an exemplary ankle-spanning external fixation system 1600 comprising a proximal (e.g., first) frame having a first external fixation component 1602 and a second external fixation component 1604, a proximal frame connector 1606, and a distal (e.g., second) frame or a foot frame 1608, a distal frame connector 1650, a cartridge system 1610 and an open-end clamp system 400. The ankle-spanning external fixation system 1600 can be adapted to attach to the tibia 32, the fibula 34 and/or the foot 36 by use of a closed-end clamp system 300 and/or the open-end clamp systems 400 and 1300 and other fixation elements such as bone pins 600 or 700.

The first external fixation component 1602, the second external fixation component 1604, the proximal (e.g., first) frame connector 1606, the foot frame 1608, the distal (e.g., second) frame connector 1650, the cartridge system 1610 and the open-end clamp system 400 can be formed of any suitable material known to one skilled in the art that provides an adequate stiffness or resistance to torsion, stress, torque and/or other forces that may be applied to the system 1600, including the structural arrangement at a fixation site and/or the material forming the components of an external fixation system. Example suitable materials include, but are not limited to, biocompatible materials, materials that can be made biocompatible, ceramics, polymers, polyethylene, ultra-high-molecular-weight polyethylene (UHMWPE), shape memory polymer, carbon fiber, metal, metal alloy, shape memory metals, tantalum, titanium (Ti), and cobalt alloys (e.g., cobalt-chromium (CoCr), cobalt-chromium-molybdenum (CoCrMo)). The material is also preferably, but not necessarily, radiolucent. It is considered advantageous to form the first external fixation component, the second external fixation component, the third external fixation component, the fourth external fixation component, the cartridge system and the open-end clamp system of aluminum, stainless steel and/or carbon fiber, at least because these materials have properties that are well suited to external fixation of fractures.

In the illustrated embodiment 1600 in FIGS. 53-61, the proximal frame comprises the first external fixation component 1602 and the second external fixation component 1604. The external fixation component 1602 comprises a first component proximal (e.g., first) end portion 1612 and a first component distal (e.g., second) end portion 1614 integrally formed with or coupled to a pivot structure 1616 having a rough surface 1618 and a through-bore bound by an inner surface having engagement features such as threads and key ways 1620 configured for receiving and connecting to at least a portion of the cartridge system 1610 for coupling to a bone and locking the system 1600. The second external fixation component 1604 comprises a second component distal (e.g., first) end portion 1624 and a second component proximal (e.g., second) end portion 1622 integrally formed with or coupled to a pivot structure 1626 having a rough surface 1628 and a through-bore bound by an inner surface having engagement features such as threads and key ways 1630 configured for receiving and connecting to at least a portion of the cartridge system 1610 for coupling to a bone and locking the external fixation components 1602 and 1604 in position.

The first and second external fixation components 1602 and 1604 can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy). The first and second component proximal end portions 1612 and 1622 and the first and second component distal end portions 1614 and 1624 can be straight or curved. The first and second external fixation components 1602 and 1604 can have any cross-sectional shapes such as circle, oval, triangle, rectangle, square, polygonal shape. The first and second external fixation components 1602 and 1604 can have any uniform or varied diameter or thickness along their lengths. The pivot structures 1616 and 1626 can have any external cross-sectional shapes, not limited to just circular shape as illustrated in this example. The pivot structures 1616 and 1626 can also have any lengths or thickness as measured along its pivot axis. The pivot structures 1616 and 1626 can also be integrally formed with or removably coupled to their respective first external fixation component 1602 and second external fixation component 1604. The rough surfaces 1618 and 1628 can include serration or radial interdigitation or combinations thereof.

The proximal frame connector 1606 comprises an elongated body comprising a connector proximal end portion 1634 integrally formed with or coupled to a pivot structure 1636 having a rough surface 1638 and an opposing rough surface 1640 and a through-bore connecting the two opposing surfaces 1638 and 1640 bound by an inner surface configured (e.g. key ways 1642) for receiving and locking onto at least a portion of the cartridge system 1610, and a bifurcated connector distal end portion including a pair of movable portions 1644 that are movable to flex toward and away from each other and arranged with one or more protrusions 1648 to engage with a hole 1654 in a distal frame connector 1650 of the lower frame such as the foot frame 1608.

The distal frame such as the foot frame 1608 comprises a ring frame configured to protect both the posterior and inferior aspects of a foot or the ankle. The ring frame comprises a multiple curved elongated body structure defining a first curved side rod spaced apart and parallel to a second curved side rod wherein a first end connector extending from said first curved side rod to said second curved side rod in said inferior portion and a second end connector extending from said first curved side rod to said second curved side rod in said posterior portion. Said inferior frame portion and said posterior frame portion are operatively disposed in at least partially surrounding and spatial relation to the ankle or the heel of the foot 36, wherein said posterior frame portion extends angularly from and above said inferior frame portion. The foot frame 1608 has a curvature from inferior to posterior with its concave surface orienting toward the heel of the foot. The foot frame 1608 further comprises a distal frame connector 1650 with a through-bore extending longitudinally through at least a portion of the elongated body 1650 for receiving the bifurcated connector distal end portion 1644, and one or more holes 1654 for engaging with the one or more protrusions 1648 on the bifurcated connector distal end portion 1644. The elongated body 1650 is attached to a portion of one of the first and second curve side rods. The arrangement of the multiple holes 1654 along the distal frame connector 1650 provides adjustability to the spatial relation between the foot frame 1608 and the heel or the ankle. The foot frame including the distal frame connector and the proximal frame connector can be formed as a unitary, prefabricated modular component (e.g. from multiple pieces welded together), a unitary component (e.g. from a single piece of material by molding), or a modular component (e.g. multiple pieces removably threaded together to allow surgeons to use as-is or to reconfigure to match the patient anatomy).

The cartridge system 1610 for coupling the system to a bone portion via a bone pin 600 or 700 and locking the pivot structures 1616, 1626, and 1636, and thus, also locking the ankle-spanning external fixation system 1600 comprises a knob 1658, a main body 1660, a variable position shaft 1662 and a retaining clip 1664.

The knob 1658 comprises a knob body 1658a having a main body facing end 1658b and an opposing end 1658c. The knob body 1658a includes a funnel-like or frusto-conical internal surface or an internal surface having one or more tapered facets to receive and alternatively circumferentially compress and release a slit end or a funnel-like or tapered external surface of the shaft 1662 for clamping a fixation element such as bone pin 600. The funnel-like or frusto-conical internal surface or more generally the through-bore bound by walls extending from the main body facing end 1658b to the opposing end 1658c of the knob body 1658a is designed to be larger toward the main body facing end 1658b than toward the opposing end 1658c of the knob body 1658a, and includes a first locking feature such as threads 1658d. The tapered or conical internal surface inside the knob body 1658a can be replaced with a taper insert. The opposing end 1658c of the knob body 1658a can include one or more slits or breakable lines for accommodating a broader range of dimensional tolerances of the bone pin 600 or 700. The knob 1658 can have irregularly shaped geometry 1666 for providing a secure grip surface and optionally a hexagonally shaped geometry 1668 that interfaces with a wrench.

The variable position shaft or shaft 1662 includes an end portion including a stopper or an enlarged structure or structures such as a head 0016 for preventing the shaft 1662 from passing completely through the main body 1660, and a locking or engagement feature such as threads 1678 on the external surface of the shaft 1662, and one or more breakable lines or slits 1672 on an opposing end portion of the shaft. The slit end 1672 of the shaft 1662 can be tapered to match the tapered internal surface of the knob body 1658a. The funnel like or tapered internal surface of the knob body 1658a preferably interacts via the engagement features, such as the threads 1658d and 1678, with the externally tapered or funnel-like surface or the slit end 1672 of the shaft 1662 to provide clamping. The through-bore or opening in the opposing end 1658c of the knob 1658 has a diameter smaller than the uncompressed diameter of the slit end 1672 of the shaft 1662 to provide interference fit among the inner surface of the knob 1658, the slit end 1672 and the bone pin such as bone pin 600 or 700. The shaft 1662 is configured to extend through the main body 1660 and into the through-bore of the knob 1658 such that the stopper 0016 is disposed in the main body 1660 and at least a portion of the threads 1678 of the shaft 1662 and the slit end 1672 disposed outside the main body 1660 and inside the knob body 1658a. The shaft threads 1678 operably engage the internal threads 1658d of the knob 1658 in forming a threaded connection with the knob 1658 to form a cannulation or reception for receiving a bone pin, such as bone pin 600, of uniform diameter, or bone pin 700 of varying diameter. A portion of the shaft 1662 or the stopper 0016 can include an at least partially spherical surface to permit the bone pin 600 or 700 to orient relative to the main body 1660, and can have at least one anti-rotation feature such as protrusion 1676 adapted to sit in a key way in the main body 1660.

In operation, the tightening of the knob 1658 pushes the slit end 1672 of the shaft 1662, guided by the tapered internal surface or structure of the knob body 1658*a*, toward or through the opposing end 1658*c* of the knob 1658. The slit end 1672 is compressed circumferentially onto the bone pin 600 or 700 at the opposing end 1658*c* of the knob 1658 as the slit end 1672 is pushed through the smaller opening at the opposing end 1658*c* of the knob 1658, and thus, clamping onto the bone pin 600 or 700 by interference fit.

The main body 1660 is configured to extend through the pivot structures 1616, 1626, and 1636 of the first and second external fixation components 1602 and 1604 and the connector 1606. The main body 1660 has a cylindrical body with proximal protrusions 1682 for engaging with key ways 1620 on the inner surface of the pivot structure 1616 of the first external fixation component 1602 and distal protrusions 1684 for engaging with key ways 1630 on the inner surface of the pivot structure 1626 of the second external fixation component 1604. The main body 1660 has inner surface configured to operably interact with the shaft 1662 to provide both angular rotation of the shaft 1662 relative to the main body 1660 and anti-rotation of the shaft 1662 during locking. The inner surface of the main body includes one or more key way 1686 for capturing the protrusions 1676 of the shaft 1662 for rotational stability, concave surfaces 1688 for interacting with the at least partially spherical stopper 0016 of the shaft 1662 and tapered or conical surface 1690 for providing angular rotation of the shaft 1662, and slotted geometry 1692 that accepts a ring clip 1664 for preventing the variable position shaft 1662 to exit the main body 1660 once the cartridge system 1610 is completely assembled.

The ankle-spanning external fixation system 1600 is assembled by firstly, snap-fitting together the first external fixation component 1602, the second external fixation component 1604 and the connector 1606 via male/female ends on their pivot structures 1616, 1626 and 1636. When the first external fixation component 1602, the second external fixation component 1604 and the connector 1606 are rotated into their closed state, the key ways 1620, 1630 and 1642 of the respective pivot structures 1616, 1626 and 1636 become aligned and allow the assembled cartridge system 1610 to slide in. Once the cartridge system 1610 is in place, the first external fixation component 1602, the second external fixation component 1604 and the connector 1606 can be opened up to the desired position according to anatomical considerations. Once the current embodiment 1600 is deployed and in position, the cartridge system can be adjusted and then locked in place by further tightening knob 1658, which in turn locks the first external fixation component 1602, the second external fixation component 1604 and the connector 1606 via the interactions of rough surfaces 1618, 1638, 1640 and 1628.

Figure 62:
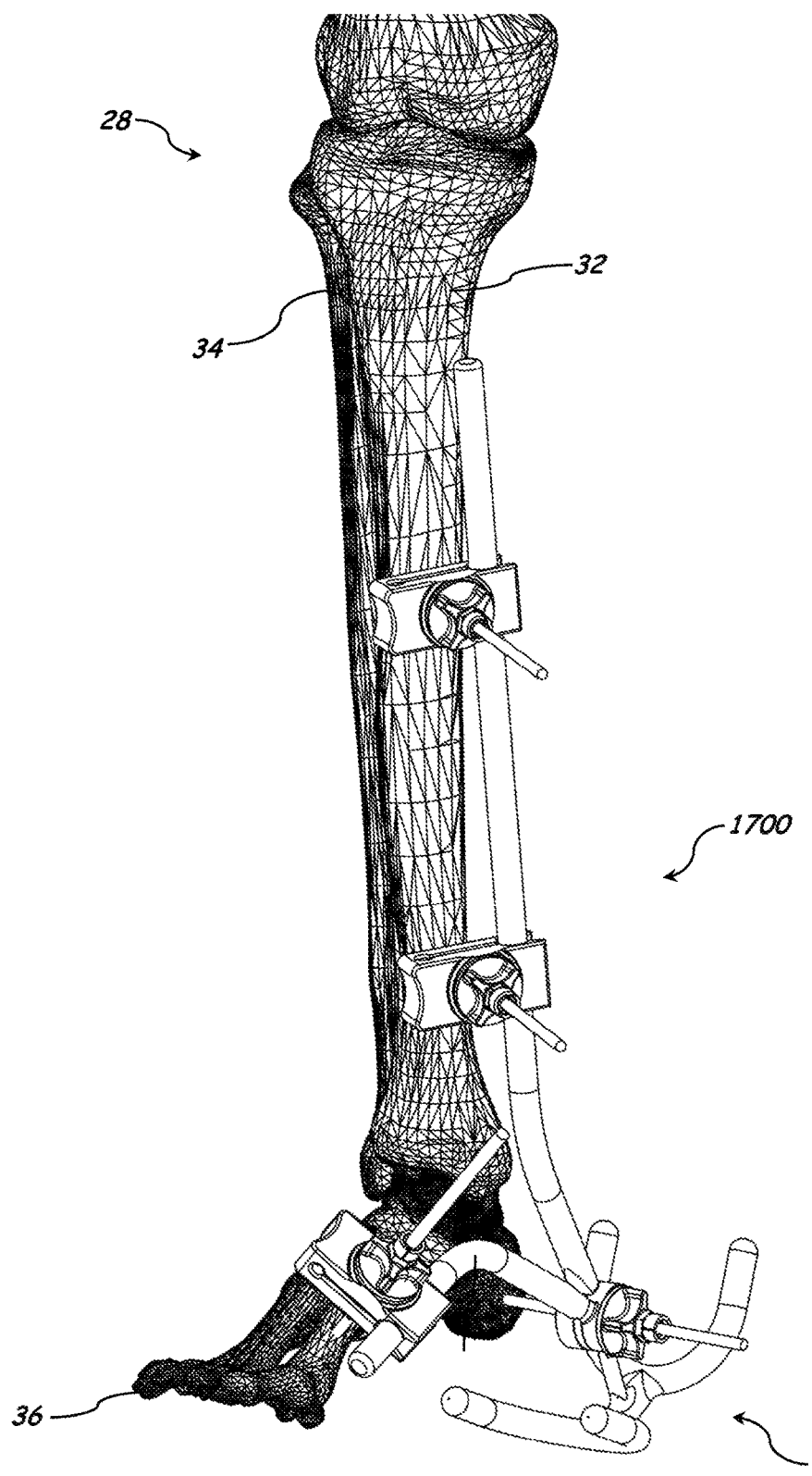
FIG. 62 is an anterior-medial perspective view of a leg with a fifth embodiment of the ankle external fixator and its associated clamps.
Figure 63:
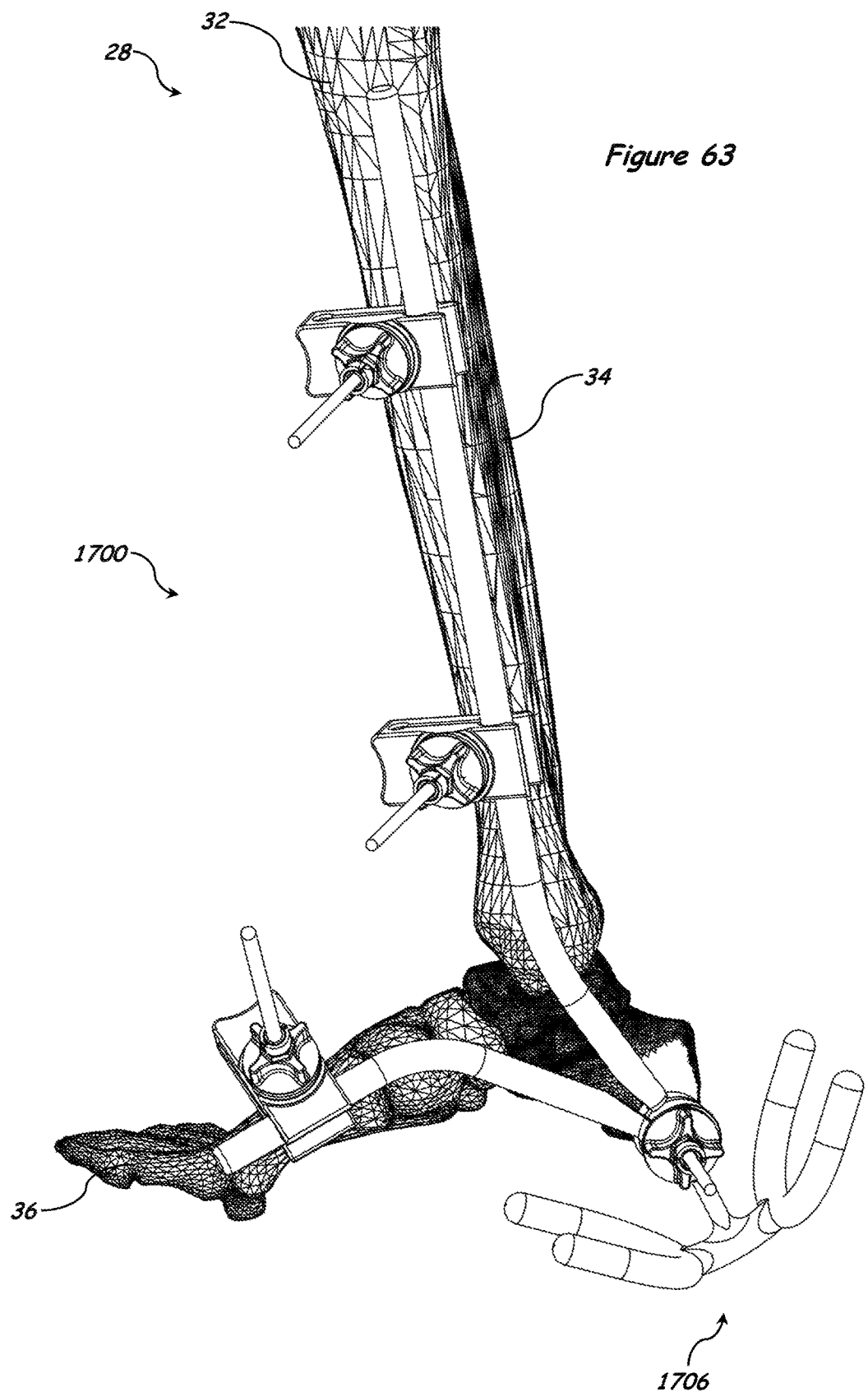
FIG. 63 is a medial perspective view of a leg with the fifth embodiment of the ankle external fixator and its associated clamps.
Figure 64:
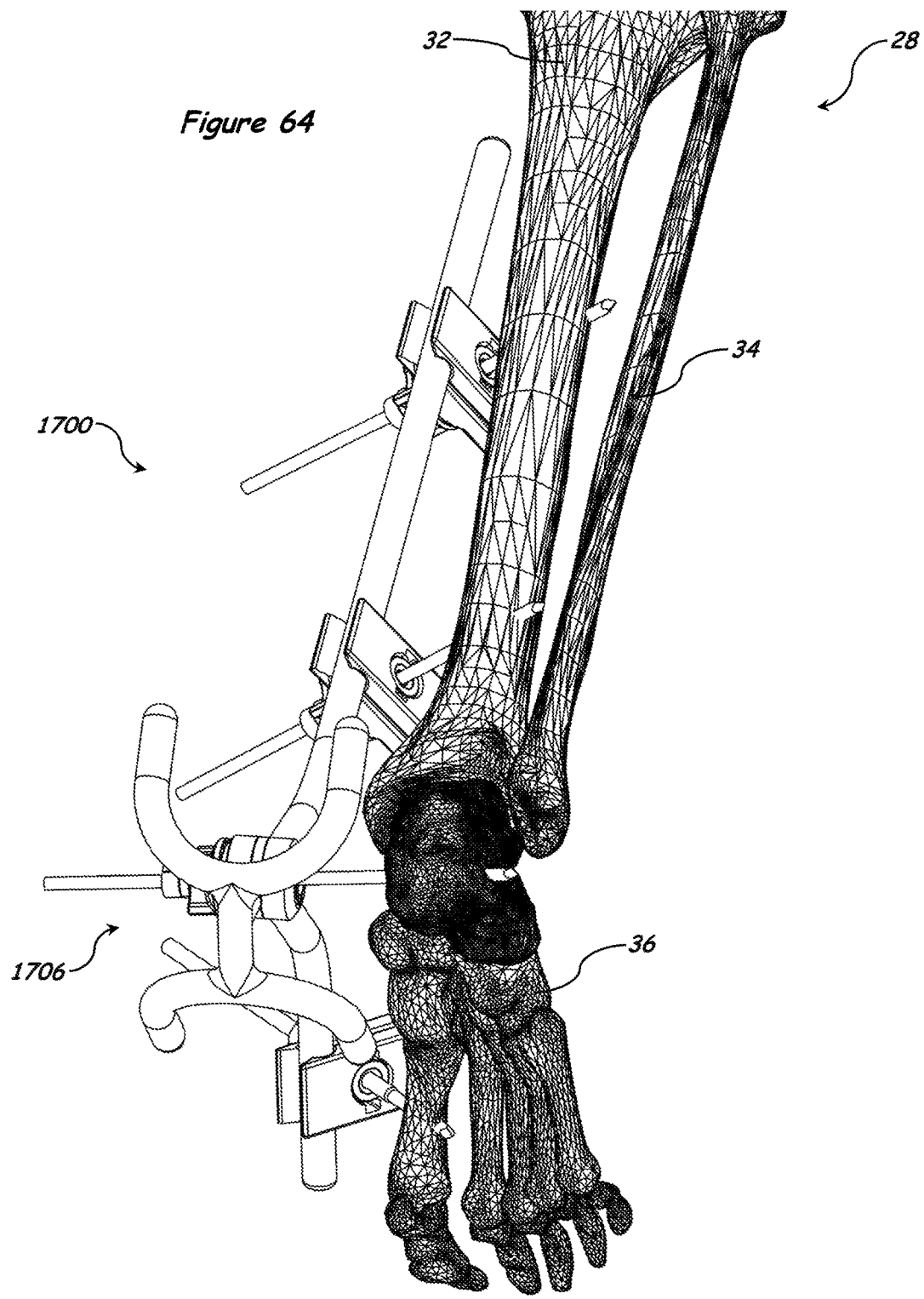
FIG. 64 is a posterior-inferior perspective view of a leg with the fifth embodiment of the ankle external fixator and its associated clamps.
Figure 65:
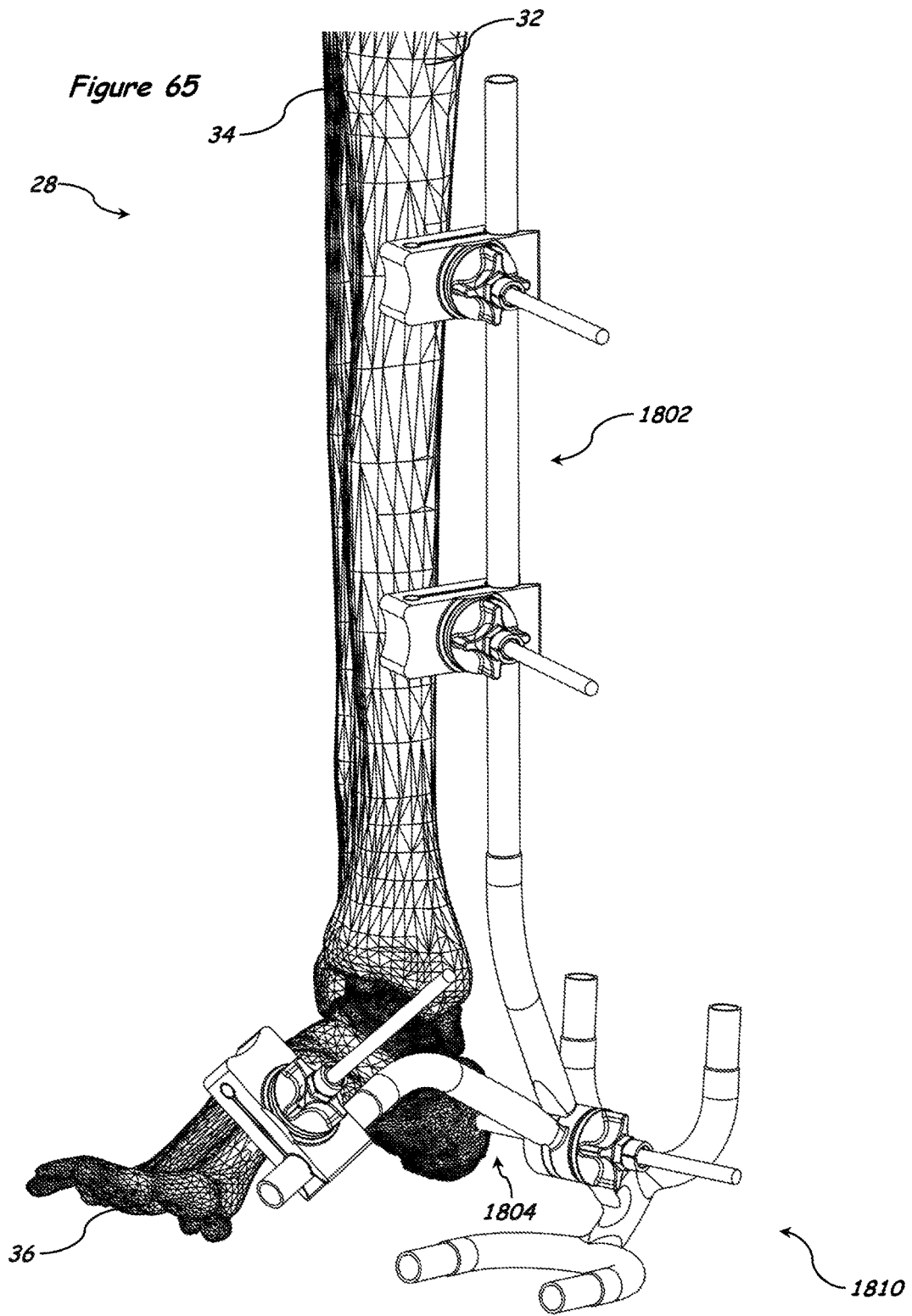
FIG. 65 is an anterior-medial perspective view of a leg with a sixth embodiment of the ankle external fixator and its associated clamps.
Figure 66:
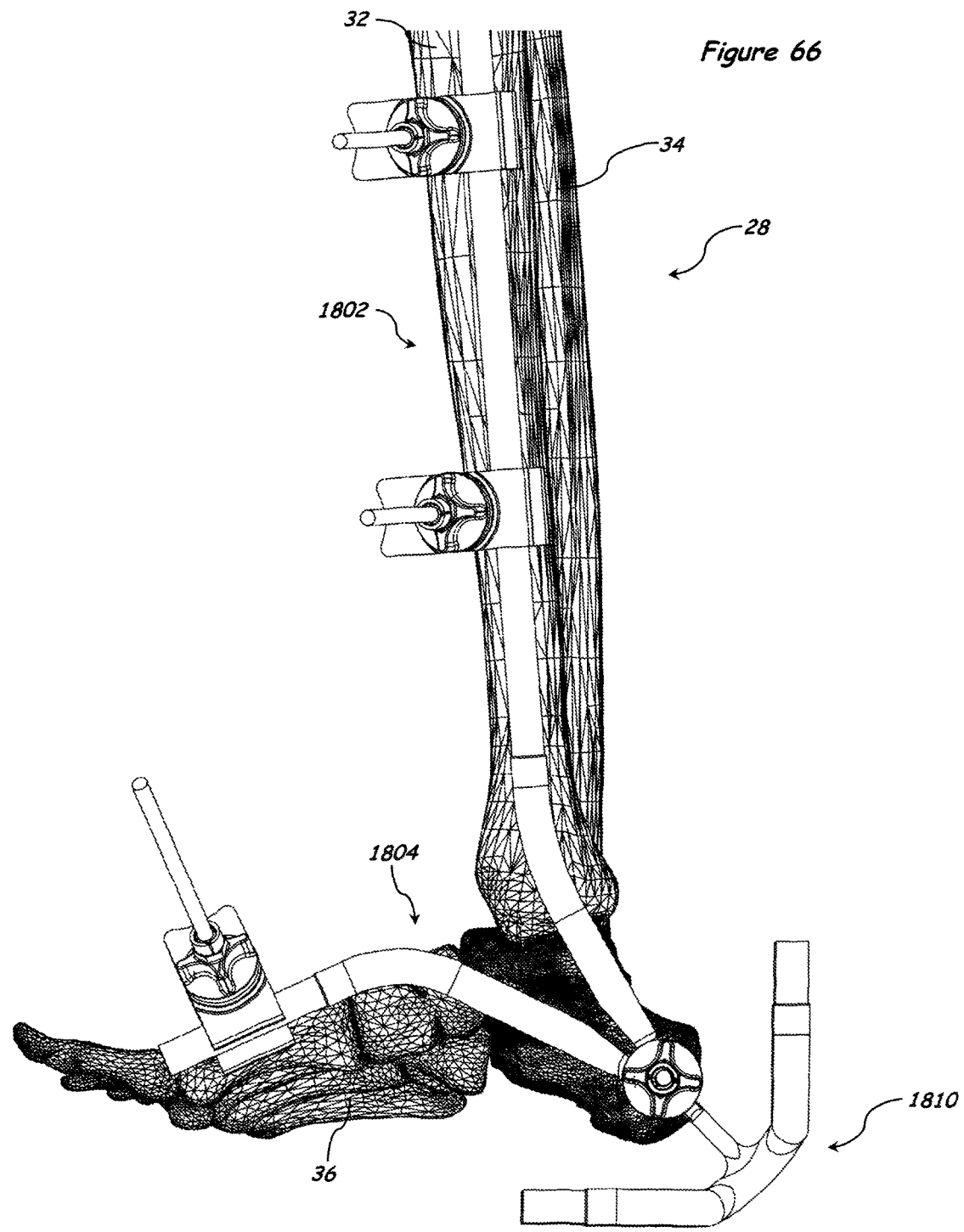
FIG. 66 is a medial perspective view of a leg with the sixth embodiment of the ankle external fixator and its associated clamps.
Figure 67:
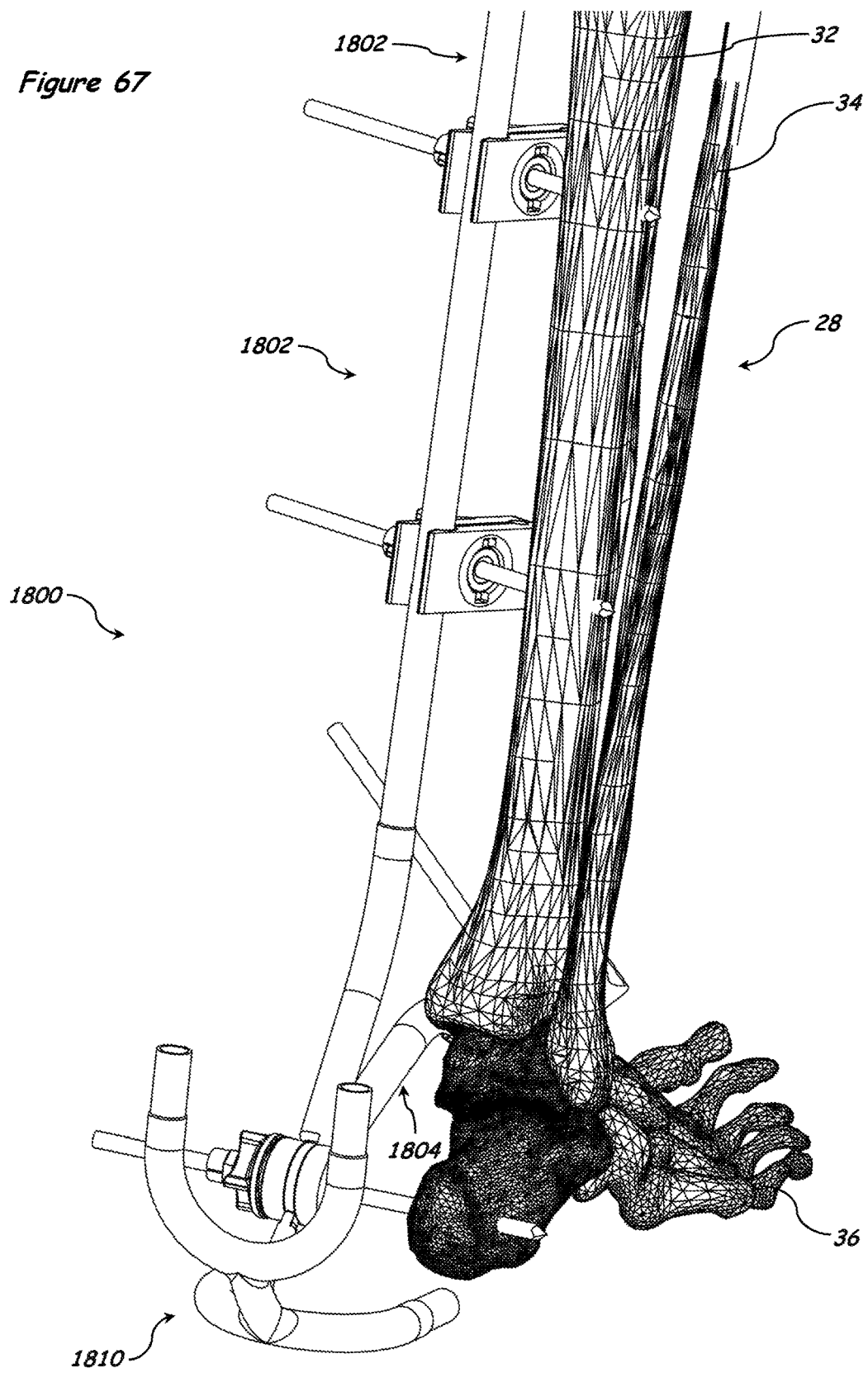
FIG. 67 is a posterior-lateral perspective view of a leg with the sixth embodiment of the ankle external fixator and its associated clamps.
Figure 69:
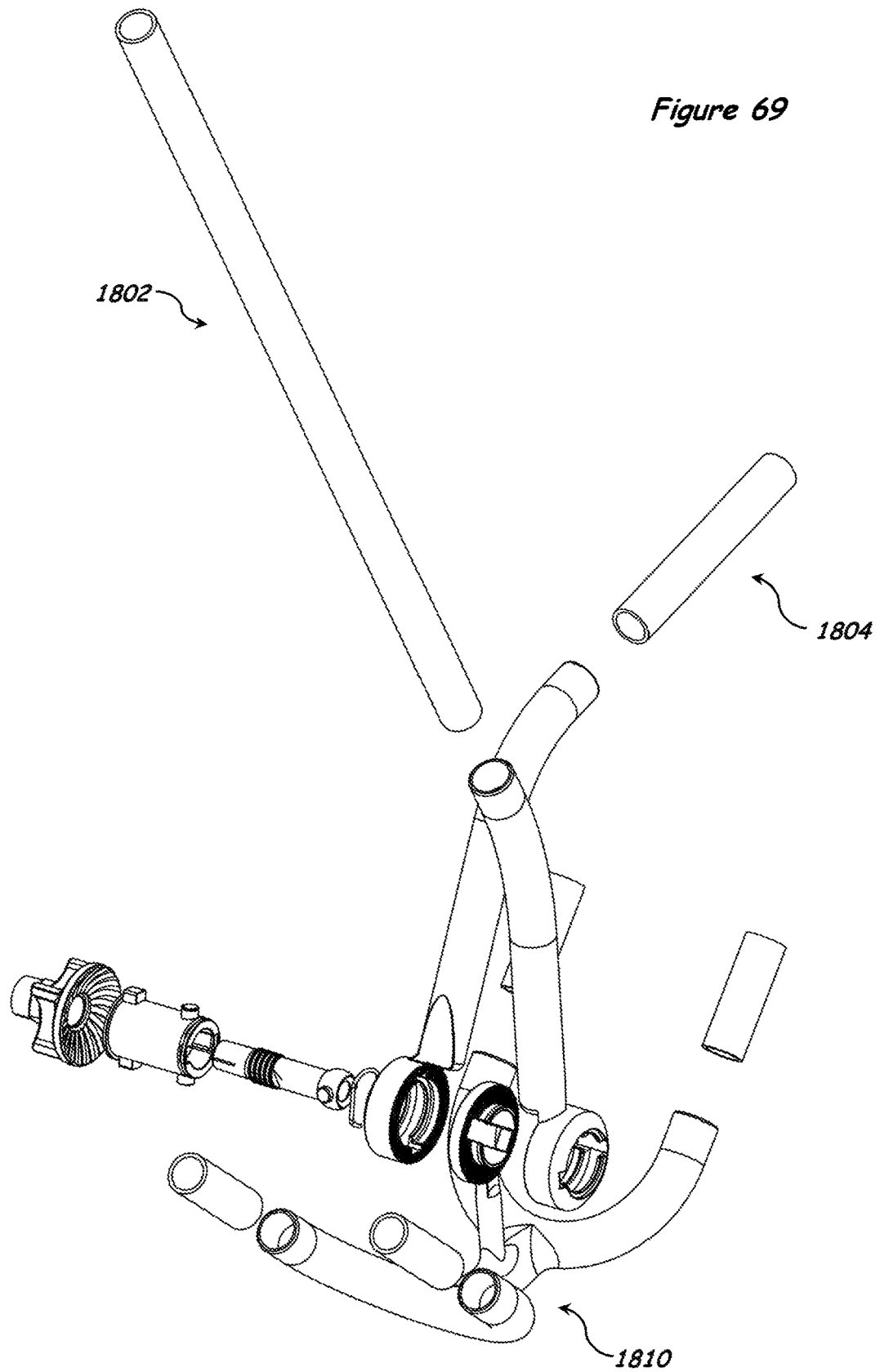
FIG. 69 is a detailed posterior-lateral exploded view of the sixth embodiment of the ankle external fixator.

Referring now to FIGS. 62-64, an alternative embodiment 1700 of the ankle-spanning external fixation system 1600 is illustrated wherein the system 1700 includes the curved foot frame 1706 comprising a U-shaped posterior (e.g., first) frame section and a U-shaped inferior (e.g., second) section connected at the base by a straight frame section. The two U-shaped frame sections are arranged to lie on different planes forming an angle of about 90 degrees. Other angles also lie within the spirit and scope of the various embodiments of the present invention.

Referring now to FIGS. 65-69, an alternative embodiment 1800 of the ankle-spanning external fixation system 1700 is illustrated wherein the first external fixation component 1802, second external fixation component 1804, and the foot frame 1810 are each of modular construction, comprising two or more straight and/or curved segments joined together via plug-socket joints and fixed in place by threading, snap-fitting or interference-fitting. Each of the first external fixation component 1802, second external fixation component 1804, and the foot frame 1810 of the system 1800 can also be made into a unitary structure or unitary modular structure by molding or forming permanent connection among the subcomponents or segments by welding, soldering, crimping, brazing, and gluing/epoxying. The system 1800 can be single-use or disposable.

Figure 70:
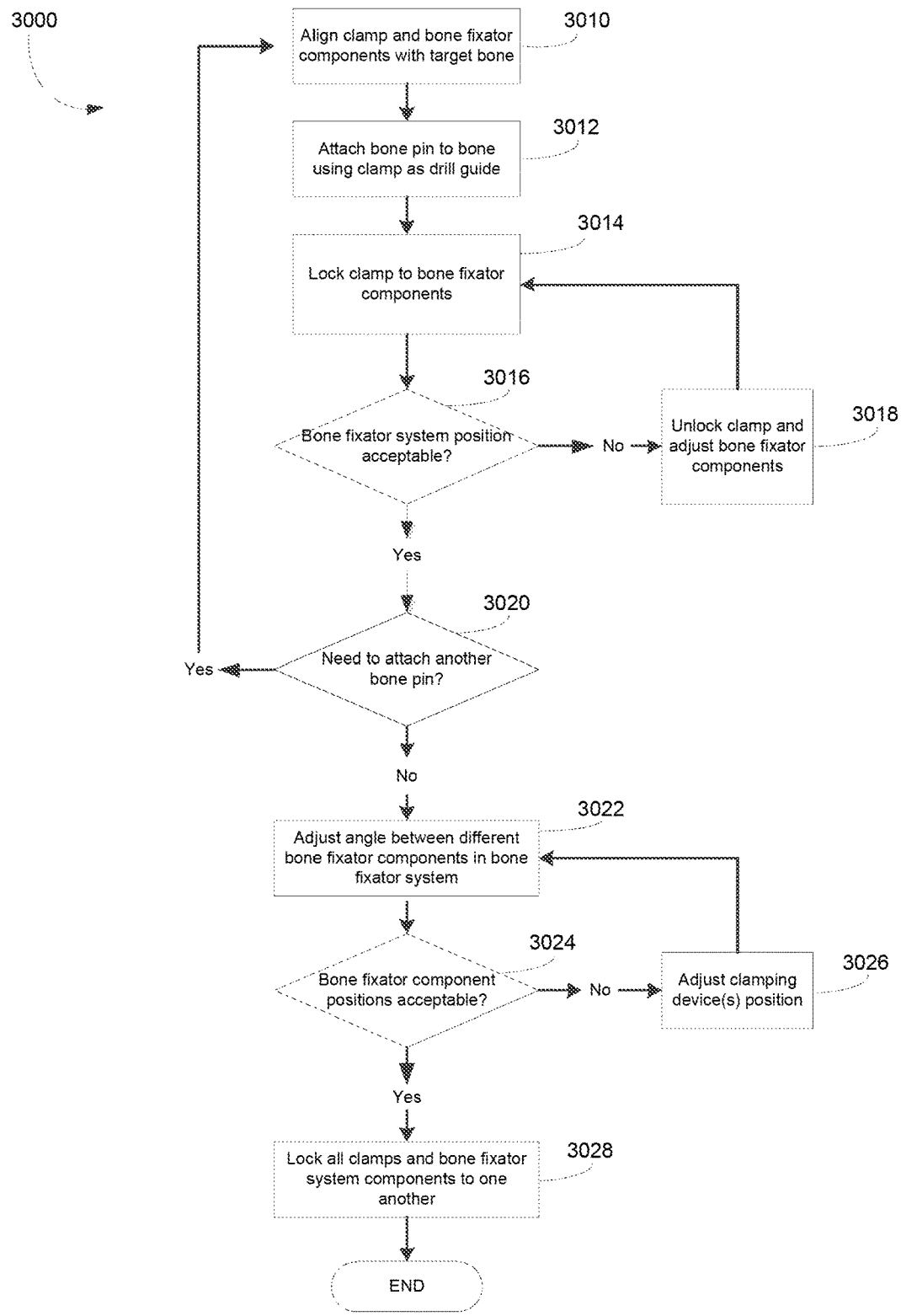
FIG. 70 is a flow diagram of a method of fixating a bone fixator system to a target joint of a subject.

Referring now to FIG. 70, a flow diagram of an embodiment of a method 3000 for fixating a bone fixator system about a target joint is shown. The method may be performed by a variety of users, including healthcare professionals, technicians, and patients installing and/or adjusting the bone fixator system. The bone fixator system used to implement the method may be or include features of any of the fixation systems disclosed herein (e.g., external fixation systems 100, 200, 800, 900, 1000, 1100, 1200, 1400, 1500, 1600, 1700, 1800, etc.) and the clamping devices used herein to implement the method may be or include features of any of the clamping devices and systems disclosed herein (e.g., clamp systems 300, 400, 500, 1300, 2600, etc.).

At 3010, components of a bone fixator system are aligned with target bone(s) about a target joint to be fixated. The target joint may be an elbow, a knee, an ankle, etc. For example, the bone fixator system may include a first fixation component and a second fixation component, the first fixation component may be aligned relative to a first target bone disposed adjacent to the target joint, and the second fixation component may be aligned relative to a second target bone disposed adjacent to the target joint on another side of the knee from the first target bone.

A clamp is also aligned relative to a target bone. For example, a clamp may be aligned with the target bone based on a desired position and/or orientation of a bone pin to be attached to the bone and secured or otherwise received by the clamp. The clamp may also be received on one of the fixation components of the bone fixator system while aligning the clamp.

At 3012, a bone pin is attached (e.g., secured, coupled, drilled in, etc.) to a target bone using a clamp as a drill guide. For example, the clamp may define a through-bore configured to receive the bone pin. The through-bore may be used to sight or otherwise identify a target position on a surface of the target bone at which the bone pin is to be attached to the target bone. The bone pin is received through the through-bore of the clamp, and may be drilled into the bone. The clamp may be locked about the bone pin.

At 3014, the clamp is locked to the bone fixation component. For example, the clamp may include a pair of jaws defining an aperture through which the bone fixation component may pass, and a locking device may be used to force the jaws to compress the bone fixation component in order to lock the clamp to the bone fixation component.

At 3016, it is determined whether the bone fixation system is disposed in a desired orientation (e.g., position and/or angle relative to target joint, target bones, etc.). If the bone fixation system is not disposed in a desired orientation (e.g., the orientation is not acceptable), then at 3018, clamp(s) may be unlocked, providing degrees of freedom allowing for adjustment of the bone fixation system and components of the bone fixation system.

In some embodiments, determining whether the bone fixation system is disposed in a desired orientation includes comparing an observed joint status of the target joint to a desired joint status of the target joint. For example, a clinical goal for the joint may include a particular joint status (e.g., a degree of flexure of the joint, relative angles of the bones about the joint, etc.) to be achieved using the bone fixation system.

If it is determined that the bone fixation is disposed in a desired orientation, then at 3020, it is determined whether an additional bone pin needs to be attached. If it is determined that an additional bone pin is needed, then the procedure outlined in steps 3010, 3012, 3014, 3016, and 3018 may be followed to provide an additional clamp and attach an additional bone pin.

If it is determined that an additional bone pin is not needed, then at 3022, angle(s) between various components in the bone fixation system, such as between a first fixation component and a second fixation component, may be adjusted.

At 3024, after adjusting angles of the bone fixation system, it is determined whether the bone fixation system is disposed in a desired orientation. If it is determined that the bone fixation system is not disposed in a desired orientation, then at 3026, any locked clamp(s) and bone fixation component(s) are unlocked, allowing for adjustment of the orientation of the bone fixation system, such as by adjusting angle(s) between bone fixation components. An angle of a clamp relative to a bone fixation component may be adjusted, such as by adjusting an angle defined by a longitudinal axis of the bone fixation component and a plane transverse to a through-bore of the clamp in which the bone fixation component is received. A position of the clamp relative to the bone fixation component may be adjusted as well, such as by shifting and/or sliding the bone fixation component and the clamp relative to one another.

In some embodiments, the bone fixation system is configured to be fixated about a target ankle joint. The bone fixation system includes a first frame which may be aligned about a first target bone of the lower extremity adjacent to the target ankle joint. The bone fixation system also includes a second frame which may be aligned to at least partially surround the target ankle. For example, the second frame may include an inferior frame portion and a posterior frame portion. Fixating such a bone fixation system may include aligning the first frame with a first target bone of the lower extremity, aligning the second frame such that the inferior frame is disposed in an inferior position relative to the target ankle joint and such that the posterior frame is disposed in a posterior position relative to the target ankle joint, aligning a first clamp with the first target bone, attaching a first bone pin to the first target bone using the first clamp as a drill guide, and locking the first clamp to the first frame. In some embodiments, such a bone fixation system may be further fixated by aligning a second clamp with a second target bone (e.g., a bone of the foot or of the heel), attaching a second bone pin to the second target bone using the second clamp as a drill guide, and locking the second clamp to the second frame.

If it is determined that the bone fixation system is disposed in a desired orientation, then at 3028, all clamp(s) and bone fixation component(s) are locked. For example, locking devices may be used to lock clamp(s) to respective bone fixation component(s). In some embodiments, bone fixation components may be engaged and locked using fasteners or other engagement devices as disclosed herein.

B. Clamping Devices and Systems with Locking Assembly

Referring now to FIGS. 71-76B, various embodiments of a clamping device 3100 including a locking assembly are shown. The clamping device 3100 can be similar to the clamp systems 300, 400, 500, and/or 2600 described herein, with the exception of the features described further below, including the lever mechanism and jaw structures.

In some embodiments, a clamping device (or system) includes a clamp body and a locking assembly. The clamp body includes a first jaw and a second jaw, and defines a first channel configured to accommodate a fixation element (e.g., an external fixation rail, external fixation components described herein such as external fixation component 102, etc.) along a longitudinal axis of the first channel. The first jaw defines a first opening and the second jaw defines a second opening. The locking assembly includes a first locking element, a second locking element, and a lever configured to couple to the second locking element. The first locking element includes a first end and a shaft portion extending from the first end. The shaft portion is sized to pass through the first opening and the second opening. The second opening is sized to restrict the first end from passing through the second opening. The first locking element defines a second channel sized to receive a bone pin. The locking assembly is configured to reduce a distance between the first jaw and the second jaw responsive to rotation of the second locking element relative to the first locking element. The lever is configured to be attached to the second locking element and rotated about the second locking element from a first position to a second position to cause the distance between the first jaw and the second jaw to be reduced further while the first end is in contact with the second opening.

Figure 71:
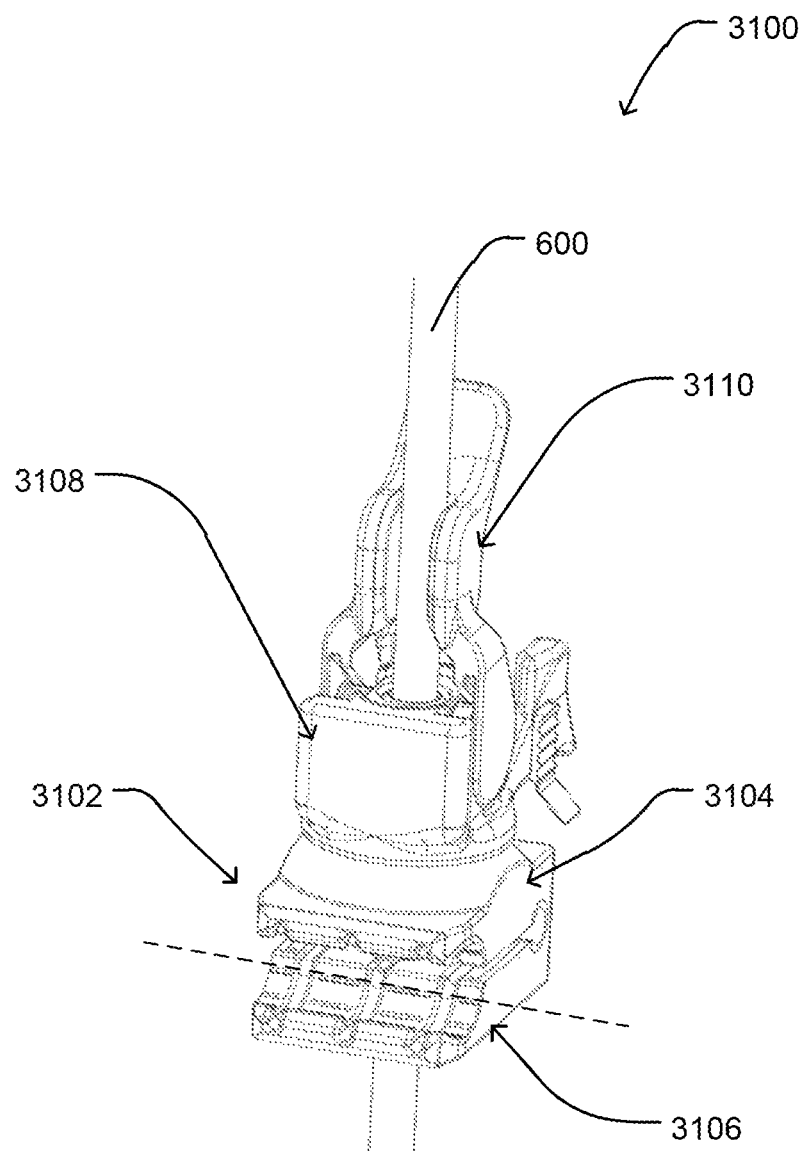
FIG. 71 is a perspective view of an embodiment of a clamping device.

Referring now to FIG. 71, a clamping device 3100 includes a clamp body 3102 and a locking assembly 3108. The clamp body 3102 includes a first jaw 3104 and a second jaw 3106. The locking assembly 3108 includes a lever 3110 (e.g., an extension, a rotatable actuator). The locking assembly is configured to receive a bone pin 600. The clamp body 3102 can define a first channel configured to accommodate a fixation element along a longitudinal axis of the first channel. The first channel can be defined between surfaces of the first jaw 3104 and the second jaw 3106 (e.g., surfaces that face each other). The longitudinal axis can pass through the first channel, and can be equidistant from some, most, or all points of the surfaces of the first jaw 3104 and second jaw 3106 that define the first channel.

Figure 72B:
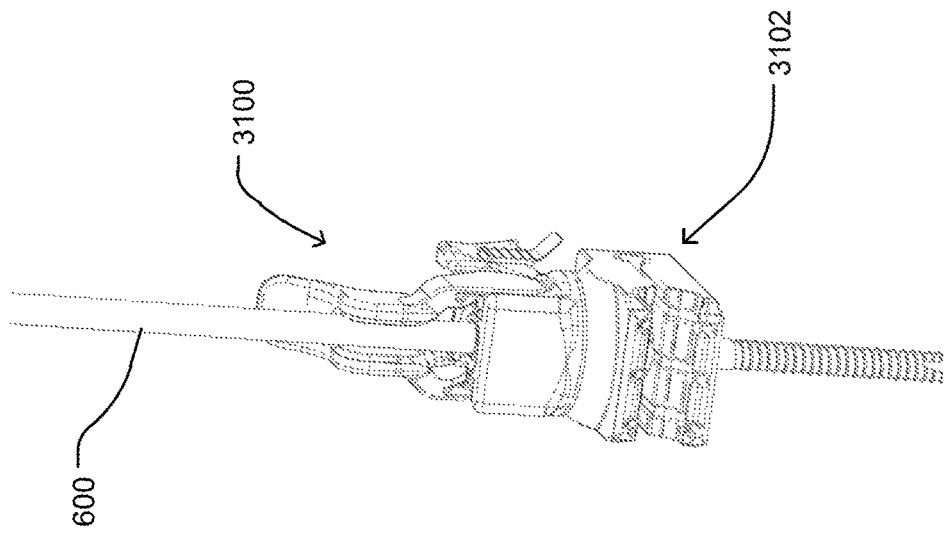
FIG. 72B is a perspective view of an embodiment of a bone pin that is received in the clamping device of FIG. 71.
Figure 72A:
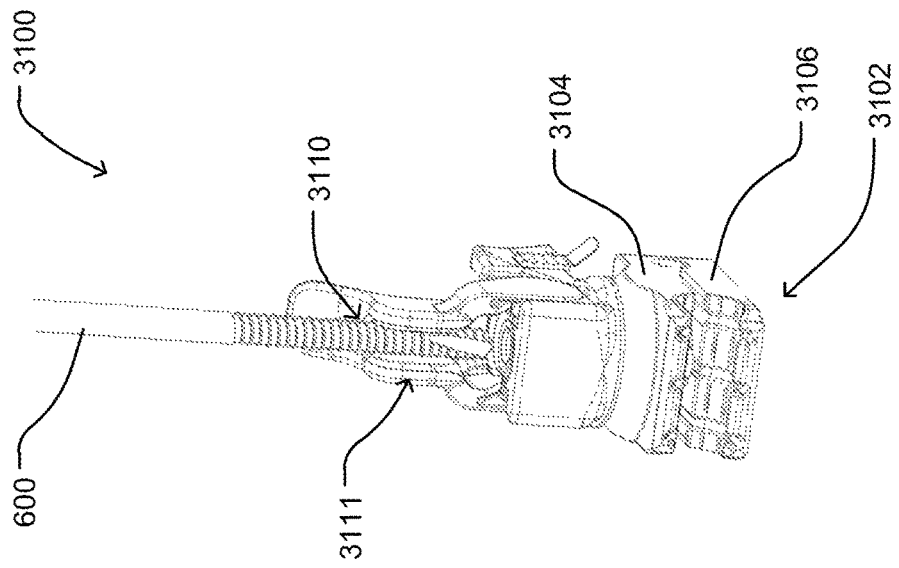
FIG. 72A is perspective view of an embodiment of a bone pin to be received in the clamping device of FIG. 71.

Referring now to FIGS. 72A-72B, the bone pin 600 can be received through the lever 3110 into a remainder of the locking assembly 3100 and the clamp body 3102. Features of the locking assembly 3100 configured to receive, couple to, secure, clamp, and/or manipulate the bone pin 600 are described further herein. As shown in FIGS. 72A-72B, the lever 3110 defines a lever channel 3111. The lever channel 3111 can receive the bone pin 600. The lever channel 3111 can be sized to accommodate the bone pin 600 (e.g., the lever channel 3111 has a diameter or a maximum dimension defined across the lever channel 3111 that is greater than a diameter or maximum dimension defined across the bone pin 600. The lever channel 3111 can have a lever channel radius that is greater than or equal to a radius of an inner surface of a shaft portion of a first locking element of the locking assembly 3100 (see, e.g., first locking element 3120 of FIG. 73A). The lever channel 3111 can help a user guide the bone pin 600 through the locking assembly 3100 to a point on a patient to which the bone pin 600 is to be attached. For example, the bone pin 600 may be placed or rested against the lever 3110 to stabilize the bone pin 600 and align the bone pin 600 with the lever channel 3111 (and the channel 3134 of the locking assembly 3100). The lever channel 3111 can be coaxial with the channel 3134 to receive the bone pin 600 from the channel 3134. While FIGS. 72A-72B illustrate the bone pin 600 as being inserted first through a first end of the clamping device proximal to the first jaw 3104, in some embodiments, the bone pin 600 may also be inserted through a second end of the clamping device proximal to the second jaw 3106.

Referring now to FIGS. 73A-73D, various components of embodiments of the clamping device 3100 are illustrated. The locking assembly 3108 can include a first locking element 3120, a second locking element 3140, and a third locking element 3160. The components of the locking assembly 3108 can be configured to couple to one another, to receive the bone pin 600, and/or to apply forces to the clamp body 3102 causing the first jaw 3104 and second jaw 3106 to move closer to one another.

The first locking element 3120 can be similar to the shafts 306, 406, 2606 described herein. The first locking element 3120 is configured to surround a portion of the bone pin 600, and may include a flexible material allowing the first locking element 3120 to be compressed against the bone pin 600. The first locking element 3120 includes a first end 3122 and a shaft portion 3128 extending from the first end 3122. In some embodiments, the first end 3122 includes protrusions 3124 extending outward from the first end 3122. The protrusions 3124 can be received by a portion of the second jaw 3106, helping to align the first locking element 3120 with the second jaw 3106 and/or restrict motion of the first locking element 3120 relative to the second jaw 3106.

Figure 73A:
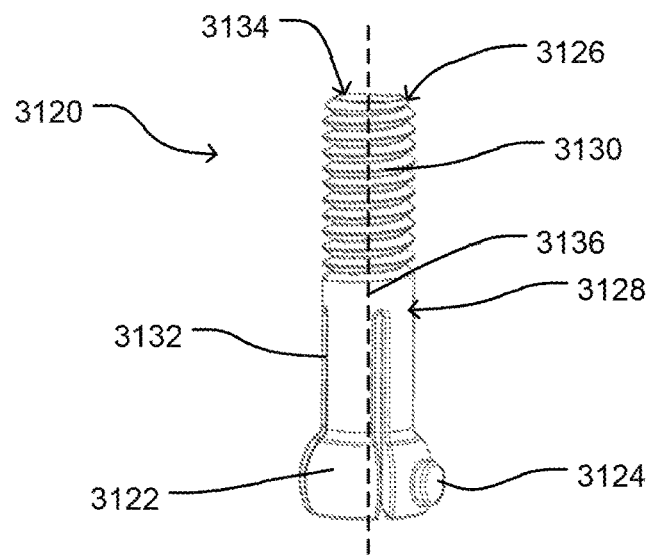
FIG. 73A is a perspective view of an embodiment of a locking element of a locking assembly of the clamping device of FIG. 71.

As shown in FIG. 73A, the first end 3122 has a spheroid shape (e.g., a shape defined such that most or all points on an exterior surface of the spheroid correspond to an ellipse rotated about one of its principle axes). In various embodiments, the first end 3122 can have various shapes (e.g., rectangular solid, cylindrical, shapes defined by a step function, conical or triangular solid). As described further herein with reference to FIG. 75A, the first end 3120 can define a maximum diameter that is greater than a minimum diameter of a second opening of the second jaw 3106, which can restrict motion of the first end 3122 relative to the second opening. The maximum diameter can be less than a shaft diameter of the shaft 3128.

The shaft portion 3128 is sized to pass through the first jaw 3104 and the second jaw 3106 (e.g., via openings of the first jaw 3104 and the second jaw 3106). The shaft portion 3128 can include an engagement feature configured to couple the first locking element 3120 to another component (e.g., the second locking element 3140). For example, FIG. 73A shows the engagement features as threads 3130; the engagement feature could additional be or include recesses, protrusions, interdigitation, or other features configured to engage another component such that the first locking element 3120 may move together with the other component while engaged. The threads 3130 can extend along an outer surface of the first locking element 3120 adjacent to a second end 3126 of the first locking element 3120 opposite the first end 3122.

In some embodiments, the first locking element 3120 defines a channel 3134 sized to accommodate the bone pin 600. For example, a maximum dimension across the channel 3134 can be greater than a maximum dimension across the bone pin 600. The first locking element 3120 and/or the channel 3134 can define a longitudinal axis 3136 (e.g., a channel axis) passing through the channel 3134. The longitudinal axis 3136 can be equidistant from some or all of the points of the channel 3134 (e.g., from an inner surface or wall of the first locking element 3120 defining the channel).

In some embodiments, the first locking element 3120 includes extensions 3132 (e.g., slits, protrusions). The extensions 3132 extend inward from the first end 3122 and the shaft portion 3128 (e.g., from an inner surface or wall of the first locking element 3120 defining the channel 3134). The extensions 3132 can be configured to apply a force against the bone pin 600 in response to compression of the first locking element 3120 (e.g., as the first locking element 3120 is tightened or compressed by the second locking element 3140 or the second jaw 3106).

Figure 73B:
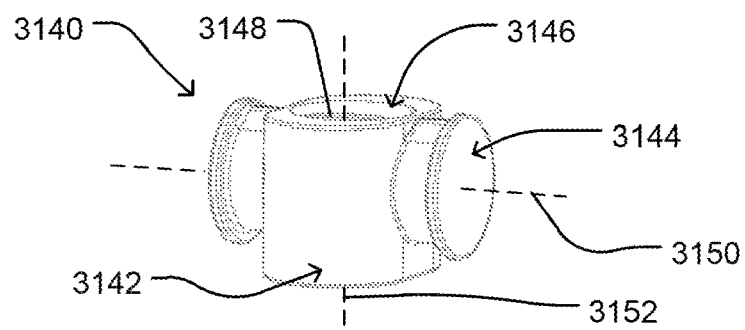
FIG. 73B is a perspective view of an embodiment of another locking element of the clamping device of FIG. 71.

Referring further to FIG. 73B, the second locking element 3140 can include a second locking element body 3142. The second locking element body 3142 can be sized to receive the shaft portion 3128 of the first locking element 3120. The second locking element body 3142 is shown to have a cylindrical shape to facilitate rotation of the second locking element body 3142 in a compact space; however, in various embodiments, the second locking element body 3142 can have other shapes (e.g., polygonal, rectangular).

The second locking element 3140 includes at least one rotational coupler element 3144 extending from the second locking element body 3142. The rotational coupler elements 3144 are configured to couple to (e.g., engage) the lever 3110, such that the lever 3110 can be rotated about the second locking element body 3142. For example, the second locking element 3140 and/or the rotational coupler elements 3144 can define a rotational axis 3150 passing through the second locking element 3140 about which the lever 3110 can rotate.

The second locking element 3140 includes an inner surface 3146 defining a channel in which the shaft portion 3128 of the first locking element 3120 can be received. For example, a maximum dimension across the channel (e.g., from a first point on the inner surface 3146 to a second point opposite the first point) can be greater than or equal to a maximum dimension of an outer surface of the shaft portion 3128. The inner surface 3146 includes an engagement feature configured to couple to or engage with the first locking element 3120. The engagement feature may be complementary to an engagement feature of the first locking element 3120. For example, as shown in FIG. 73B, the inner surface 3146 includes thread receiving members 3148 configured to engage the threads 3130 of the first locking element 3120. The second locking element 3140 and/or the inner surface 3146 can define a longitudinal axis 3152. The longitudinal axis 3152 may be equidistant from some, most, or all points on the inner surface 3146. The longitudinal axis 3152 may be in the same plane as and/or perpendicular to the rotation axis 3150. In some embodiments, the lever 3110, when coupled to the rotational coupler elements 3144, can apply a force to the rotational coupler elements 3144 in a direction perpendicular to the longitudinal axis 3152, causing the second locking element 3120 to rotate about the longitudinal axis 3152. In some embodiments, the locking assembly 3108 defines an engagement axis along which the bone pin 600 is received. The second locking element 3140 may be rotated about the engagement axis. For example, the engagement axis may coincide with the longitudinal axes 3136, 3152 when the second locking element 3140 is engaged to the first locking element 3120.

As the thread receiving members 3148 engage the threads 3130 of the first locking element 3120, the second locking element 3140 can be coupled, engaged, attached, and/or secured to the first locking element 3120. The longitudinal axis 3152 may align with the longitudinal axis 3136 when the first locking element 3120 is received in the channel of the second locking element 3140 (e.g., when the thread receiving members 3148 engage the threads 3130).

The engagement of the receiving members 3148 and the threads 3130 may restrict motion between the first locking element 3120 and the second locking element 3140. For example, when the thread receiving members 3148 engage the threads 3130, a force applied to the first locking element 3120 along the longitudinal axis 3136, or to the second locking element 3140 along the longitudinal axis 3152, may be insufficient (e.g., less than a threshold force that is significantly greater than can be applied to the locking elements 3120, 3140 by a typical user) to cause the first locking element 3120 to move along the longitudinal axis 3152 relative to the first locking element 3120. Instead, rotation of the second locking element 3140 about the shaft portion 3128 of the first locking element 3120, due to the engagement of the threads 3130 and the thread receiving members 3148, allows the first locking element 3120 to be translated through the second locking element 3140. In some embodiments, a portion of the shaft portion 3128 having the threads 3130 includes a material that is flexible or compressible, such that engaging the second locking element 3140 to the first locking element 3120 about the threads 3130 (or another engagement feature) flexes, bends, or compresses the shaft portion 3128 against the bone pin 600 (e.g., the extension 3132 may be forced against the bone pin 600), which can increase locking of the bone pin 600.

Figure 73C:
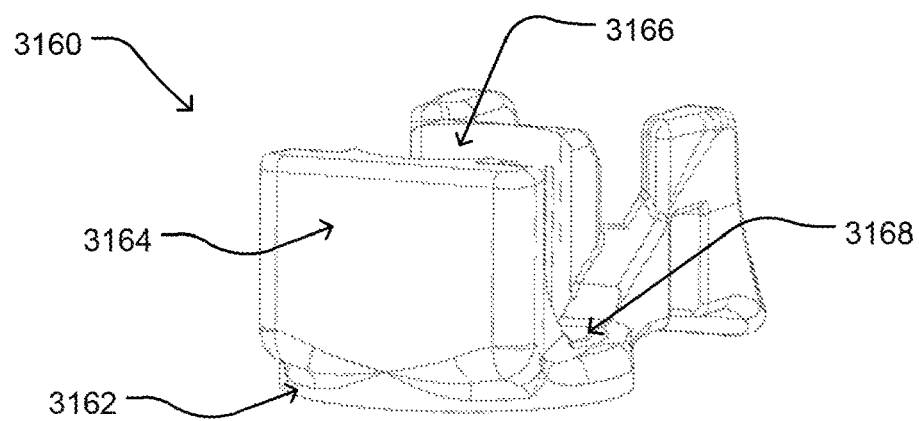
FIG. 73C is a perspective view of an embodiment of another locking element of the clamping device of FIG. 71.

Referring now to FIG. 73C, the third locking element 3160 can include a base portion 3162. The base portion 3162 is attachable to the first jaw 3104 (e.g., to a surface of the first jaw 3104 opposite the second jaw 3106). The third locking element 3160 can include a receiving portion 3164 extending from the base portion 3162. The receiving portion 3164 defines a cavity 3166. The cavity 3166 is configured or sized to receive the second locking element 3140. For example, a maximum dimension across the cavity 3166 can be greater than a maximum dimension across the second locking element 3140.

The receiving portion 3164 can include or define a receiving wall 3168. As described further with reference to FIGS. 74A-74B, the receiving wall 3168 can be shaped or sized to receive or match a cam wall of the lever 3110 (e.g., a curvature of the receiving wall 3168 is complementary to a corresponding curvature of the cam wall). As the lever 3110 is rotated about the second locking element 3140, the lever 3110 applies a varying force against the receiving wall 3168, which can cause the third locking element 3160 to move relative to the second locking element 3140 and/or apply a force against the first jaw 3104. In some embodiments, features of the third locking element 3160 may be excluded, or may be incorporated in the lever 3110 or the second locking element 3140. For example, the lever 3110 may be configured to attach to the first jaw 3104, such that rotation of the lever 3110 against the first jaw 3104 causes a varying force to be applied to the first jaw 3104.

Figure 73D:
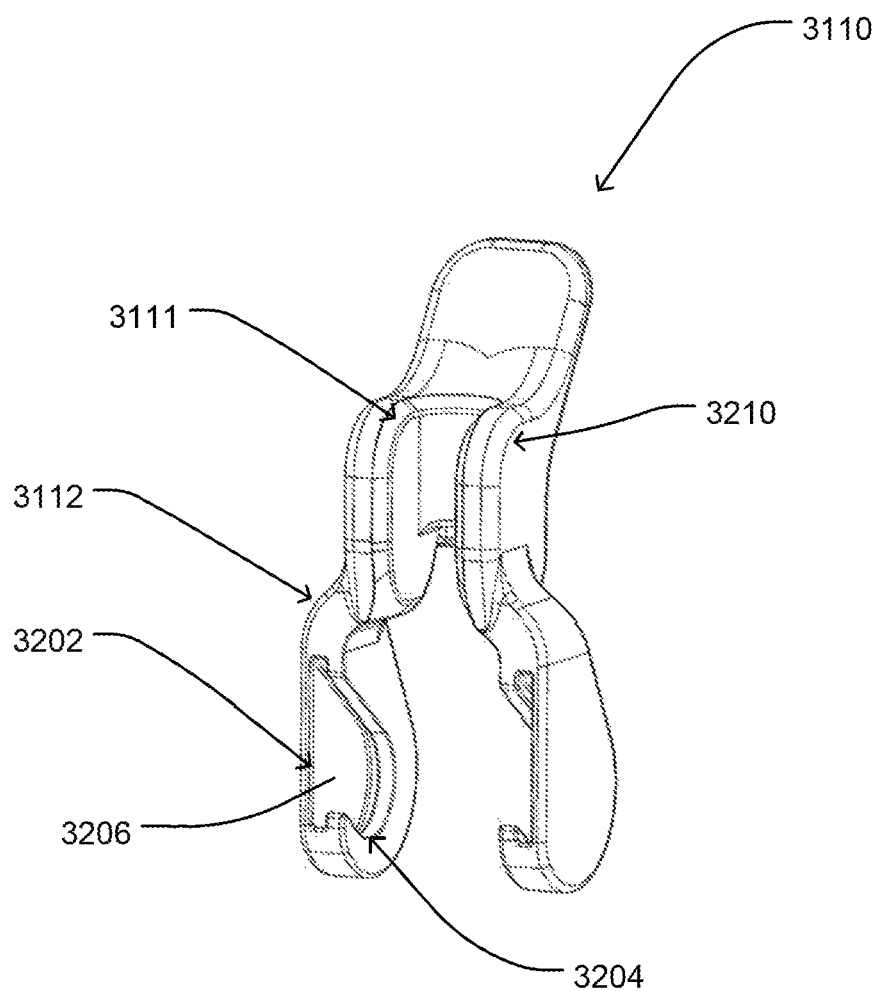
FIG. 73D is a perspective view of an embodiment of a lever of the clamping device of FIG. 71.

As shown in FIG. 73D, the lever 3110 includes a cam wall 3112. An inner surface 3202 of the cam wall 3112 (e.g., a surface facing towards the lever channel 3111) and/or an inner cam wall 3204 defines a center 3206. The inner surface 3202 and the inner cam wall 3204 are shaped, configured, and/or sized to engage the rotational coupler elements 3144 of the second locking element body 3142. For example, a radius of curvature of the inner cam wall 3204 and/or the inner surface 3202 can match (e.g., is equal to or is greater than an amount less than a threshold amount, resulting in a fit between the lever 3110 and the rotational coupler element 3144) a radius of curvature of the rotational coupler elements 3144. As the lever 3110 rotates about second locking element 3140, the rotation axis 3140 of the second locking element 3140 aligns with the center(s) 3206 of the lever 3110.

In some embodiments, the lever 3110 includes a tab wall 3210. The tab wall 3120 is configured to be received by a corresponding tab receiver 3212 of the third locking element 3160. For example, when the lever 3110 is rotated about the rotation axis 3150 of the second locking element 3140 to the second position, the tab receiver 3212 can be coupled to or secure the tab wall 3210, restricting rotation of the lever 3110 towards the first position. In addition, the tab wall 3210 can provide a user with a lever arm to facilitate rotation of the lever 3110 both about the longitudinal axis 3152 of the second locking element 3140 when the second locking element 3140 is being threaded onto the first locking element 3120 to translate the first locking element 3120 through the second locking element 3140 (e.g., translate the first locking element 3120 in a direction from the clamp body 3102 towards the second locking element 3140), and about the rotation axis 3150 as the lever 3110 is rotated from the first position towards the second position. In some embodiments, a length of the lever 3110 (e.g., from the center 3206 to a point at which the tab wall 3210 terminates) is greater than a threshold length required to apply sufficient force to rotate the lever 3110 from the first position to the second position to clamp the fixation element and the bone pin 600, and less than a length (e.g., a greatest length) of the third locking element 3160 and/or a length (e.g., a greatest length) of the clamp body 3102, providing a compact, effective mechanism for clamping the fixation element and the bone pin 600 (e.g., securing positions and/or orientations of the fixation element and the bone pin 600 relative to one another in space).

Referring now to FIGS. 74A-74B, various features of the engagement and interaction between the lever 3110, the third locking element 3160, and the clamp body 3102 are illustrated. The cam wall 3112 defines a first radius $r_1$, and a second radius $r_2$. The second radius $r_2$ is greater than the first radius $r_1$. The radii $r_1$, $r_2$ can be defined from a center of rotation of the cam wall 3112. The center of rotation of the cam wall 3112 may correspond to a center of an inner surface of the cam wall 3112 (see FIG. 73D) (e.g., a center that is equidistant from some, most, or all points on an inner cam wall configured to couple to the rotational coupler element 3144, such that when the lever 3110 rotates about the second locking element 3140, the rotation axis 3150 of the second locking element 3140 coincides with the center of the inner surface and/or the center of rotation).

In some embodiments, the lever 3110 is configured to rotate from a first position or orientation (e.g., a position or orientation as shown in FIG. 74A, in which the lever channel 3111 is aligned with a longitudinal axis of the bone pin 600) to a second position. The second position may be a position or orientation as shown in FIG. 74B, in which the cam wall 3112 may be flush with the receiving wall 3168 and/or the lever 3110 can be secured by a retaining feature of the third locking element 3160. The second position or orientation may be any other position or orientation as the lever 3110 is rotated between the position shown in FIG. 74A and the position shown in FIG. 74B. The rotation from the first position to the second position may occur about the center of rotation of the cam wall 3112, such as when the lever 3110 is coupled to the second locking element 3140, such that the lever 3110 rotates about the rotation axis 3150 of the second locking element 3140. As the lever 3110 rotates from the first position to the second position, the radius of the cam wall 3112 in contact with a contact point 3170 of the receiving wall 3168 increases from the first radius $r_1$ to the second radius $r_2$.

In embodiments, configurations, and/or arrangements of the clamping device 3100 in which the third locking element 3160 is attached to the first jaw 3104, the first end 3122 of the first locking element 3120 is in contact with the second jaw 3106 on a side of the second jaw 3106 opposite the first jaw 3104, the second locking element 3140 is engaged to the first locking element 3120, and the lever 3110 is coupled to the second locking element 3140, the distance between the center of rotation of the lever 3110 and the first end 3122 is fixed such that the increase in radius of the cam wall 3112 contacting the receiving wall 3168 increases a distance between the second locking element 3140 and the base portion 3162, causing the first end 3122 to pull the second jaw 3106 towards the first jaw 3104 to offset the increased distance between the second locking element 3140 and the base portion 3162. In some embodiments, the increased distance between the second locking element 3140 and the base portion 3162 is equal to a radius difference $\Delta r$ between the first radius $r_1$ and the second radius $r_2$ the offset distance by which the second jaw 3106 moves towards the first jaw 3104 may be equal to the radius difference $\Delta r$.

In some embodiments, the clamping device 3100 can include a lock release member 3169. The lock release member 3169 is configured to releasably engage, lock, secure, attach, or otherwise couple the lever 3110 to the third locking element 3160. For example, the lock release member 3169 can be configured to apply a force to a first side of the lever 3110 opposite where the lever 3110 is received by the third locking element 3160 to hold or secure the lever 3110 in position. In some embodiments, the lock release member 3169 is or includes actuation member, such as a button, configured to engage or disengage the lever 3110 responsive to actuation (e.g., responsive to being pushed or pulled). In some embodiments, the lock release member 3169 is or includes a key configured to be slidably received and removed from a slot of the third locking element 3160. In some embodiments, the lock release member 3169 can facilitate selective locking of the clamping device 3100, such as to allow a medical professional performing a procedure using the clamping device 3100 to lock or unlock the lever 3110 to make adjustments to the clamping device 3100; the lock release member 3169 may be configured such that only the medical professional may actuate the lock release member 3169, such as when the lock release member 3169 is a key.

Figure 75A:
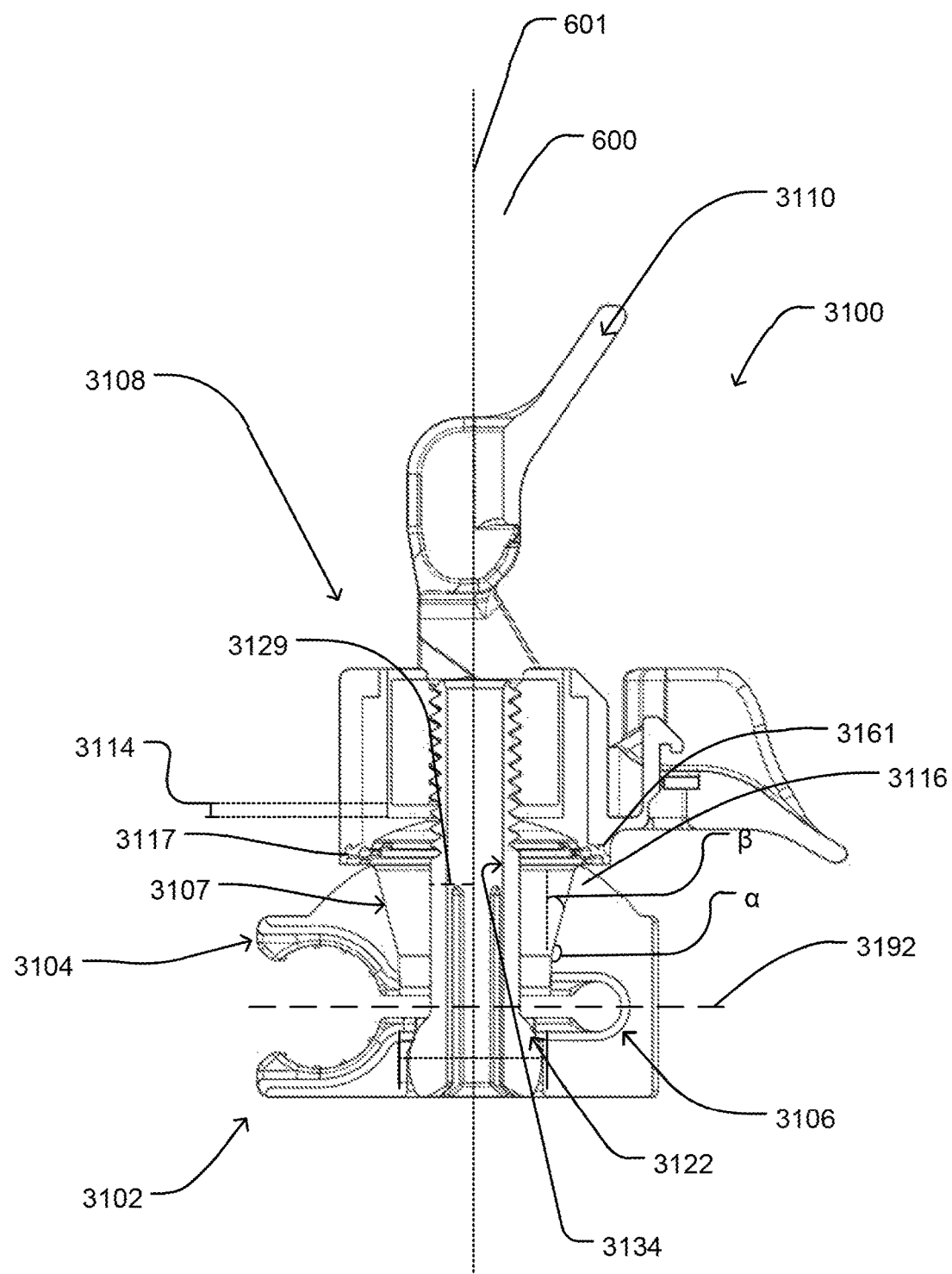
FIG. 75A is a cross section view of an embodiment of the clamping device of FIG. 71 in which the lever is in the first position.
Figure 75B:
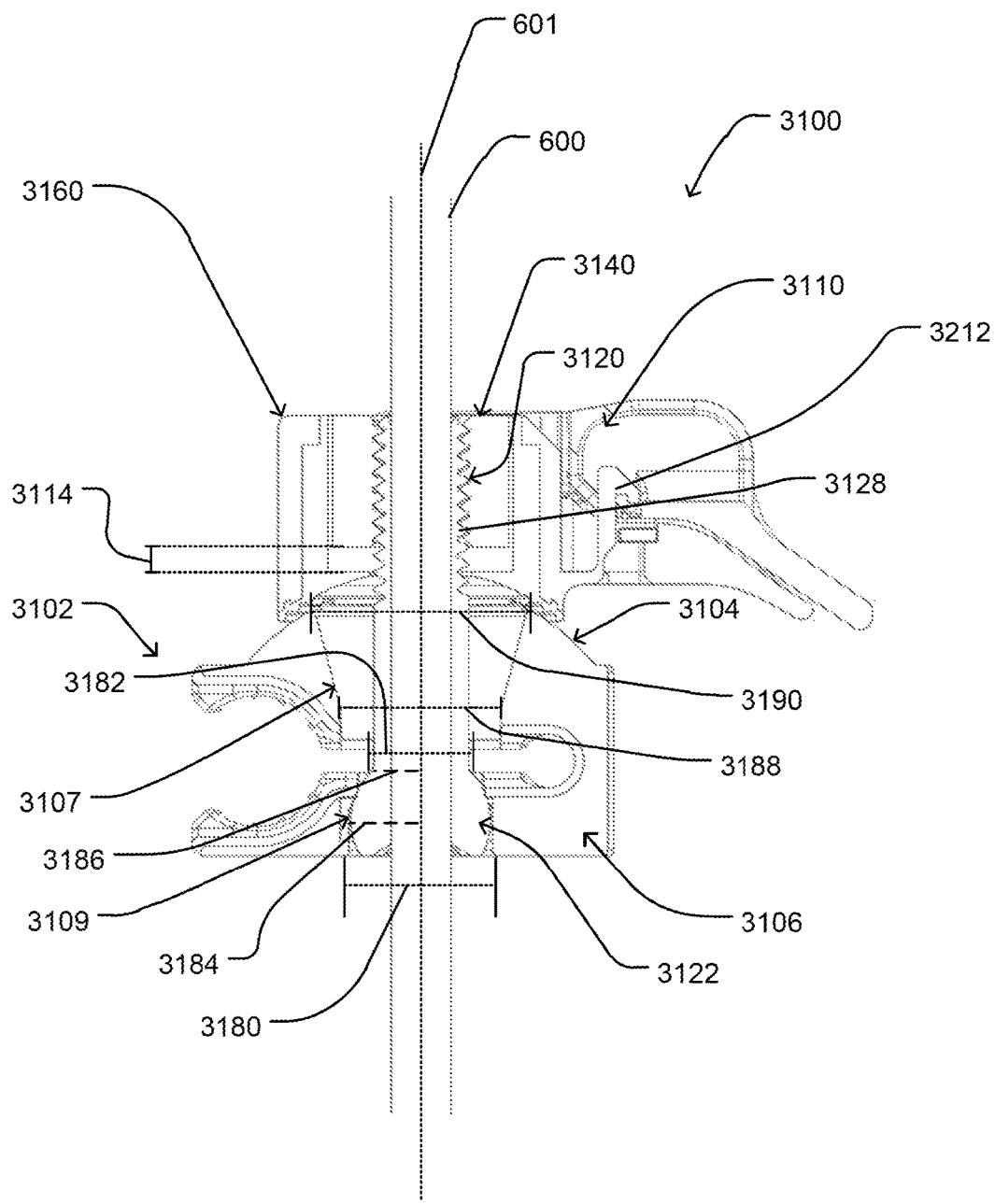
FIG. 75B is a cross section view of an embodiment of the clamping device of FIG. 71 in which the lever is in the second position.

Referring now to FIGS. 75A-75B, various features of interactions between the components of the clamping device 3100 are illustrated. The first jaw 3104 defines a first opening 3107 (e.g., an interior wall or inner wall defines the first opening 3107). The first opening 3107 is sized to receive the shaft portion 3128 of the first locking element 3120. For example, the shaft portion 3128 can define a shaft dimension 3129 (e.g., a radius as illustrated, or a corresponding diameter) in a direction perpendicular to the longitudinal axis of the shaft portion 3128 (e.g., longitudinal axis 3136 shown in FIG. 73A). The first opening 3107 can define a first diameter 3188 (e.g., a first wall diameter) that is greater than or equal to the shaft diameter 3129, and a second diameter 3190 (e.g., a second wall diameter) that is greater than the first diameter 3188. In some embodiments, such as shown in FIGS. 75A-75B, a profile of the first opening 3107 is smooth (e.g., macroscopically smooth, while in other embodiments, the first opening 3107 may have a profile defined by a step function or non-smooth or non-continuous profile). For example, the first opening 3107 may be defined by a conical inner surface of the first jaw 3104.

Gaps or spaces between the wall defining the first opening 3107 and the shaft portion 3128 may define a range of motion, such as for tilting the first locking element 3120 (and thus the bone pin 600 when the first locking element 3120 has received the bone pin 600). The range of motion may be based on an angle $\alpha$ defined between a first portion of the wall having the first diameter 3188, and a second portion of the wall having the second diameter 3190 or another diameter greater than the first diameter 3188. In some embodiments, the angle $\alpha$ is approximately 165 degrees (e.g., 150 degrees; greater than 90 degrees and less than or equal to 180 degrees; greater than or equal to 120 degrees and less than or equal to 175 degrees; greater than or equal to 135 degrees and less than or equal to 170 degrees; greater than or equal to 140 degrees and less than or equal to 160 degrees). In some embodiments, such as shown in FIG. 75A, the second portion of the wall having the second diameter 3190 may be angled relative to the first portion of the wall having the first diameter 3188 to define a tilt angle $\beta$. The tilt angle $\beta$ may represent a range of motion by which the first locking element 3120 may be tilted relative to an orientation in which a longitudinal axis 601 of the bone pin 600, or the corresponding longitudinal axes of the first locking element 3120 and/or the second locking element 3140, are perpendicular to a plane 3192 that is parallel to surfaces of the first jaw 3104 and the second jaw 3106, and/or a plane that is parallel to outer rims of the first opening 3107 or the second opening 3109. For example, if the angle $\alpha$ is 165, then the tilt angle $\beta$ may be 15 degrees, such that the first locking element 3120 may tilt by 15 degrees (e.g., the first locking element 3120 may tilt by a 30 degree range of conical motion) when the outer surface of the shaft portion 3128 of the first locking element 3120 is in contact with the wall defining the first opening 3107. As further described with reference to FIGS. 76A-76B, allowing the first locking element 3120 to tilt or otherwise be oriented throughout a range of motion (e.g., a conical range of motion) within the first opening 3107 may advantageously allow a user to dynamically arrange the clamping device 3100, and thus an external fixation system utilizing the clamping device 3100, in arrangements or configurations during assembly of the external fixation system that are not possible with existing solutions (which may require fixing an angle between a fixation element and a bone pin throughout the assembly process). In some embodiments, the first opening 3107 is conical.

The second jaw 3106 defines a second opening 3109. In some embodiments, while the shaft portion 3128 of the first locking element 3120 is sized or configured to pass through the second opening 3109, the second opening 3109 is sized or configured to restrict or prevent the first end 3122 of the first locking element 3120 to pass through the second opening 3109 (e.g., be moved from a first side of the second opening 3109 opposite the first jaw 3104 to a second side of the second opening 3109 adjacent to the first jaw 3104). In such embodiments, if a force is applied to the first locking element 3120 in a direction that would move the first end 3122 towards the first jaw 3104 while the first end 3122 is in contact with the second opening 3109 (e.g., with a wall of the second jaw 3106 defining the second opening 3109), the force will be transmitted from the first end 3122 to the second jaw 3106. The first locking element 3120 may thus cause the second jaw 3106 to move towards the first jaw 3104.

In some embodiments, the clamp body 3102 includes a first material that is flexible (e.g., bends or otherwise changes in shape in response to a mechanical force). In response to a force applied to the second jaw 3106 by the first end 3122, the clamp body 3102 may be reduced in size (e.g., the second jaw 3106 may move towards the first jaw 3104; a distance between the second jaw 3106 and the first 3104 may decrease). As the second jaw 3106 moves towards the first jaw 3104, a clamping force applied to a fixation element received in the first channel between the jaws 3104, 3106 may be increased, increasing security of the fixation element. In some embodiments, the first end 3122 includes a second material that is flexible. The first material of the clamp body 3102 may be more flexible than the second material of the first end 3122, such that any bending, flexing, or other change in shape that occurs in response to a force applied by the first end 3122 to the second jaw 3106 will predominantly (or totally) result in movement of the second jaw 3106 towards the first jaw 3104. The first material of the clamp body 3102 may be located between the first jaw 3104 and the second jaw 3106, acting as a pivoting member for movement of the second jaw 3106 towards the first jaw 3104.

In some embodiments, the first end 3122 may include a second material that is flexible or compressible. The second material may be more flexible or compressible than a wall defining the second opening 3109. As a force is applied by the first end 3122 against the second opening 3109, some or all of the force may cause the first end 3122 to compress or flex away from the second opening 3109 (e.g., compress or flex inwards), thus transmitting the force to the bone pin 600 and increasing a clamping force for securing the bone pin 600. In some embodiments, where the first locking element 3120 includes slits 3132, the force applied by the first end 3122 against the second opening 3109 may additionally or alternatively cause the slits 3132 to move towards the bone pin 600, similarly increasing a clamping force for securing the bone pin 600. The second material may be configured to be compressed in a plane orthogonal to the channel 3134 in response to a force applied by the second opening 3109 against the first end 3122.

The second opening 3109 (e.g., a wall defining the second opening 3109) can include a first portion defining a first diameter 3180 (e.g., a dimension across the second opening 3109) that is greater than a maximum diameter 3184 (e.g., a dimension across the first end 3122, a dimension perpendicular to longitudinal axis 3136 of the first locking element 3120) of the first end 3122, and a second portion defining a second diameter 3182 that is less than a minimum diameter 3186 (e.g., a dimension across the first end 3122, a dimension perpendicular to a longitudinal axis 3136 of the first locking element 3120) of the first end 3122. As such, the first end 3122 may not pass any further through the second opening 3109 towards the first jaw 3104 once the minimum diameter 3186 of the first end 3122 contacts the second diameter 3182. The second diameter 3182 can be closer to the first jaw 3104 than the first diameter 3180, such that the second portion is configured to restrict the first end 3122 from being moved further towards the first jaw when the first end is in contact with the second portion.

As further described with regards to FIGS. 76A-76B, the first end 3122 may be tilted within the second opening 3109, allowing the bone pin 600 to be tilted (e.g., to be tilted throughout a conical path or conical range of motion). In some embodiments, the range of tilting may be determined based on at least one of the first diameter 3180 of the second opening 3109, the second diameter 3182 of the second opening 3109, the first diameter 3188 of the first opening 3107, and/or the second diameter 3190 of the first opening 3109. In other words, the space defined by the first opening 3107 and/or the space defined by the second opening 3109, enable the first locking element 3120 to be re-oriented within the first opening 3107 and the second opening 3109.

Referring further to FIGS. 75A-75B, and back to FIGS. 74A-74B, as the lever 3110 rotates from the first position to the second position, the portion of the cam wall 3112 contacting the receiving wall 3168 of the third locking element 3160 increases in radius from $r_1$ to $r_2$, increasing the distance between the center of rotation of the lever 3110 and the base portion 3162. As the second locking element 3140 is fixed to the lever 3110 (e.g., when the lever 3110 is rotatably coupled to the second locking element 3140), increasing the distance between the center of rotation of the lever 3110 and the base portion 3162 increases a distance 3114 between the second locking element 3140 and the third locking element 3160 (and/or between the second locking element 3140 and the clamp body 3102), such as to move the second locking element 3140 away from the clamp body 3102. While the second locking element 3140 is engaged to the first locking element 3120 (e.g., while thread receiving members 3148 engage threads 3130 of the first locking element 3120), the distance between the second locking element 3140 and the first end 3122 may be fixed, resulting in a force causing the first end 3122 to move towards the first jaw 3104, where force is transmitted to the second jaw 3106. The distance 3114 may be equal to the radius difference $\Delta r$ as the lever 3110 rotates from the first position to the second position.

Referring further to FIGS. 75A-75B, in some embodiments, the clamp body 3102 includes at least one engagement member 3117 extending from an outer surface of the first jaw 3104 (e.g., a surface of the first jaw 3104). For example, the clamp body 3102 can include an annular protrusion 3116 similar to the annular protrusion 312 or the annular protrusion 512 described herein that terminates in engagement members 3117. The base portion 3162 of the third locking element 3160 may include at least one engagement receiving feature 3161 configured to engage the engagement members 3117. In some embodiments, the engagement receiving feature 3161 is configured to ratchet, such that the third locking element 3120 may be rotated in a first direction (e.g., clockwise), but not in second direction (e.g., counter-clockwise). In some embodiments, the engagement members 3117 include at least one of interdigitation or radial serrations. In some embodiments, the third locking element 3160 is configured to selectively engage first jaw 3104 (e.g., only when the lever 3110 is in the second position), allowing the bone pin 600 to be tilted unless then third locking element 3160 is engaged to the first jaw.

Referring now to FIGS. 76A-76B, the range of motion defined by the first opening 3107 and/or the second opening 3109 (see FIGS. 75A-75B) allow the first locking element 3120, and thus the bone pin 600, to be rotated (e.g., conically rotated, tilted, conically tilted), enabling a user to arrange the clamping device 3100 in a variety of orientations while assembling the clamping device 3100. When the lever 3110 is brought to the second position, the additional security and/or locking provided may also secure the clamping device 3100 in an orientation where the bone pin 600 is tilted. For example, the clamping device 3100 may be assembled while the lever 3110 is in the first position, at which point the first locking element 3120 may still be tilted; when the lever 3110 is brought to the second position, then additional security and/or locking may apply a sufficient force to restrict further tilting of the first locking element 3120.

Clamping devices and systems manufactured in accordance with the embodiments disclosed herein can improve external fixation by providing a compact, elegant mechanism to clamp, lock, or otherwise secure a bone pin and an external fixation element (e.g., a rail) relative to one another. For example, such systems can allow a surgeon or other user to arrange the components of the clamping system in a desired orientation, rotate the second locking element about the first locking element to tighten the components of the system, perform any additional adjustments or movements that may be necessary, and then complete the locking of the system by rotating the lever from the first position to the second position, which can take advantage of the lever arm provided by the lever to increase the force that can be applied to compress and tighten against the bone pin and rail, while maintaining a form factor that is compact and/or has a low profile, reducing the opportunity for contact with surrounding components or the environment to disturb the clamping of the bone pin and rail.

The principles, preferred embodiments and modes of operation of the present invention have been made apparent in the foregoing description.

Although the embodiments are numbered with, for example, "first," "second," or "third," or "fourth," the ordinal numbers do not imply priorities of the embodiments.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A locking assembly, comprising:
a first locking component including a base, the base including a first surface and a cam receiver extending from the first surface to a cam receiver edge, the cam receiver configured to receive a cam, the cam receiver edge having a first edge point closest to the first surface, the first surface defining an opening which is not parallel to a plane passing through the cam receiver;
a second locking component including a first end, a second end, and a shaft portion extending from the first end to the second end, the second locking component configured to be coupled to the first locking component to translate through the opening along a first axis;
the cam including a cam edge and defining a center of rotation, a first radius extending from the center of rotation to a first point of the cam edge, and a second radius extending from the center of rotation to a second point of the cam edge, the second radius perpendicular to and less than the first radius, the cam defines a channel configured to receive a bone pin;
the cam configured to be rotated along the cam receiver edge about a second axis which is not parallel to the first axis from a first position at which the center of rotation is spaced from the first edge point by the first radius to a second position at which the center of rotation is spaced from the first edge point by the second radius.

2. The locking assembly of claim 1, wherein the second locking component includes one or more threads configured to engage corresponding thread receiving members of the first locking component to be rotated while being translated along the first axis.

3. The locking assembly of claim 1, wherein the cam receiver edge is concave.

4. The locking assembly of claim 1, wherein the cam includes a tab extending from the cam edge and the first locking component includes a tab receiver extending from the base, the tab receiver configured to removably secure the tab to the base when the cam is at the second position.

5. The locking assembly of claim 4, further comprising a lock release member configured to cause the tab receiver to release the tab.

6. The locking assembly of claim 1, wherein the channel is configured to contact the bone pin when the cam is at the first position.

7. The locking assembly of claim 1, wherein rotating the cam from the first position to the second position adjusts a distance between the first end of the second locking component and the center of rotation of the cam.

8. The locking assembly of claim 1, wherein the first axis is perpendicular to the second axis.

9. The locking assembly of claim 1, wherein the cam includes a second cam edge spaced from and parallel to the cam edge.

10. A surgical kit for an external fixator system, comprising:
a first locking component including a base, the base including a first surface and a cam receiver extending from the first surface to a cam receiver edge, the cam receiver configured to receive a cam, the cam receiver edge having a first edge point closest to the first surface, the first surface defining an opening which is not parallel to a plane passing through the cam receiver;
a second locking component including a first end, a second end, and a shaft portion extending from the first end to the second end, the shaft portion including at least one rotational engagement feature configured to be coupled to the first locking component to translate the second locking component through the opening along a first axis while being rotated about the first axis;
the cam including a cam edge and defining a center of rotation, a first radius extending from the center of rotation to a first point of the cam edge, and a second radius extending from the center of rotation to a second point of the cam edge, the second radius perpendicular to and less than the first radius, the cam defines a channel configured to receive a bone pin;
the cam configured to be rotated along the cam receiver edge about a second axis which is not parallel to the first axis from a first position at which the center of rotation is spaced from the first edge point by the first radius to a second position at which the center of rotation is spaced from the first edge point by the second radius.

11. The surgical kit of claim 10, wherein the first locking component includes one or more thread receiving members configured to engage the at least one rotational engagement feature of the second locking component.

12. The surgical kit of claim 10, wherein the cam receiver edge is concave.

13. The surgical kit of claim 10, wherein the cam includes a tab extending from the cam edge and the first locking component includes a tab receiver extending from the base, the tab receiver configured to removably secure the tab to the base when the cam is at the second position.

14. The surgical kit of claim 13, further comprising a lock release member configured to cause the tab receiver to release the tab.

15. The surgical kit of claim 10, wherein the channel is configured to contact the bone pin when the cam is at the first position.

16. The surgical kit of claim 10, wherein rotating the cam from the first position to the second position adjusts a distance between the first end of the second locking component and the center of rotation of the cam.

17. The surgical kit of claim 10, wherein the first axis is perpendicular to the second axis.

18. The surgical kit of claim 10, wherein the cam includes a second cam edge spaced from and parallel to the cam edge.

\* \* \* \* \*